(12) United States Patent
Ghiron et al.

(10) Patent No.: US 9,849,301 B2
(45) Date of Patent: Dec. 26, 2017

(54) MAGNETIC STIMULATION COILS AND FERROMAGNETIC COMPONENTS FOR REDUCED SURFACE STIMULATION AND IMPROVED TREATMENT DEPTH

(71) Applicant: Neuronetics, Inc., Malvern, PA (US)

(72) Inventors: Kenneth Marc Ghiron, Malvern, PA (US); Mark Edward Riehl, Doylestown, PA (US); Ian Maxwell Shipway, Bryn Mawr, PA (US)

(73) Assignee: NEURONETICS, INC., Malvern, PA (US)

( * ) Notice: Subject to any disclaimer, the term of this patent is extended or adjusted under 35 U.S.C. 154(b) by 608 days.

(21) Appl. No.: 14/155,445

(22) Filed: Jan. 15, 2014

(65) Prior Publication Data
US 2015/0196772 A1    Jul. 16, 2015

(51) Int. Cl.
*A61N 2/02* (2006.01)
*A61N 2/00* (2006.01)

(52) U.S. Cl.
CPC .............. *A61N 2/006* (2013.01); *A61N 2/02* (2013.01)

(58) Field of Classification Search
CPC ............................................. A61N 2/00–2/12
USPC ....................................................... 600/9–15
See application file for complete search history.

(56) References Cited

U.S. PATENT DOCUMENTS

| 5,116,304 A | 5/1992 | Cadwell |
| 6,425,852 B1 | 7/2002 | Epstein et al. |
| 6,663,556 B2 | 12/2003 | Barker |
| 6,926,660 B2 | 8/2005 | Miller |

(Continued)

FOREIGN PATENT DOCUMENTS

| JP | 2006255314 A | 9/2006 |
| JP | 2010536496 A | 12/2010 |

OTHER PUBLICATIONS

"Guidance for Industry and Food and Drug Administration Staff Class II Special Controls Guidance Document: Repetitive Transcranial Magnetic Stimulation (rTMS) Systems", U.S. Department of Health and Human Services Food and Drug Administration Center for Devices and Radiological Health, Jul. 26, 2011, 26 pages.

(Continued)

*Primary Examiner* — Catherine B Kuhlman
(74) *Attorney, Agent, or Firm* — Condo Roccia Koptiw LLP

(57) ABSTRACT

A TMS device may include treatment coils and ferromagnetic components that are configured to be disposed proximate to corresponding ones of the treatment coils. The treatment coils and ferromagnetic components of the TMS device may cooperatively generate a magnetic field that exhibits one or more characteristics that differ from those of a magnetic field that is generated by the treatment coils alone. For example, the magnetic field may exhibit lower induced electrical stimulation intensity in the cranial nerves, while substantially maintaining a penetration depth into the subject's brain. In another example, the magnetic field may exhibit increased penetration depth into the subject's brain, while substantially maintaining induced electrical stimulation intensity in the cranial nerves. The TMS device may be configured to be adjustable and/or reconfigurable, for instance with respect to the anatomy of a subject (e.g., to the shape of the subject's head).

21 Claims, 26 Drawing Sheets

(56) References Cited

U.S. PATENT DOCUMENTS

| | | |
|---|---|---|
| 7,407,478 B2 | 8/2008 | Zangen et al. |
| 7,824,324 B2 | 11/2010 | Riehl et al. |
| 7,857,746 B2 | 12/2010 | Riehl |
| 7,963,903 B2 | 6/2011 | Ghiron et al. |
| 7,976,451 B2 * | 7/2011 | Zangen .................... A61N 2/02 600/13 |
| 8,246,529 B2 | 8/2012 | Riehl et al. |
| 8,523,753 B2 | 9/2013 | Schneider et al. |
| 8,956,273 B2 | 2/2015 | Mishelevich et al. |
| 2002/0128533 A1 * | 9/2002 | Barker .................... A61N 2/02 600/14 |
| 2006/0094924 A1 | 5/2006 | Riehl et al. |
| 2007/0260107 A1 * | 11/2007 | Mishelevich ........ A61N 2/004 600/14 |
| 2009/0156884 A1 * | 6/2009 | Schneider ............. A61N 2/02 600/14 |
| 2010/0152522 A1 | 6/2010 | Roth et al. |
| 2010/0185042 A1 * | 7/2010 | Schneider ............. A61N 2/02 600/13 |
| 2010/0286470 A1 | 11/2010 | Schneider et al. |
| 2011/0288364 A1 | 11/2011 | Zangen et al. |
| 2013/0096363 A1 | 4/2013 | Schneider et al. |
| 2013/0267763 A1 | 10/2013 | Schneider et al. |

OTHER PUBLICATIONS

Davey et al., "Suppressing the Surface Field During Transcranial Magnetic Stimulation", IEEE Transactions on Biomedical Engineering, vol. 53, No. 2, Feb. 2006, 190-194.

Deng et al., "Electric Field Depth-Focality Tradeoff in Transcranial Magnetic Stimulation: Simulation Comparison of 50 Coil Designs", Brain Stimulation, vol. 6, Elsevier, Science Direct, Jan. 2013, 1-27, (Supplementary data related to this article is also provided and same can be found online at doi:10.1016/j.brs.2012.02.005).

Salvador et al., "High Permeability Cores to Optimize the Stimulation of Deeply Located Brain Regions Using Transcranial Magnetic Stimulation", Physics in Medicine and Biology, Phys. Med. Biol. 54, May 6, 2009, 3113-3128.

"Coil Configuration Parameters and References", Supplementary Material, pp. 1-14.

R. Salvador, et al. "High permeability cores to optimize the stimulation of deeply located brain regions using transcranial magnetic stimulation", Physics in Medicine and Biology, Phys. Med. Biol. 54 (2009) pp. 3113-3128.

* cited by examiner

MAGNETIC STIMULATION COILS AND FERROMAGNETIC COMPONENTS FOR REDUCED SURFACE STIMULATION AND IMPROVED TREATMENT DEPTH

BACKGROUND

A number of medical ailments may be treated and/or diagnosed through the application of a magnetic field to an afflicted portion of a human subject's body. Neurons and muscle cells are a form of biological circuitry that carry electrical signals and respond to electromagnetic stimuli. When a changing magnetic field is applied to a portion of the body, neurons may be depolarized and stimulated. Muscles associated with the stimulated neurons can contract as though the neurons were firing by normal causes.

A nerve cell or neuron can be stimulated in a number of ways, for example transcutaneously via transcranial magnetic stimulation (TMS). TMS typically uses a rapidly changing (e.g., pulsed) magnetic field to induce a current in a nerve cell, without having to cut or penetrate the skin, or apply electrodes. The nerve is said to "fire" when a membrane potential within the nerve rises above a threshold voltage with respect to its normal ambient level (e.g., approximately −90 millivolts, depending on the type of nerve and local pH of the surrounding tissue).

Magnetic stimulation has proven effective in stimulating regions of the brain, which is composed predominantly of neurological tissue. One area of particular interest is the treatment of depression. Repetitive transcranial magnetic stimulation (rTMS) has been shown to have significant anti-depressant effects for human subjects that do not respond to the traditional methods. A typical rTMS treatment may include application of a subconvulsive stimulation to an area of a subject's brain, for example the prefrontal cortex, in a repetitive, non-invasive manner. Such a treatment may cause a depolarization of cortical neuron membranes. The membranes may be depolarized, for example, by the induction of small electric fields in excess of 1 V/cm that may be generated by a rapidly changing magnetic field.

Typical TMS treatment apparatuses generate pulsed magnetic fields that induce currents in electrically sensitive cells (e.g., nerve cells or neurons). These induced currents typically form a complete circuit in the body, such that a path of zero current through the body is created. The currents induced by a TMS treatment apparatus typically drop off to zero in approximately the middle of this path. The rate of this current drop off may be slowed, for example by spreading the current density generated the TMS apparatus over a wide surface area. However, employing this approach may concentrate return currents, which may lead to higher rates of undesirable side effects (e.g., the stimulation of untargeted regions of a subject's brain).

A typical TMS treatment apparatus may include one or more electrically conductive stimulating coils. Such coils may be configured (e.g., wound) in a single layer, such that the coils may be disposed as close as possible to the tissue that is to be stimulated. Such coils may be capable of stimulating brain tissue at a desirable depth relative to the skull. However, the magnetic field, or fields, typically generated by such coils may cause an undesirably high level of surface stimulation (e.g., of nerves near the surface of the skull).

SUMMARY

As described herein, example TMS devices may include one or more treatment coils and one or more ferromagnetic components that are configured to be disposed proximate to corresponding ones of the one or more treatment coils. The one or more treatment coils and ferromagnetic components of each TMS device may cooperatively generate a magnetic field that exhibits one or more characteristics that differ from those of a magnetic field that is generated by the one or more treatment coils alone.

If an example TMS device, such as one of the example TMS devices described herein, is operated without the one or more ferromagnetic components, a first magnetic field generated by the example TMS device may exhibit characteristics that may include, for example, variable electrical stimulation intensities at various locations in a corresponding first volume of stimulated tissue, a first penetration depth (e.g., into a subject's brain), and a first electric field focality. The variable electrical stimulation intensities may include, for example, a first electrical stimulation intensity at a first location in or on the subject that is near an outer surface of the subject (e.g., at the surface of the subject's scalp, proximate to cranial nerves) and a second electrical stimulation intensity at a second location second location in the subject (e.g., in the subject's brain) that is spaced inwardly from the first location. The first magnetic field may exhibit a first gradient of magnetic field strength that may be representative of a ratio of respective electrical field intensities induced by the first magnetic field at the first and second locations.

When the example TMS device is operated with the one or more ferromagnetic components attached to the corresponding one or more treatment coils, the treatment coils and the ferromagnetic components may cooperatively generate a second magnetic field that may exhibit characteristics that may differ from those of the first magnetic field, and that may include, for example, variable electrical stimulation intensities at various locations in a corresponding second volume of stimulated tissue, a second penetration depth, and a second electric field focality. The variable electrical stimulation intensities may include, for example, a third electrical stimulation intensity at the first location in the subject's brain and a fourth electrical stimulation intensity at the second location in the subject's brain. The second magnetic field may exhibit a second gradient of magnetic field strength that may be representative of a ratio of respective electrical field intensities induced by the second magnetic field at the first and second locations.

The one or more ferromagnetic components may be configured such that when the TMS device is operated with the one or more ferromagnetic components attached to the corresponding one or more treatment coils, cooperative operation of the one or more ferromagnetic components and the one or more treatment coils causes the second gradient of magnetic field strength to differ from the first gradient of magnetic field strength gradient. For example, the one or more ferromagnetic components may be configured such that the second gradient of magnetic field strength is less than the first gradient of magnetic field strength.

When the TMS example device is operated with the one or more ferromagnetic components attached to the corresponding one or more treatment coils, the penetration depth of the second magnetic field generated by the example TMS device may effectively be maintained or may be improved (e.g., increased) relative of that of the first magnetic field, and surface electrical stimulation intensity caused by the second magnetic field may effectively be maintained, or may be reduced relative of that of the first magnetic field.

For example, the electrical stimulation intensity exhibited by the second magnetic field at the first location (e.g., the third electrical stimulation intensity) may be lower than the electrical stimulation intensity exhibited by the first magnetic field at the same location (e.g., the first electrical stimulation intensity), while the electrical stimulation intensity exhibited by the second magnetic field at the second location (e.g., the fourth electrical stimulation intensity) may be effectively the same as the electrical stimulation intensity exhibited by the first magnetic field at the same location (e.g., the second electrical stimulation intensity).

In another example, the electrical stimulation intensity exhibited by the second magnetic field at the first location (e.g., the third electrical stimulation intensity) may effectively the same as the electrical stimulation intensity exhibited by the first magnetic field at the same location (e.g., the first electrical stimulation intensity). The electrical stimulation intensity exhibited by the second magnetic field at the second location (e.g., the fourth electrical stimulation intensity) may be greater than the electrical stimulation intensity exhibited by the first magnetic field at the same location (e.g., the second electrical stimulation intensity).

The amount of energy used by a TMS device (e.g., during TMS treatment) may be reduced if the TMS device includes one or more ferromagnetic components. This may mitigate temperature rise in one or more treatment coils of the TMS device.

Example TMS devices may be configured to be adjustable and/or reconfigurable to conform to one or more locations where TMS treatment will be applied, for instance in accordance with an anatomy of the subject (e.g., to conform to the subject's head).

DETAILED DESCRIPTION

Figure 1A:
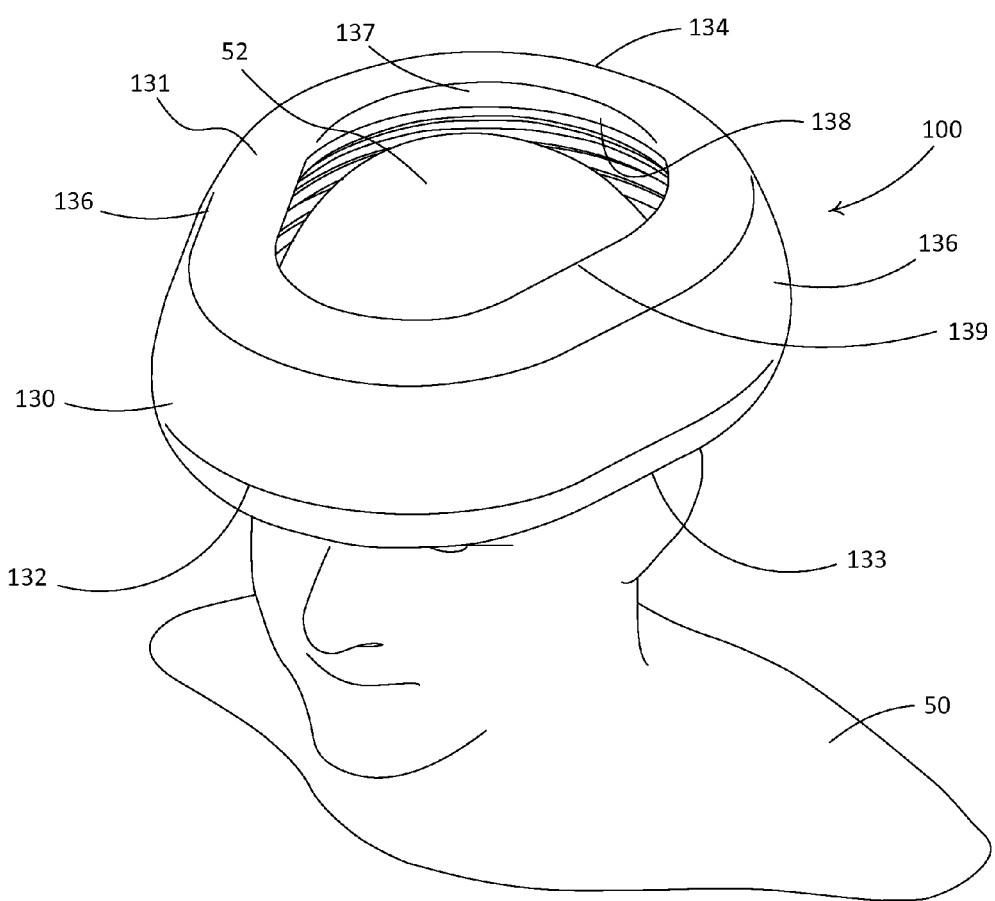
FIG. 1A depicts an example transcranial magnetic stimulation (TMS) device.
Figure 1B:
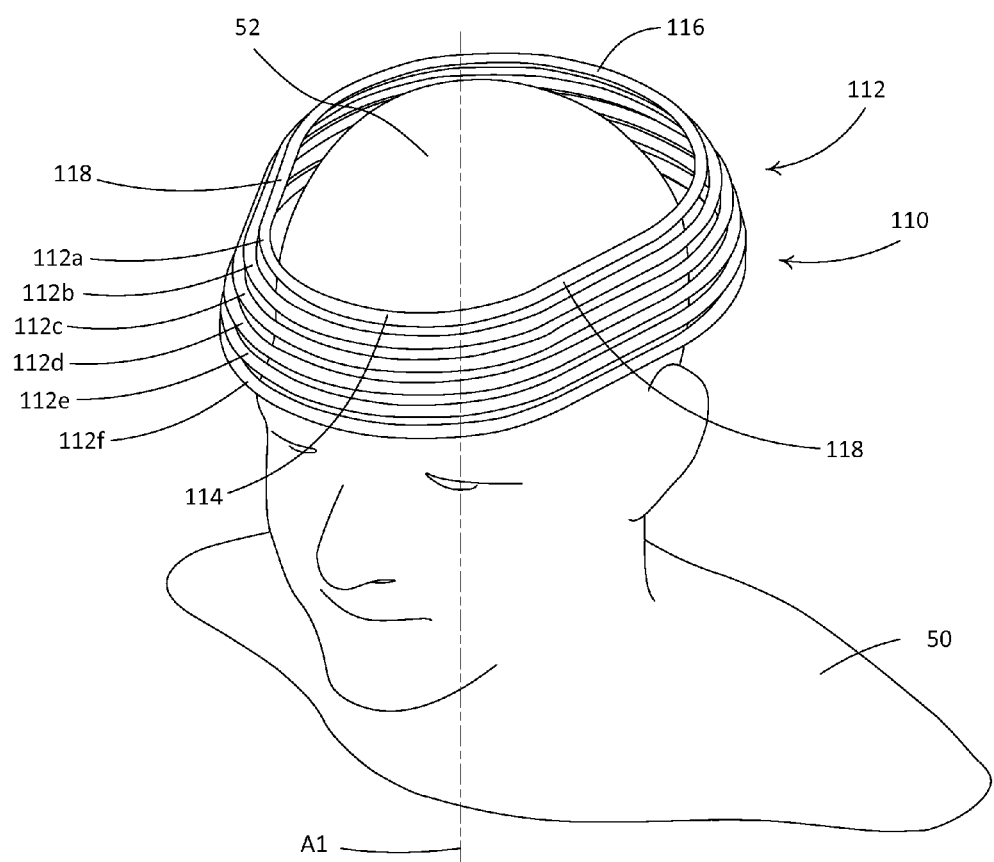
FIG. 1B depicts components of the TMS device of FIG. 1A.

FIGS. 1A and 1B depict a human subject 50 and an example transcranial magnetic stimulation (TMS) device 100 that is configured to generate a changing magnetic field in a target anatomy of a subject 50. The subject 50 may be, for example, a TMS patient. The target anatomy of the subject 50 may be, for example, brain tissue of the subject 50.

As shown, the TMS device 100 includes a treatment coil 110 and a ferromagnetic component 130. The TMS device 100 may be disposed proximate to the head 52 of the subject 50 in preparation for or during TMS treatment, for example as shown in FIG. 1A.

The treatment coil 110 may include one or more windings 112, such as a plurality of windings 112. As shown, the treatment coil 110 has a plurality of windings 112 that includes six windings 112a-112f. It should be appreciated that the treatment coil 110 may include more or fewer windings 112.

The treatment coil 110 may be fabricated from a monolithic piece of material. For example, a length of material (e.g., wire) may be continuously wound so as to define the plurality of windings 112. The windings 112, for example one or more of the windings 112a-112f, may be separately fabricated and supported relative to each other, for example attached to each other using one or more attachment members (not shown). A plurality of windings 112 that are separately fabricated may be placed in electrical communication with one another, for example using one or more electrically conductive attachment members that interconnect respective ones of the windings 112.

The windings 112 may define any suitable shapes, for example the illustrated semi-elliptical shapes. As shown, each winding 112 defines an arc-shaped front segment 114 that may be disposed proximate the front of the subject's head 52, an opposed arc-shaped rear segment 116 that may be disposed proximate the rear of the subject's head 52, and opposed side segments 118 that connect corresponding ends of the front and rear segments 114, 116, respectively, and that may be disposed along corresponding sides of the subject's head 52. The side segments 118 may be substantially straight (e.g., straight or slightly curved). The front, rear, and/or side segments 114, 116, 118 may be configured to conform to corresponding portions of the subject's head 52. As shown, the rear segment 116 of each winding 112 is longer than the corresponding front segment 114, such that each winding 112 is tapered along a direction from the rear segment 116 toward the front segment 114.

Each winding 112 may define a respective length, for example as defined by a perimeter of the winding 112 and measured along a central axis through the winding 112.

Respective ones of the plurality of windings 112 may have the same or different lengths. Each winding 112 may define any suitable cross-section along its length (e.g., perpendicular to its central axis), such as circular. The treatment coil 110, including one or more of the windings 112a-112f, may be made of any material that exhibits suitable electrical conductivity, such as copper.

Respective ones of the windings 112 may have the same or different shapes. The illustrated windings 112a-112f have substantially the same shape relative to one another, but exhibit sequentially increasing lengths from an uppermost winding 112a to a lowermost winding 112f. Stated differently, the winding 112a may have a first length, the winding 112b may define a profile that is the same as or similar to that of the winding 112a, and may have a second length that is longer than the first length, the winding 112c may define a profile that is the same as or similar to those of the windings 112a and 112b, and may have a third length that is longer than the second length, and so on. The uppermost winding 112a may be referred to as an innermost winding of the plurality of windings 112, and the lowermost winding 112f may be referred to as an outermost winding of the plurality of windings 112.

The windings 112a-112f may be configured such that a spacing from winding to winding (e.g., between adjacent windings 112) remains uniform or varies. For example, the spacing between the windings 112a-112f may be defined by the respective lengths, shapes, positioning, etc., of the windings 112a-112f. As shown, the windings 112a-112f of the treatment coil 110 are centered on an axis A1 that extends through the subject's head 52. The axis A1 may, for example, extend along a vertical direction (e.g., a craniocaudal direction) and may pass through a point in the subject's head 52 (e.g., a medially located point).

The treatment coil 110 may be configured to define a coil geometry that conforms to a region of the subject's head 52. For example, two or more of the windings 112a-112f may be spaced from each other vertically such that the coil geometry of the treatment coil 110 may be concave with respect to the subject's head 52. As shown, the treatment coil 110 defines a concave, band-shaped coil geometry that encircles a portion of the subject's head 52.

The TMS device 100 may include a ferromagnetic component 130. The ferromagnetic component 130 may be configured to change one or more characteristics of a magnetic field that is generated by the treatment coil 110. As shown, the ferromagnetic component 130 may be located proximate to the treatment coil 110. The ferromagnetic component 130 may be made of any material that exhibits suitable ferromagnetic properties, such as powdered ferromagnetic iron particles.

The ferromagnetic component 130 may define any suitable shape, for example the illustrated semi-elliptical, band shape. As shown, the ferromagnetic component 130 defines an upper end 131 and an opposed lower end 133 that is spaced from the upper end 131. The ferromagnetic component 130 defines a front section 132 that may be disposed proximate the front of the subject's head 52, an opposed rear section 134 that may be disposed proximate the rear of the subject's head 52, and opposed side sections 136 that extend from the front section 132 to the rear section 134. The side sections 136 may be disposed along corresponding sides of the subject's head 52.

The ferromagnetic component 130 may define an inner surface 137 that faces the subject's head 52 and that is configured to at least partially conform to corresponding portions of the treatment coil 110a and/or to a corresponding portion of the subject's head 52. The inner surface 137, for example as defined by the front, rear, and side sections 132, 134, 136, may define a shape with proportions that are substantially similar to (e.g., slightly larger than) those of a corresponding portion of the subject's head 52.

The ferromagnetic component 130 may be configured to at least partially receive the treatment coil 110, such that the ferromagnetic component 130 is positioned proximate to a portion of the treatment coil 110. For example, the ferromagnetic component 130 may define a recess 138 that extends into the inner surface 137 of the ferromagnetic component 130 and that is configured to receive at least a portion of the treatment coil 110. The recess 138 may be configured to receive one or more of the plurality of windings 112. When the treatment coil 110 is disposed in the recess 138, for example as shown in FIG. 1A, the ferromagnetic component 130 may at least partially surround respective portions of the plurality of windings 112. Portions of the front, rear, and side sections 132, 134, and 136, for example that define the recess 138, may define a shape that is similar to (e.g., effectively the same as) one or more corresponding windings 112.

The ferromagnetic component 130 may define one or more openings that may expose corresponding portions of the subject's head 52, for example to promote cooling during TMS treatment. As shown, the ferromagnetic component 130 defines an opening 139 that extends therethrough. The illustrated opening 139 is located at the upper end 131 of the ferromagnetic component 130. It should be appreciated that the ferromagnetic component 130 may be configured to define more or fewer openings. For example, the ferromagnetic component 130 may be configured to define a plurality of openings therethrough, or may be configured with no opening therethrough (e.g., configured with a dome-like shape).

The TMS device 100 may be configured such that the treatment coil 110 and the ferromagnetic component 130 are supported relative to each other. For example, the TMS device 100 may be configured such that the ferromagnetic component 130 supports the treatment coil 110 (e.g., in the recess 138). One or both of the treatment coil 110 and the ferromagnetic component 130 may include one or more complementary attachment members (not shown) that are configured to enable attachment (e.g., releasable attachment) of the treatment coil 110 to the ferromagnetic component 130. The one or more attachment members may be configured such that the treatment coil 110 and the ferromagnetic component 130 are fixedly supported relative to each other (e.g., in the configuration depicted in FIGS. 1A and 1B). The one or more attachment members may be configured such that the treatment coil 110 and the ferromagnetic component 130 are movable (e.g., repositionable) relative to each other.

When the treatment coil 110 is supported by (e.g., attached to) the ferromagnetic component 130, the treatment coil 110 may be electrically isolated from the ferromagnetic component 130, for example using a dielectric. As shown, the dielectric may be air, and the plurality of windings 112 may be spaced from the inner surface 137 of the ferromagnetic component 130 when the treatment coil 110 is attached to the ferromagnetic component 130 (e.g., disposed in the recess 138). The treatment coil 110 may be attached to the ferromagnetic component 130 using one or more attachment members that are made of any suitable electrically isolating (e.g., dielectric) material. As depicted in FIG. 1A, when the treatment coil 110 is disposed in the recess 138 of the ferromagnetic component 130, the treatment coil 110 may be at least partially enclosed by the ferromagnetic component 130.

The TMS device 100, for example as configured and oriented relative to a subject 50 as depicted in FIG. 1A, may be operated to cause the generation of a magnetic field in the subject's brain that may exhibit greater intensity in a band shaped region of relatively distributed intensity in the subject's brain than in an upper portion of the subject's brain. When the TMS device 100 is oriented relative to the subject 50 as shown, the magnetic field may be distributed so as to be simultaneously resident in both the first and second hemispheres of the subject's brain.

When the TMS device 100 is oriented as depicted in FIG. 1A, the treatment coil 110 may define induced current return paths that are close to the subject's head 52. This may assist with the driving of the return currents, and may improve the efficiency of the TMS device 100.

It should be appreciated that the TMS device 100 is not limited to the illustrated orientation relative to a subject (e.g., to the head 52 of the subject 50), and that the TMS device 100 may be differently oriented relative to the subject, such that the portion of the magnetic field that exhibits greater intensity is localized in a different location of the subject's anatomy (e.g., a different location in the subject's brain).

Figure 2A:
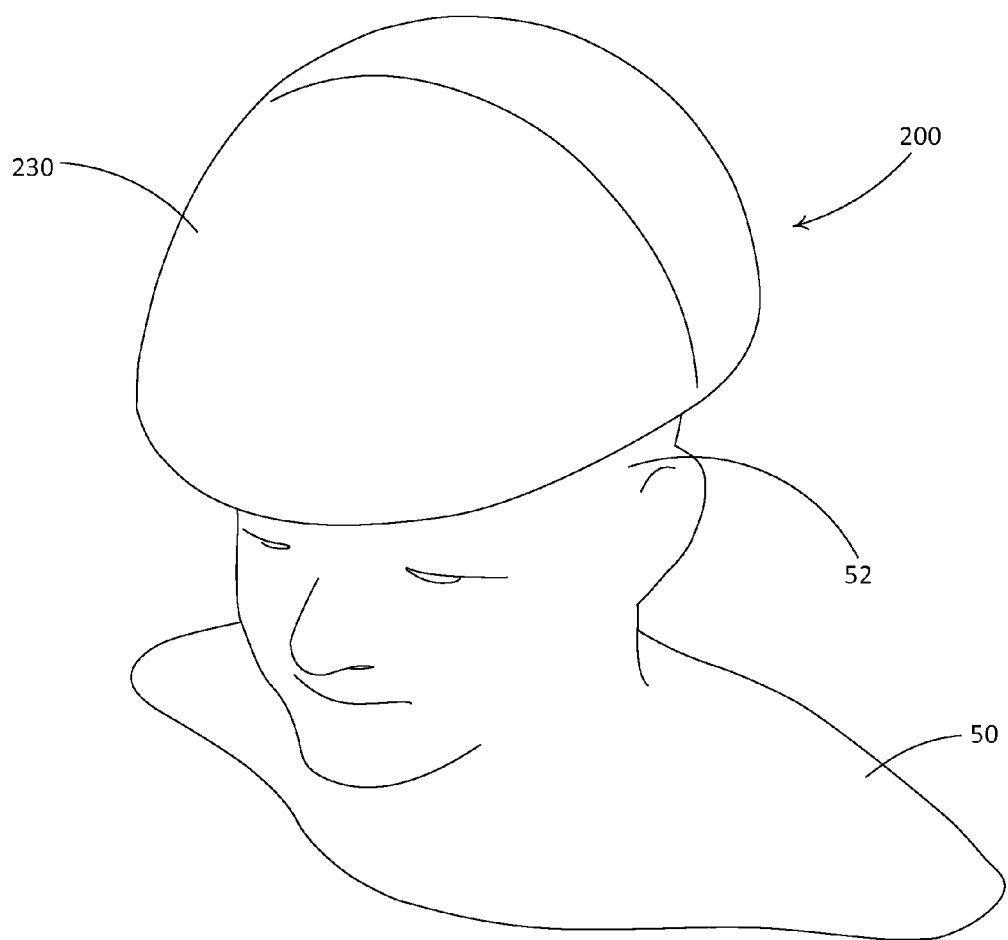
FIG. 2A depicts another example TMS device.
Figure 2B:
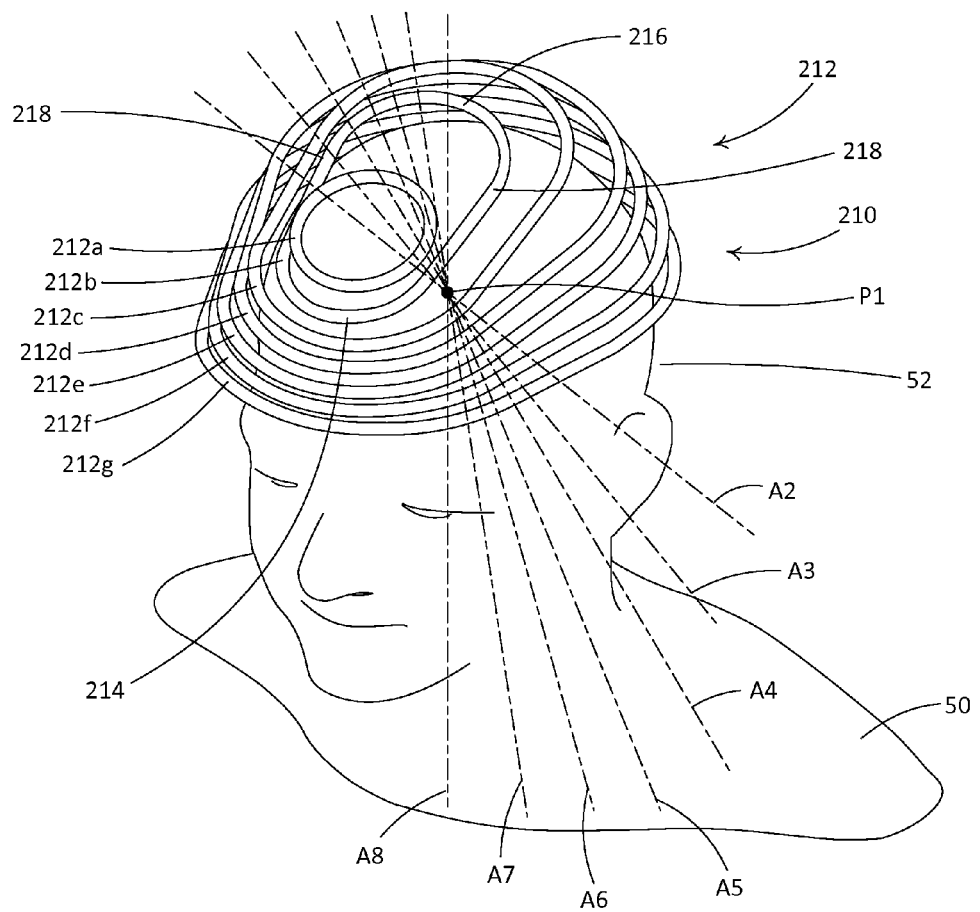
FIG. 2B depicts components of the TMS device of FIG. 2A.

FIGS. 2A and 2B depict a human subject 50 and an example TMS device 200 that is configured to generate a changing magnetic field in a target anatomy of the subject 50. The subject 50 may be, for example, a TMS patient. The target anatomy of the subject 50 may be, for example, brain tissue of the subject 50.

As shown, the TMS device 200 includes a treatment coil 210 and a ferromagnetic component 230. The TMS device 200 may be disposed proximate to the head 52 of the subject 50 in preparation for or during TMS treatment, for example as shown in FIG. 2A.

The treatment coil 210 may include one or more windings 212, such as a plurality of windings 212. As shown, the treatment coil 210 has a plurality of windings 212 that includes seven windings 212a-212g. It should be appreciated that the treatment coil 210 may include more or fewer windings 212.

The treatment coil 210 may be fabricated from a monolithic piece of material. For example, a length of material (e.g., wire) may be continuously wound so as to define the plurality of windings 212. The windings 212, for example one or more of the windings 212a-212g, may be separately fabricated and supported relative to each other, for example attached to each other using one or more attachment members (not shown). A plurality of windings 212 that are separately fabricated may be placed in electrical communication with one another, for example using one or more electrically conductive attachment members that interconnect respective ones of the windings 212.

The windings 212 may define any suitable shapes, for example the illustrated circular and/or semi-elliptical shapes. As shown, the winding 212a has a circular shape and each of the windings 212b-212g defines an arc-shaped front segment 214 that may be disposed proximate the front of the subject's head 52, an opposed arc-shaped rear segment 216 that may be disposed proximate the rear of the subject's head 52, and opposed side segments 218 that connect corresponding ends of the front and rear segments 214, 216, respectively, and that may be disposed along corresponding sides of the subject's head 52. The side segments 218 may be substantially straight (e.g., straight or slightly curved). The front, rear, and/or side segments 214, 216, 218 may be configured to conform to corresponding portions of the subject's head 52. As shown, the rear segment 216 of each of the windings 212b-212g is longer than the corresponding front segment 214, such that each of the windings 212b-212g is tapered along a direction from the rear segment 216 toward the front segment 214.

Each winding 212 may define a respective length, for example as defined by a perimeter of the winding 212 and measured along a central axis through the winding 212. Respective ones of the plurality of windings 212 may have the same or different lengths. Each winding 212 may define any suitable cross-section along its length (e.g., perpendicular to its central axis), such as circular. The treatment coil 210, including one or more of the windings 212a-212g, may be made of any material that exhibits suitable electrical conductivity, such as copper.

Respective ones of the windings 212 may have the same or different shapes. As shown, an uppermost winding 212a has a circular shape that differs from the windings 212b-212g. The winding 212a has a shorter length than the windings 212b-212g. The windings 212b-212g have substantially the same shape relative to one another, but exhibit sequentially increasing lengths from the winding 212b to a lowermost winding 212g. Stated differently, the winding 212b may have a first length, the winding 212c may define a profile that is the same as or similar to that of the winding 212b, and may have a second length that is longer than the first length, the winding 212d may define a profile that is the same as or similar to those of the windings 212b and 212c, and may have a third length that is longer than the second length, and so on. The uppermost winding 212a may be referred to as an innermost winding of the plurality of windings 212, and the lowermost winding 212g may be referred to as an outermost winding of the plurality of windings 212.

The windings 212a-112g may be configured such that a spacing from winding to winding (e.g., between adjacent windings 212) remains uniform or varies. For example, the spacing between the windings 212a-212g may be defined by the respective lengths, shapes, positioning etc., of the windings 212a-212g. As shown, the windings 212a-212g may be centered on respective axes A2-A8 that extend through the subject's head 52 and that are angularly offset relative to each other, such that the respective front segments 214 of the windings 212 may be spaced closer together than the respective rear segments 216. Stated differently, the windings 212a-212g may be spaced further apart from each other at the back of the subject's head 52 than at the front of the subject's head 52. The axes A2-A8 may pass through a common point P1 in the subject's head 52 (e.g., a medially located point). The respective angular offsets between adjacent ones of the axes A2-A8 may be the same or different.

The treatment coil 210 may be configured to define a coil geometry that conforms to a region of the subject's head 52. For example, two or more of the windings 212a-212g may be spaced from each other vertically such that the coil geometry of the treatment coil 210 may be concave with respect to the subject's head 52. As shown, the treatment coil 210 defines an ovoid, dome-shaped coil geometry that encircles an upper region of the subject's head 52.

The TMS device 200 may include a ferromagnetic component 230. The ferromagnetic component 230 may be configured to change one or more characteristics of a magnetic field that is generated by the treatment coil 210. As shown, the ferromagnetic component 230 may be located proximate to the treatment coil 210. The ferromagnetic component 230 may be made of any material that exhibits suitable ferromagnetic properties, such as powdered ferromagnetic iron particles.

The ferromagnetic component 230 may define any suitable shape, for example the illustrated ovoid dome shape. The ferromagnetic component 230 may define an interior volume that is shaped to at least partially conform to a corresponding portion of the subject's head 52. The interior volume of the ferromagnetic component 230 may have proportions that are substantially similar to (e.g., slightly larger than) those of a corresponding portion of the subject's head 52. The ferromagnetic component 230 may define an inner surface (not shown) that faces the subject's head 52 and that is configured to at least partially conform to corresponding portions of the treatment coil 210a and/or to a corresponding portion of the subject's head 52. The inner surface may define the interior volume of the ferromagnetic component 230.

The ferromagnetic component 230 may be configured to at least partially receive the treatment coil 210, such that the ferromagnetic component 230 is positioned proximate to a portion of the treatment coil 210. For example, the ferromagnetic component 230 may define a recess (not shown) that extends into the inner surface of the ferromagnetic component 230. The recess may be configured to receive one or more of the plurality of windings 212. When the treatment coil 210 is disposed in the recess, for example as shown in FIG. 2A, the ferromagnetic component 230 may at least partially surround respective portions of the plurality of windings 212. Portions of the ferromagnetic component 230, for example that define the recess, may have a shape that is similar to (e.g., effectively the same as) one or more corresponding windings 212.

The TMS device 200 may be configured such that the treatment coil 210 and the ferromagnetic component 230 are supported relative to each other. For example, the TMS device 200 may be configured such that the ferromagnetic component 230 supports the treatment coil 210 (e.g., in the recess). One or both of the treatment coil 210 and the ferromagnetic component 230 may include one or more complementary attachment members (not shown) that are configured to enable attachment (e.g., releasable attachment) of the treatment coil 210 to the ferromagnetic component 230. The one or more attachment members may be configured such that the treatment coil 210 and the ferromagnetic component 230 are fixedly supported relative to each other (e.g., in the configuration depicted in FIGS. 2A and 2B). The one or more attachment members may be configured such that the treatment coil 210 and the ferromagnetic component 230 are movable (e.g., repositionable) relative to each other.

When the treatment coil 210 is supported by (e.g., attached to) the ferromagnetic component 230, the treatment coil 210 may be electrically isolated from the ferromagnetic component 230, for example using a dielectric. The dielectric may be air, and the plurality of windings 212 may be spaced from the inner surface of the ferromagnetic component 230 when the treatment coil 210 is attached to the ferromagnetic component 230. The treatment coil 210 may be attached to the ferromagnetic component 230 using one or more attachment members that are made of any suitable electrically isolating (e.g., dielectric) material. As depicted in FIG. 2A, when the treatment coil 210 is received in the ferromagnetic component 230, the treatment coil 210 may be at least partially enclosed by the ferromagnetic component 230.

The TMS device 200, for example as configured and oriented relative to a subject as depicted in FIG. 2A, may be operated to cause the generation of a magnetic field in the subject's brain that may exhibit greater intensity in a frontal region of the subject's brain than in a dorsal region of the subject's brain, for example if the TMS device 200 is positioned relative to a subject as depicted in FIGS. 2A and 2B. When the TMS device 200 is oriented relative to the subject 50 as shown, the magnetic field may be distributed so as to be simultaneously resident in both the first and second hemispheres of the subject's brain.

When the TMS device 200 is oriented as depicted in FIG. 2A, the treatment coil 210 may define current return paths that are close to the subject's head 52. This may assist with the driving of the return currents, and may improve the efficiency of the TMS device 200. The illustrated treatment coil 210 may spread induced return currents generated by the TMS device 200, for example spreading the return currents in the subject's head 52. Spreading the induced return currents may reduce side effects of TMS treatment, such as the stimulation of untargeted regions of the subject's brain. For example, the treatment coil 210 may move the return currents to reduce exposure of the parietal lobe of the subject's brain to the return currents. This may be accomplished, for example, by configuring the treatment coil 210 such that the bulk of the return currents are moved into the occipital lobe, or such that the bulk of the return currents are spread across the parietal lobe and the occipital lobe.

It should be appreciated that the TMS device 200 is not limited to the illustrated orientation relative to a subject (e.g., to the head 52 of the subject 50), and that the TMS device 200 may be differently oriented relative to the subject, such that the portion of the magnetic field that exhibits greater intensity is localized in a different location of the subject's anatomy (e.g., a different location in the subject's brain).

Figure 3A:
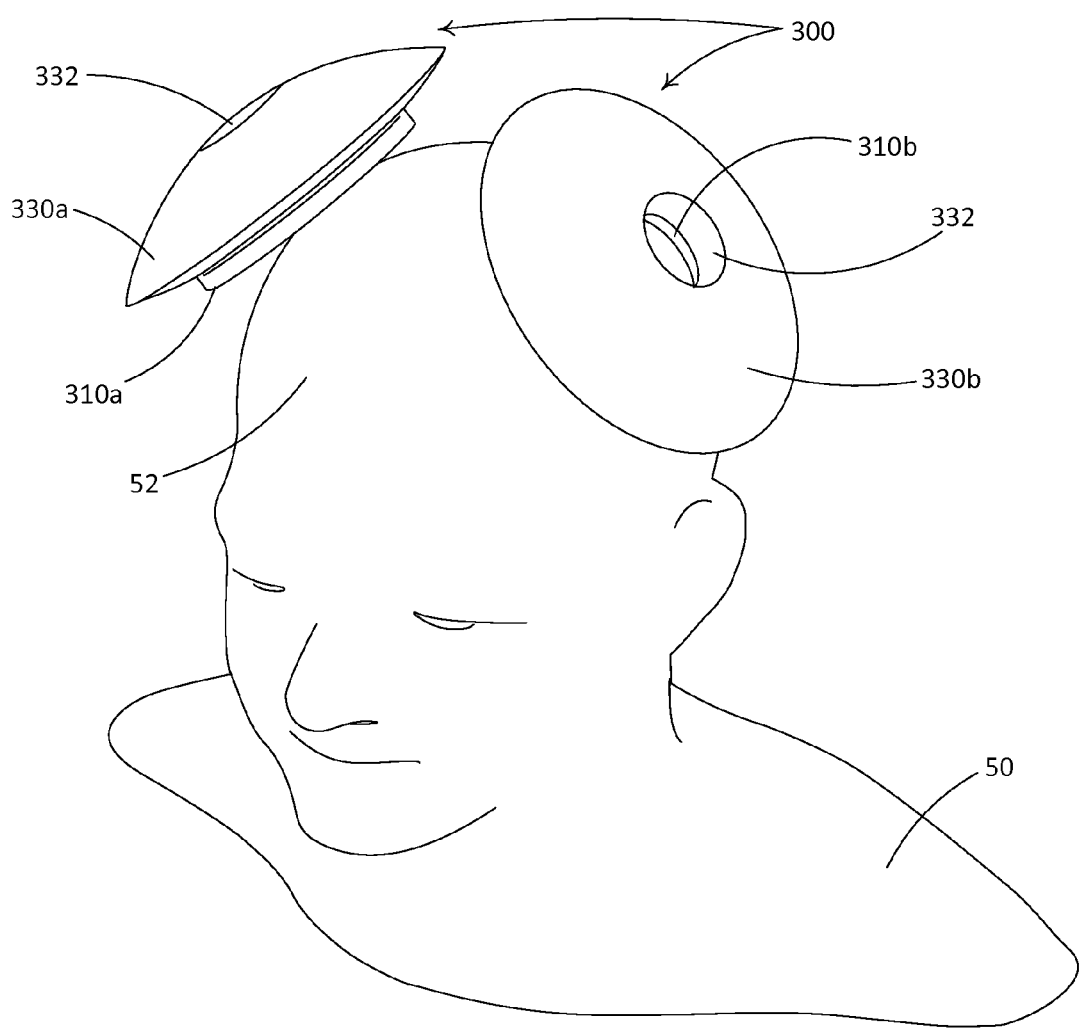
FIG. 3A depicts another example TMS device.
Figure 3B:
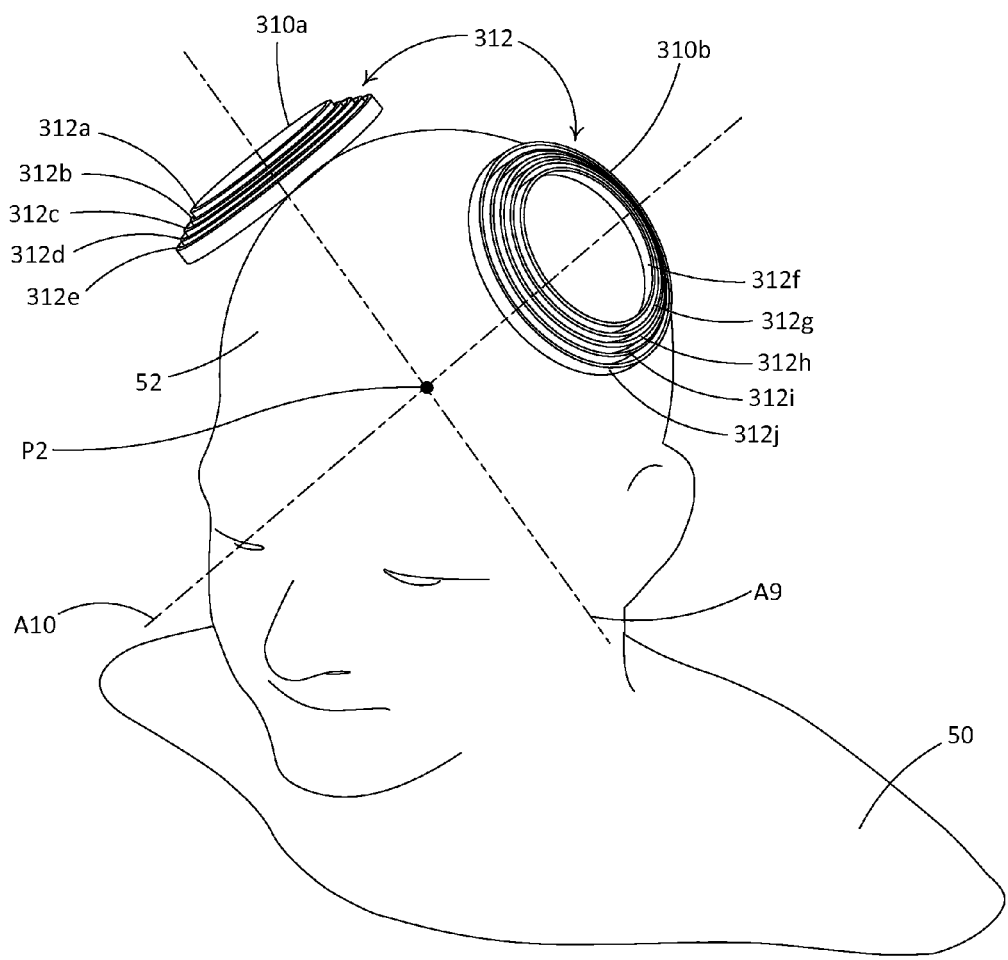
FIG. 3B depicts components of the TMS device of FIG. 3A.

FIGS. 3A and 3B depict a human subject 50 and an example TMS device 300 that is configured to generate a changing magnetic field in a target anatomy of the subject 50. The subject 50 may be, for example, a TMS patient. The target anatomy of the subject 50 may be, for example, brain tissue of the subject 50.

As shown, the TMS device 300 includes a first treatment coil 310a, a second treatment coil 310b, a first ferromagnetic component 330a, and a second ferromagnetic component 330b. The TMS device 300 may be disposed proximate to the head 52 of the subject 50 in preparation for or during TMS treatment, for example as shown in FIG. 3A.

The first and second treatment coils 310a, 310b may each include one or more windings 312, such as respective pluralities of windings 312. The first and second treatment coils 310a, 310b may include the same or different numbers of windings 312. As shown, the first treatment coil 310a includes a first plurality of windings 312 that includes five windings 312a-312e, and the second treatment coil 310b includes a second plurality of windings 312 that includes five windings 312f-312j. It should be appreciated that one or both of the first and second treatment coils 310a, 310b may include more or fewer windings 312, and/or may include windings 312 having the same or different geometries, radial spacing, and so on.

One or both of the first and second treatment coils 310a, 310b may be fabricated from respective monolithic pieces of material. For example, a first length of material (e.g., a metal strip) may be continuously wound so as to define the first plurality of windings 312 that correspond to the first treatment coil 310a and a second length of material (e.g., a metal strip) may be continuously wound so as to define the second plurality of windings 312 that correspond to the second treatment coil 310b. The windings 312, for example one or more of the windings 312a-312j, may be separately fabricated and supported relative to each other, for example attached to each other using one or more attachment members (not shown). A plurality of windings 312 that are separately fabricated may be placed in electrical communication with one another, for example using one or more electrically conductive attachment members that interconnect respective ones of the plurality of windings 312.

Each winding 312 may define a respective length, for example as defined by a perimeter of the winding 312 and measured along a central axis through the winding 312. Respective ones of the first and/or second pluralities of windings 312 may have the same or different lengths. Each winding 312 may define any suitable cross-section along its length (e.g., perpendicular to its central axis), such as rectangular. One or both of the first and second treatment coils 310a, 310b, including one or more of the windings 312a-312e and 312f-312j, respectively, may be made of any material that exhibits suitable electrical conductivity, such as copper.

The windings 312 may define any suitable shapes, for example the illustrated circular shapes. Respective ones of the windings 312 may have the same or different shapes. As shown, the windings 312a-312e of the first treatment coil 310a have substantially the same circular shape relative to one another, but exhibit sequentially increasing lengths from an uppermost winding 312a to a lowermost winding 312e. The uppermost winding 312a may be referred to as an innermost winding of the first treatment coil 310a and the lowermost winding 312e may be referred to as an outermost winding of the first treatment coil 310a. The second treatment coil 310b may be constructed the same as the first treatment coil 310a, such that the windings 312f-312j exhibit sequentially increasing lengths from an uppermost winding 312f to a lowermost winding 312j. The uppermost winding 312f may be referred to as an innermost winding of the second treatment coil 310b and the lowermost winding 312j may be referred to as an outermost winding of the second treatment coil 310b.

The windings 312a-312e of the first treatment coil 310a and/or the windings 312f-312j of the second treatment coil 310b may be configured such that a spacing from winding to winding (e.g., between adjacent windings 312) remains uniform or varies. For example, the spacing between the windings 312a-312e and/or the spacing between the windings 312f-312j may be defined by the respective lengths, shapes, positioning, etc., of the windings 312a-312j. As shown, the windings 312a-312e of the first treatment coil 310a are centered on an axis A9 that extends through the subject's head 52. The windings 312f-312j of the second treatment coil 310b are centered on an axis A10 that extends through the subject's head 52 and that is angularly offset relative to the first axis A9. The axes A9 and A10 may pass through a common point P2 in the subject's head 52 (e.g., a medially located point).

One or both of the first and second treatment coils 310a, 310b may be configured to define coil geometries that conform to respective regions of the subject's head 52. For example, two or more of the windings 312a-312e of the first treatment coil 310a may be spaced from each other vertically such that the coil geometry of the first treatment coil 310a may be concave with respect to the subject's head 52. Two or more of the windings 312f-312j of the second treatment coil 310b may be spaced from each other vertically such that the coil geometry of the second treatment coil 310b may be concave with respect to the subject's head 52.

As shown, the first and second treatment coils 310a, 310b define respective concave, saucer-shaped coil geometries that encircle respective portions of the subject's head 52.

The TMS device 300 may include a first ferromagnetic component 330a that corresponds to the first treatment coil 310a and a second ferromagnetic component 330b that corresponds to the second treatment coil 310b. The first and second ferromagnetic components 330a, 330b may be configured to change one or more characteristics of a magnetic field that is generated by the first and second treatment coils 310a, 310b. As shown, the first ferromagnetic component 330a may be located proximate to the first treatment coil 310a and the second ferromagnetic component 330b may be located proximate to the second treatment coil 310b. The first and second ferromagnetic components 330a, 330b may be made of any material that exhibits suitable ferromagnetic properties, such as powdered ferromagnetic iron particles.

The first and second ferromagnetic components 330a, 330b may define any suitable shapes, and may have the same or different shapes. As shown, the first and second ferromagnetic components 330a, 330b have saucer-like shapes. One or both of the first and second ferromagnetic components 330a, 330b may define respective inner surfaces (not shown) that face the subject's head 52 and that may be configured to at least partially conform to corresponding portions of the first and second treatment coils 310a, 310b, respectively and/or to corresponding portions of the subject's head 52.

The first ferromagnetic component 330a may be configured to at least partially receive the first treatment coil 310a, such that the first ferromagnetic component 330a is positioned proximate to a portion of the first treatment coil 310a. For example, the inner surface of the first ferromagnetic component 330a may be configured to receive one or more of the windings 312a-312e. The second ferromagnetic component 330b may be configured to at least partially receive the second treatment coil 310b, such that the second ferromagnetic component 330b is positioned proximate to a portion of the second treatment coil 310b. For example, the inner surface of the second ferromagnetic component 330b may be configured to receive one or more of the windings 312f-312j.

When the first treatment coil 310a is disposed proximate the inner surface of the first ferromagnetic component 330a, for example as shown in FIG. 3A, the first ferromagnetic component 330a may at least partially surround respective portions of the first plurality of windings 312. When the second treatment coil 310b is disposed proximate the inner surface of the second ferromagnetic component 330b, for example as shown in FIG. 3A, the second ferromagnetic component 330b may at least partially surround respective portions of the second plurality of windings 312. Respective portions of the first and/or second ferromagnetic components 330a, 330b may have a shape that is similar to (e.g., effectively the same as) one or more corresponding windings 312.

The TMS device 300 may be configured such that the first treatment coil 310a and the first ferromagnetic component 330a are supported relative to each other, and such that the second treatment coil 310b and the second ferromagnetic component 330b are supported relative to each other. For example, the TMS device 300 may be configured such that the first ferromagnetic component 330a supports the first treatment coil 310a (e.g., at the inner surface of the first ferromagnetic component 330a), and such that the second ferromagnetic component 330b supports the second treatment coil 310b (e.g., at the inner surface of the second ferromagnetic component 330*b*). The first treatment coil 310*a* and the first ferromagnetic component 330*a* may include one or more complementary attachment members (not shown) that are configured to enable attachment (e.g., releasable attachment) of the first treatment coil 310*a* to the first ferromagnetic component 330*a*, and the second treatment coil 310*b* and the second ferromagnetic component 330*b* may include one or more complementary attachment members (not shown) that are configured to enable attachment (e.g., releasable attachment) of the second treatment coil 310*b* to the second ferromagnetic component 330*b*.

When the first treatment coil 310*a* is supported by (e.g., attached to) the first ferromagnetic component 330*a*, the first treatment coil 310*a* may be electrically isolated from the first ferromagnetic component 330*a*, for example using a dielectric. The dielectric may be air, and the first plurality of windings 312 may be spaced from the inner surface of the first ferromagnetic component 330*a* when the first treatment coil 310*a* is attached to the first ferromagnetic component 330*a* (e.g., to the inner surface of the first ferromagnetic component 330*a*). The first treatment coil 310*a* may be attached to the first ferromagnetic component 330*a* using one or more attachment members that are made of any suitable electrically isolating (e.g., dielectric) material. As depicted in FIG. 3A, when the first treatment coil 310*a* is received in the first ferromagnetic component 330*a*, the first treatment coil 310*a* may be at least partially enclosed by the first ferromagnetic component 330*a*.

When the second treatment coil 310*b* is supported by (e.g., attached to) the second ferromagnetic component 330*b*, the second treatment coil 310*b* may be electrically isolated from the second ferromagnetic component 330*b*, for example using a dielectric. The dielectric may be air, and the second plurality of windings 312 may be spaced from the inner surface of the second ferromagnetic component 330*b* when the second treatment coil 310*b* is attached to the second ferromagnetic component 330*b* (e.g., to the inner surface of the second ferromagnetic component 330*b*). The second treatment coil 310*b* may be attached to the second ferromagnetic component 330*b* using one or more attachment members that are made of any suitable electrically isolating (e.g., dielectric) material. As depicted in FIG. 3A, when the second treatment coil 310*b* is received in the second ferromagnetic component 330*b*, the second treatment coil 310*b* may be at least partially enclosed by the second ferromagnetic component 330*b*.

The first ferromagnetic component 330*a* may define one or more openings 332 that may expose corresponding portions of the subject's head 52, for example to promote cooling during TMS treatment. The second ferromagnetic component 330*b* may define one or more openings 332 that may expose corresponding portions of the subject's head 52, for example to promote cooling during TMS treatment. As shown, the first ferromagnetic component 330*a* defines an opening 332 at an upper end thereof that extends therethrough and the second ferromagnetic component 330*b* defines an opening 332 at an upper end thereof that extends therethrough. It should be appreciated that the one or both of the first and second ferromagnetic components 330*a*, 330*b* may be configured to define more or fewer openings. For example, one or both of the first and second ferromagnetic components 330*a*, 330*b* may be configured to define a plurality of openings therethrough, or may be configured with no opening therethrough.

The first and second ferromagnetic components 330*a*, 330*b* may be supported relative to each other. For example, a bridge member (not shown) may be used to support the first and second ferromagnetic components 330*a*, 330*b* relative to each other. Such a bridge member may, for example, have a first end that is attached (e.g., releasably) to the first ferromagnetic component 330*a* and an opposed second end that is attached (e.g., releasably) to the second ferromagnetic component 330*b*. The bridge member may be configured to enable adjustment of the TMS device 300, for example to adjust positioning of the first and/or second treatment coils 310*a*, 310*b* relative to the subject's head 52. The first end of the bridge member may be fixedly or movably (e.g., rotatably) attached to the first ferromagnetic component 330*a*. The second end of the bridge member may be fixedly or movably (e.g., rotatably) attached to the second ferromagnetic component 330*b*.

The bridge member may be configured to be adjustable between the first and second ends. For example, the bridge member may include a first portion that is attached to the first ferromagnetic component 330*a* and a second portion that is attached to the second ferromagnetic component 330*b*. The first and second portions of the bridge member may be configured to slide past each other, such that the TMS device 300 may be adjusted (e.g., relative to subject anatomy) by sliding the first and second portions of the bridge member relative to each other. The bridge member may include first and second portions that are angularly movable relative to each other (e.g., about a pivot or joint), such that the TMS device 300 may be adjusted (e.g., relative to subject anatomy).

The TMS device 300, for example as configured and oriented relative to a subject as depicted in FIG. 3A, may be operated to cause the generation of a magnetic field in the subject's brain that may exhibit greater intensity in a region located between the first and second treatment coils 310*a*, 310*b*, for example in an upper region of the subject's brain, than in other regions of the subject's brain. When the TMS device 300 is oriented relative to the subject 50 as shown, the magnetic field may be distributed so as to be simultaneously resident in both the first and second hemispheres of the subject's brain.

It should be appreciated that the TMS device 300 is not limited to the illustrated orientation relative to a subject (e.g., to the head 52 of the subject 50), and that the TMS device 300 may be differently oriented relative to the subject, such that the portion of the magnetic field that exhibits greater intensity is localized in a different location of the subject's anatomy (e.g., a different location in the subject's brain).

The current distribution in the first and second treatment coils 310*a*, 310*b* may be the same or different. For example, if the current delivered to one of the first or second treatment coils 310*a*, 310*b* is spread out over a larger area (e.g., via longer windings 312, greater winding density, etc.), one or more characteristics (e.g., focality, penetration depth, etc.) of the magnetic field generated by the TMS device 300 may be altered.

Additionally, one or more characteristics of the magnetic field generated by the TMS device 300 may be altered by adjusting the spacing of the first and second ferromagnetic components 330*a*, 330*b* relative to each other (e.g., using an adjustable bridging member). For example, if the first and second ferromagnetic components 330*a*, 330*b* are moved closer to each other (e.g., closer to the top of the subject's head), the resulting magnetic field generated by the TMS device 300 may exhibit more focality, and may exhibit decreased penetration depth. If the first and second ferromagnetic components 330*a*, 330*b* are moved further each other (e.g., away from the top of the subject's head), the resulting magnetic field generated by the TMS device 300 may exhibit less focality, and may exhibit increased penetration depth. Furthermore, if the radial spacing between one or more of the respective windings 312 of the first and/or second treatment coils 310a, 310b is increased, the resulting magnetic field generated by the TMS device 300 may exhibit increased penetration depth.

Figure 4A:
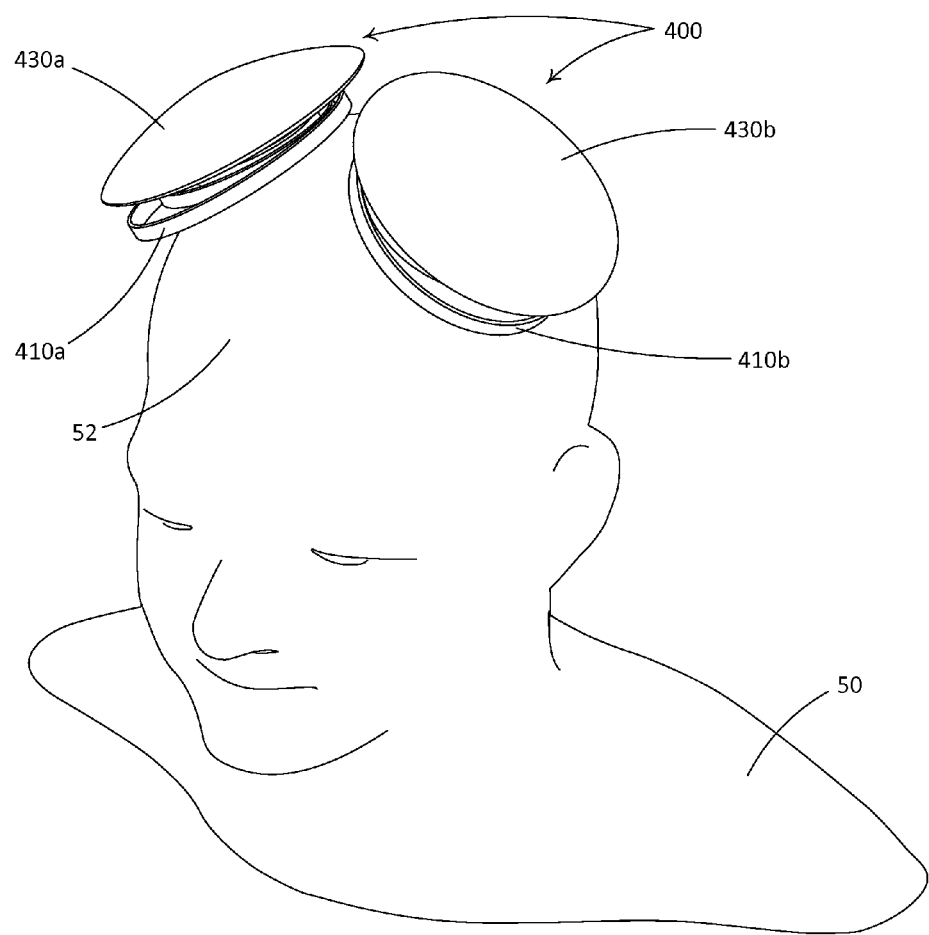
FIG. 4A depicts another example TMS device.
Figure 4B:
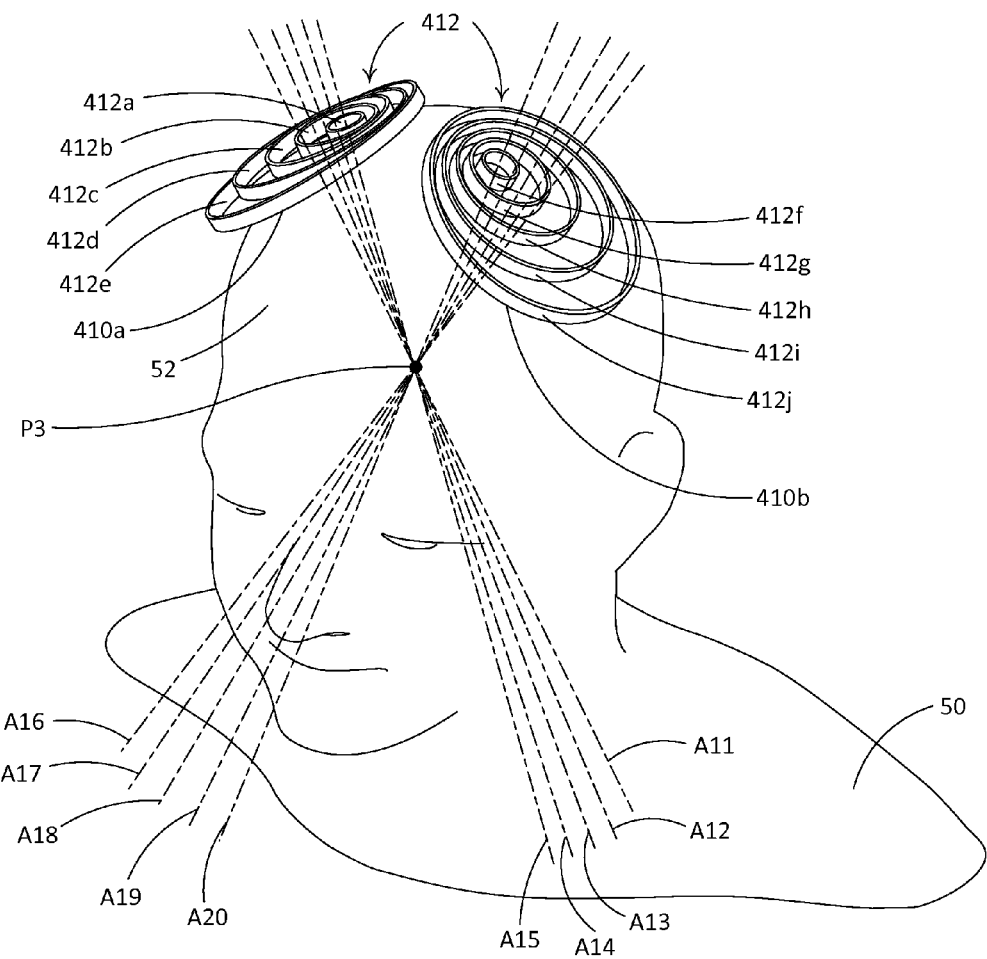
FIG. 4B depicts components of the TMS device of FIG. 4A.

FIGS. 4A and 4B depict a human subject 50 and an example TMS device 400 that is configured to generate a changing magnetic field in a target anatomy of the subject 50. The subject 50 may be, for example, a TMS patient. The target anatomy of the subject 50 may be, for example, brain tissue of the subject 50.

As shown, the TMS device 400 includes a first treatment coil 410a, a second treatment coil 410b, a first ferromagnetic component 430a, and a second ferromagnetic component 430b. The TMS device 400 may be disposed proximate to the head 52 of the subject 50 in preparation for or during TMS treatment, for example as shown in FIG. 4A.

The first and second treatment coils 410a, 410b may each include one or more windings 412, such as respective pluralities of windings 412. The first and second treatment coils 410a, 410b may include the same or different numbers of windings 412. As shown, the first treatment coil 410a includes a first plurality of windings 412 that includes five windings 412a-412e and the second treatment coil 410b includes a second plurality of windings 412 that includes five windings 412f-412j. It should be appreciated that one or both of the first and second treatment coils 410a, 410b may include more or fewer windings 412, and/or may include windings 412 having the same or different geometries, radial spacing, and so on.

One or both of the first and second treatment coils 410a, 410b may be fabricated from respective monolithic pieces of material. For example, a first length of material (e.g., a metal strip) may be continuously wound so as to define the first plurality of windings 412 that correspond to the first treatment coil 410a and a second length of material (e.g., a metal strip) may be continuously wound so as to define the second plurality of windings 412 that correspond to the second treatment coil 410b. The windings 412, for example one or more of the windings 412a-412j, may be separately fabricated and supported relative to each other, for example attached to each other using one or more attachment members (not shown). A plurality of windings 412 that are separately fabricated may be placed in electrical communication with one another, for example using one or more electrically conductive attachment members that interconnect respective ones of the plurality of windings 412.

Each winding 412 may define a respective length, for example as defined by a perimeter of the winding 412 and measured along a central axis through the winding 412. Respective ones of the first and/or second pluralities of windings 412 may have the same or different lengths. Each winding 412 may define any suitable cross-section along its length (e.g., perpendicular to its central axis), such as rectangular. One or both of the first and second treatment coils 410a, 410b, including one or more of the windings 412a-412e and 412f-412j, respectively, may be made of any material that exhibits suitable electrical conductivity, such as copper.

The windings 412 may define any suitable shapes, for example the illustrated circular shapes. Respective ones of the windings 412 may have the same or different shapes. As shown, the windings 412a-412e of the first treatment coil 410a have substantially the same circular shape relative to one another, but exhibit sequentially increasing lengths from an uppermost winding 412a to a lowermost winding 412e. The uppermost winding 412a may be referred to as an innermost winding of the first treatment coil 410a and the lowermost winding 412e may be referred to as an outermost winding of the first treatment coil 410a. The second treatment coil 410b may be constructed the same as the first treatment coil 410a, such that the windings 412f-412j exhibit sequentially increasing lengths from an uppermost winding 412f to a lowermost winding 412j. The uppermost winding 412f may be referred to as an innermost winding of the second treatment coil 410b and the lowermost winding 412j may be referred to as an outermost winding of the second treatment coil 410b.

The windings 412a-412e of the first treatment coil 410a and/or the windings 412f-412j of the second treatment coil 410b may be configured such that a spacing from winding to winding (e.g., between adjacent windings 412) remains uniform or varies. For example, the spacing between the windings 412a-412e and/or the spacing between the windings 412f-412j may be defined by the respective lengths, shapes, positioning, etc., of the windings 412a-412j. As shown, the windings 412a-412e of the first treatment coil 410a may be centered on respective axes A11-A15 that extend through the subject's head 52 and that are angularly offset relative to each other, such that the windings 412a-412e may be spaced closest together to each other on one side of the first treatment coil 410a and furthest apart from each other on an opposed side of the first treatment coil 410a. The windings 412f-412j of the second treatment coil 410b may be centered on respective axes A16-A20 that extend through the subject's head 52 and that are angularly offset relative to each other, such that the windings 412f-412j may be spaced closest together to each other on one side of the second treatment coil 410b and furthest apart from each other on an opposed side of the second treatment coil 410b.

The axes A11-A20 may pass through a common point P3 in the subject's head 52 (e.g., a medially located point). The respective angular offsets between adjacent ones of the axes A11-15 may be the same or different and the respective angular offsets between adjacent ones of the axes A16-A20 may be the same or different. The respective angular offsets between adjacent ones of the axes A11-15 may correspond with the respective angular offsets between adjacent ones of the axes A16-20.

One or both of the first and second treatment coils 410a, 410b may be configured to define coil geometries that conform to respective regions of the subject's head 52. For example, two or more of the windings 412a-412e of the first treatment coil 410a may be spaced from each other vertically such that the coil geometry of the first treatment coil 410a may be concave with respect to the subject's head 52. Two or more of the windings 412f-412j of the second treatment coil 410b may be spaced from each other vertically such that the coil geometry of the second treatment coil 410b may be concave with respect to the subject's head 52. As shown, the first and second treatment coils 410a, 410b define respective concave, saucer-shaped coil geometries that encircle respective portions of the subject's head 52.

The TMS device 400 may include a first ferromagnetic component 430a that corresponds to the first treatment coil 410a and a second ferromagnetic component 430b that corresponds to the second treatment coil 410b. The first and second ferromagnetic components 430a, 430b may be configured to change one or more characteristics of a magnetic field that is generated by the first and second treatment coils 410a, 410b. As shown, the first ferromagnetic component 430a may be located proximate to the first treatment coil 410a and the second ferromagnetic component 430b may be located proximate to the second treatment coil 410b. The first and second ferromagnetic components 430a, 430b may be made of any material that exhibits suitable ferromagnetic properties, such as powdered ferromagnetic iron particles.

The first and second ferromagnetic components 430a, 430b may define any suitable shapes, and may have the same or different shapes. As shown, the first and second ferromagnetic components 430a, 430b have saucer-like shapes. One or both of the first and second ferromagnetic components 430a, 430b may define respective inner surfaces (not shown) that face the subject's head 52 and that may be configured to at least partially conform to corresponding portions of the first and second treatment coils 410a, 410b, respectively and/or to corresponding portions of the subject's head 52.

The first ferromagnetic component 430a may be configured to at least partially receive the first treatment coil 410a, such that the first ferromagnetic component 430a is positioned proximate to a portion of the first treatment coil 410a. For example, the inner surface of the first ferromagnetic component 430a may be configured to receive one or more of the windings 412a-412e. The second ferromagnetic component 430b may be configured to at least partially receive the second treatment coil 410b, such that the second ferromagnetic component 430b is positioned proximate to a portion of the second treatment coil 410b. For example, the inner surface of the second ferromagnetic component 430b may be configured to receive one or more of the windings 412f-412j.

When the first treatment coil 410a is disposed proximate the inner surface of the first ferromagnetic component 430a, for example as shown in FIG. 4A, the first ferromagnetic component 430a may at least partially surround respective portions of the first plurality of windings 412. When the second treatment coil 410b is disposed proximate the inner surface of the second ferromagnetic component 430b, for example as shown in FIG. 4A, the second ferromagnetic component 430b may at least partially surround respective portions of the second plurality of windings 412. Respective portions of the first and/or second ferromagnetic components 430a, 430b may have a shape that is similar to (e.g., effectively the same as) one or more corresponding windings 412.

The TMS device 400 may be configured such that the first treatment coil 410a and the first ferromagnetic component 430a are supported relative to each other, and such that the second treatment coil 410b and the second ferromagnetic component 430b are supported relative to each other. For example, the TMS device 400 may be configured such that the first ferromagnetic component 430a supports the first treatment coil 410a (e.g., at the inner surface of the first ferromagnetic component 430a), and such that the second ferromagnetic component 430b supports the second treatment coil 410b (e.g., at the inner surface of the second ferromagnetic component 430b). The first treatment coil 410a and the first ferromagnetic component 430a may include one or more complementary attachment members (not shown) that are configured to enable attachment (e.g., releasable attachment) of the first treatment coil 410a to the first ferromagnetic component 430a, and the second treatment coil 410b and the second ferromagnetic component 430b may include one or more complementary attachment members (not shown) that are configured to enable attachment (e.g., releasable attachment) of the second treatment coil 410b to the second ferromagnetic component 430b.

When the first treatment coil 410a is supported by (e.g., attached to) the first ferromagnetic component 430a, the first treatment coil 410a may be electrically isolated from the first ferromagnetic component 430a, for example using a dielectric. The dielectric may be air, and the first plurality of windings 412 may be spaced from the inner surface of the first ferromagnetic component 430a when the first treatment coil 410a is attached to the first ferromagnetic component 430a (e.g., to the inner surface of the first ferromagnetic component 430a). The first treatment coil 410a may be attached to the first ferromagnetic component 430a using one or more attachment members that are made of any suitable electrically isolating (e.g., dielectric) material. As depicted in FIG. 4A, when the first treatment coil 410a is received in the first ferromagnetic component 430a, the first treatment coil 410a may be at least partially enclosed by the first ferromagnetic component 430a.

When the second treatment coil 410b is supported by (e.g., attached to) the second ferromagnetic component 430b, the second treatment coil 410b may be electrically isolated from the second ferromagnetic component 430b, for example using a dielectric. The dielectric may be air, and the second plurality of windings 412 may be spaced from the inner surface of the second ferromagnetic component 430b when the second treatment coil 410b is attached to the second ferromagnetic component 430b (e.g., to the inner surface of the second ferromagnetic component 430b). The second treatment coil 410b may be attached to the second ferromagnetic component 430b using one or more attachment members that are made of any suitable electrically isolating (e.g., dielectric) material. As depicted in FIG. 4A, when the second treatment coil 410b is received in the second ferromagnetic component 430b, the second treatment coil 410b may be at least partially enclosed by the second ferromagnetic component 430b.

The first and second ferromagnetic components 430a, 430b may be supported relative to each other. For example, a bridge member (not shown) may be used to support the first and second ferromagnetic components 430a, 430b relative to each other. Such a bridge member may, for example, have a first end that is attached (e.g., releasably) to the first ferromagnetic component 430a and an opposed second end that is attached (e.g., releasably) to the second ferromagnetic component 430b. The bridge member may be configured to enable adjustment of the TMS device 400, for example to adjust positioning of the first and/or second treatment coils 410a, 410b relative to the subject's head 52. The first end of the bridge member may be fixedly or movably (e.g., rotatably) attached to the first ferromagnetic component 430a. The second end of the bridge member may be fixedly or movably (e.g., rotatably) attached to the second ferromagnetic component 430b.

The bridge member may be adjustable between the first and second ends. For example, the bridge member may include a first portion that is attached to the first ferromagnetic component 430a and a second portion that is attached to the second ferromagnetic component 430b. The first and second portions of the bridge member may be configured to slide past each other, such that the TMS device 400 may be adjusted (e.g., relative to subject anatomy) by sliding the first and second portions of the bridge member relative to each other. The bridge member may include first and second portions that are angularly movable relative to each other (e.g., about a pivot or joint), such that the TMS device 400 may be adjusted (e.g., relative to subject anatomy).

The TMS device 400, for example as configured and oriented relative to a subject as depicted in FIG. 4A, may be operated to cause the generation of a magnetic field in the subject's brain that may exhibit greater intensity in a region located between the first and second treatment coils 410a, 410b, for example in an upper region of the subject's brain, than in other regions of the subject's brain. When the TMS device 400 is oriented relative to the subject 50 as shown, the magnetic field may be distributed so as to be simultaneously resident in both the first and second hemispheres of the subject's brain.

When the TMS device 400 is oriented as depicted in FIG. 4A, the first and second treatment coils 410a, 410b may define current return paths that are close to the subject's head 52. This may assist with the driving of the return currents, and may improve the efficiency of the TMS device 400. The illustrated first and second treatment coils 410a, 410b may spread induced return currents generated by the TMS device 400, for example spreading the return currents in the subject's head 52. Spreading the induced return currents may reduce side effects of TMS treatment, such as the stimulation of untargeted regions of the subject's brain.

It should be appreciated that the TMS device 400 is not limited to the illustrated orientation relative to a subject (e.g., to the head 52 of the subject 50), and that the TMS device 400 may be differently oriented relative to the subject, such that the portion of the magnetic field that exhibits greater intensity is localized in a different location of the subject's anatomy (e.g., a different location in the subject's brain).

The current distribution in the first and second treatment coils 410a, 410b may be the same or different. For example, if the current delivered to one of the first or second treatment coils 410a, 410b is spread out over a larger area (e.g., via longer windings 412, greater winding density, etc.), one or more characteristics (e.g., focality, penetration depth, etc.) of the magnetic field generated by the TMS device 400 may be altered.

Additionally, one or more characteristics of the magnetic field generated by the TMS device 400 may be altered by adjusting the spacing of the first and second ferromagnetic components 430a, 430b relative to each other (e.g., using an adjustable bridging member). For example, if the first and second ferromagnetic components 430a, 430b are moved closer to each other (e.g., closer to the top of the subject's head), the resulting magnetic field generated by the TMS device 400 may exhibit more focality, and may exhibit decreased penetration depth. If the first and second ferromagnetic components 430a, 430b are moved further each other (e.g., away from the top of the subject's head), the resulting magnetic field generated by the TMS device 400 may exhibit less focality, and may exhibit increased penetration depth. Furthermore, if the radial spacing between one or more of the respective windings 412 of the first and/or second treatment coils 410a, 410b is increased, the resulting magnetic field generated by the TMS device 400 may exhibit increased penetration depth.

Figure 5A:
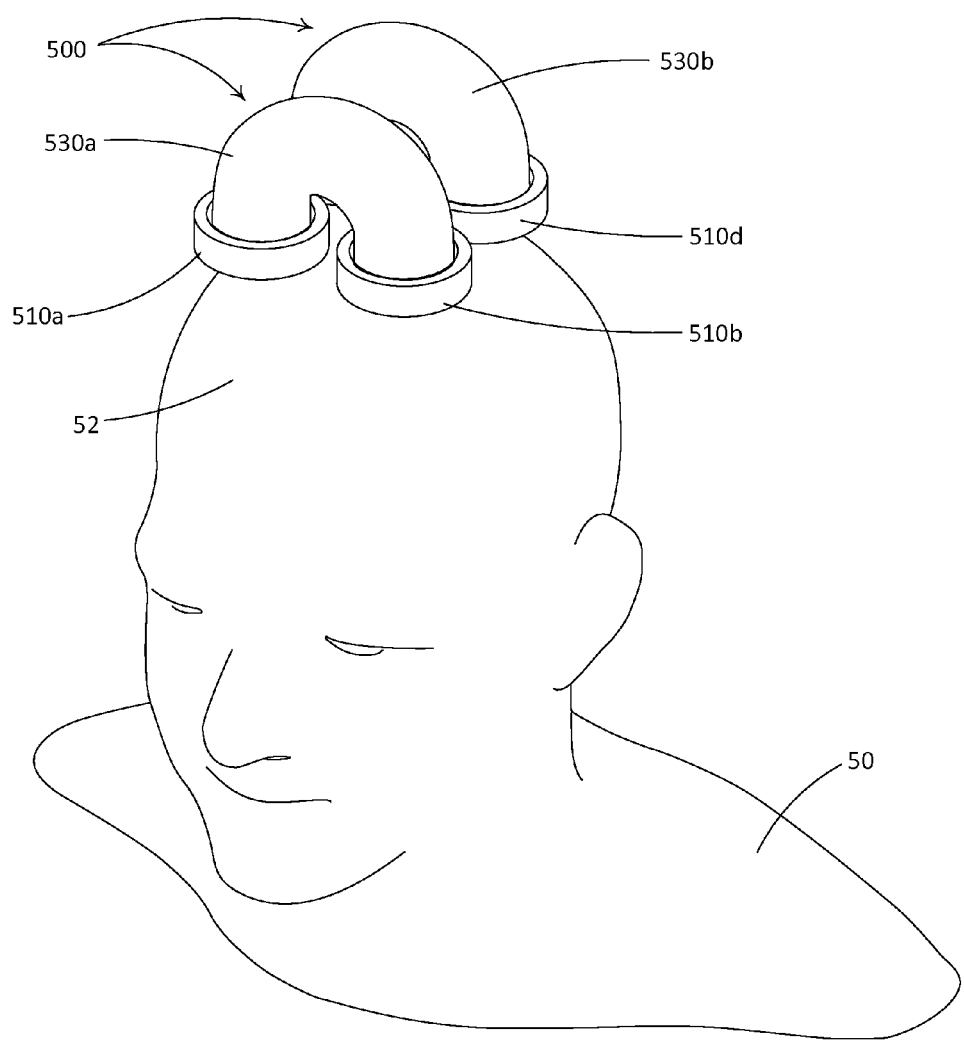
FIG. 5A depicts another example TMS device.
Figure 5B:
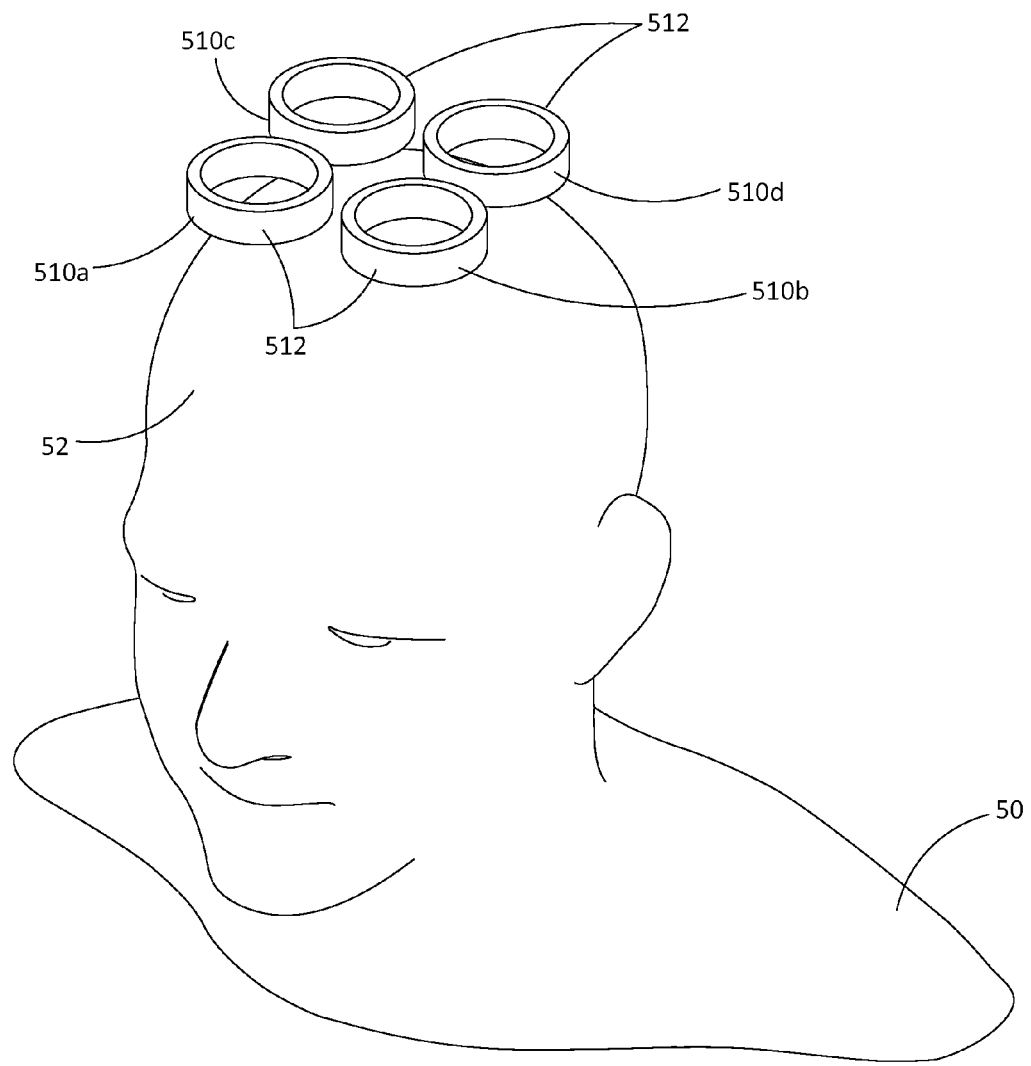
FIG. 5B depicts components of the TMS device of FIG. 5A.

FIGS. 5A and 5B depict a human subject 50 and an example TMS device 500 that is configured to generate a changing magnetic field in a target anatomy of the subject 50. The subject 50 may be, for example, a TMS patient. The target anatomy of the subject 50 may be, for example, brain tissue of the subject 50.

As shown, the TMS device 500 includes a first treatment coil 510a, a second treatment coil 510b, a third treatment coil 510c, a fourth treatment coil 510d, a first ferromagnetic component 530a, and a second ferromagnetic component 530b. The TMS device 500 may be disposed proximate to the head 52 of the subject 50 in preparation for or during TMS treatment, for example as shown in FIG. 5A.

The first, second, third, and fourth treatment coils 510a, 510b, 510c, 510d may each include one or more windings 512, such as respective pluralities of windings 512. The first, second, third, and fourth treatment coils 510a, 510b, 510c, 510d may include the same or different numbers of windings 512. As shown, the first, second, third, and fourth treatment coils 510a, 510b, 510c, 510d each include a single winding 512. Each respective winding 512 may be fabricated from a single turn of material. One or more of the windings 512, for example each of the windings 512, may be fabricated from a plurality of turns of material (e.g., a piece of wire wrapped around a circumference of the winding a number of times). It should be appreciated that one or more of the first, second, third, and fourth treatment coils 510a, 510b, 510c, 510d may include more than one winding 512, for example a plurality of windings 512.

The windings 512 may define any suitable shapes. Respective ones of the windings 512 may have the same or different shapes. As shown, each winding 512 defines substantially the same circular shape. Each winding 512 may define a respective length, for example as defined by a perimeter of the winding 512 and measured along a central axis through the winding 512. The respective windings 512 of the first, second, third, and fourth treatment coils 510a, 510b, 510c, 510d may have the same or different lengths. As shown, the windings 512 of the first, second, third, and fourth treatment coils 510a, 510b, 510c, 510d have the same length. Each winding 512 may define any suitable cross-section along its length (e.g., perpendicular to its central axis), such as rectangular. The windings 512 may be made of any material that exhibits suitable electrical conductivity, such as copper.

The first, second, third, and fourth treatment coils 510a, 510b, 510c, 510d may be oriented relative to the subject's head 52. The first, second, third, and fourth treatment coils 510a, 510b, 510c, 510d may be oriented the same or differently with respect to each other. As shown, the first, second, third, and fourth treatment coils 510a, 510b, 510c, 510d are oriented in a coplanar configuration relative to each other, on a substantially transverse plane with respect to the subject 50.

It should be appreciated that the TMS device 500 may be configured with one or more of the first, second, third, and fourth treatment coils 510a, 510b, 510c, 510d differently oriented relative to each other. The first, second, third, and fourth treatment coils 510a, 510b, 510c, 510d may be oriented differently (e.g., rotated about respective geometric centers) with respect to each other, in order to conform with a region of the subject's head 52. For example, the TMS device 500 may be configured with the second and third treatment coils 510b, 510c rotated ninety degrees about their respective geometric centers, such that the second and third treatment coils 510b, 510c are oriented in a plane that is normal to the plane in which the first and fourth treatment coils 510a, 510d are oriented.

The TMS device 500 may include a first ferromagnetic component 530a that corresponds to the first and second treatment coils 510a, 510b, and a second ferromagnetic component 530b that corresponds to the third and fourth treatment coils 510c, 510d. The first and second ferromagnetic components 530a, 530b may be configured to change one or more characteristics of a magnetic field that is generated by the first, second, third, and fourth treatment coils 510a, 510b, 510c, 510d. As shown, the first ferromagnetic component 530a may be located proximate to the first and second treatment coils 510a, 510b, and the second ferromagnetic component 530b may be located proximate to the third and fourth treatment coils 510c, 510d. The first and second ferromagnetic components 530a, 530b may be made of any material that exhibits suitable ferromagnetic properties, such as powdered ferromagnetic iron particles.

The first and second ferromagnetic components 530a, 530b may define any suitable shapes, and may have the same or different shapes. As shown, the first and second ferromagnetic components 530a, 530b have substantially the same arced, cylindrical shape. The first ferromagnetic component 530a may define a first end that is configured to support the first treatment coil 510a and an opposed second end that is configured to support the second treatment coil 510b. The second ferromagnetic component 530b may define a first end that is configured to support the first treatment coil 510a and an opposed second end that is configured to support the second treatment coil 510b.

The first ferromagnetic component 530a may be configured to support the first and second treatment coils 510a, 510b, such that the first ferromagnetic component 530a is positioned proximate to the first and second treatment coils 510a, 510b. For example, the first treatment coil 510a may be attached to (e.g., wrapped around) the first end of the first ferromagnetic component 530a and the second treatment coil 510b may be attached to (e.g., wrapped around) the second end of the first ferromagnetic component 530a. The second ferromagnetic component 530b may be configured to support the third and fourth treatment coils 510c, 510d, such that the second ferromagnetic component 530b is positioned proximate to the third and fourth treatment coils 510c, 510d. For example, the third treatment coil 510c may be attached to (e.g., wrapped around) the first end of the second ferromagnetic component 530b and the fourth treatment coil 510d may be attached to (e.g., wrapped around) the second end of the second ferromagnetic component 530b.

It should be appreciated that one or both of the first and second ferromagnetic components 530a, 530b may be configured to at least partially enclose respective portions of one or more of the first, second, third, and fourth treatment coils 510a, 510b, 510c, 510d. For example, the first end of the first ferromagnetic component 530a may define a surface configured to at least partially receive the first treatment coil 510a, the second end of the first ferromagnetic component 530a may define a surface configured to at least partially receive the second treatment coil 510b, the first end of the second ferromagnetic component 530b may define a surface configured to at least partially receive the third treatment coil 510c, and/or the second end of the second ferromagnetic component 530b may define a surface configured to at least partially receive the fourth treatment coil 510d. The first, second, third, and fourth treatment coils 510a, 510b, 510c, 510d and the first and second ferromagnetic components 530a, 530b may include respective complementary attachment members (not shown) that are configured to enable attachment (e.g., releasable attachment) of the first and second treatment coils 510a, 510b to the first ferromagnetic component 530a, and attachment (e.g., releasable attachment) of the third and fourth treatment coils 510c, 510d to the second ferromagnetic component 530b.

The first and second ferromagnetic components 530a, 530b may be supported relative to each other. For example, a bridge member (not shown) may be used to support the first and second ferromagnetic components 530a, 530b relative to each other. Such a bridge member may, for example, have a first end that is attached (e.g., releasably) to the first ferromagnetic component 530a and an opposed second end that is attached (e.g., releasably) to the second ferromagnetic component 530b. The bridge member may be configured to enable adjustment of the TMS device 500, for example to adjust positioning of the first, second, third, and fourth treatment coils 510a, 510b, 510c, 510d relative to the subject's head 52. The first end of the bridge member may be fixedly or movably (e.g., rotatably) attached to the first ferromagnetic component 530a. The second end of the bridge member may be fixedly or movably (e.g., rotatably) attached to the second ferromagnetic component 530b.

The bridge member may be adjustable between the first and second ends. For example, the bridge member may include a first portion that is attached to the first ferromagnetic component 530a and a second portion that is attached to the second ferromagnetic component 530b. The first and second portions of the bridge member may be configured to slide past each other, such that the TMS device 500 may be adjusted (e.g., relative to subject anatomy) by sliding the first and second portions of the bridge member relative to each other. The bridge member may include first and second portions that are angularly movable relative to each other (e.g., about a pivot or joint), such that the TMS device 500 may be adjusted (e.g., relative to subject anatomy).

It should be appreciated that the TMS device 500 is not limited to the illustrated configuration of treatment coils and ferromagnetic components. For instance, the TMS device 500 may include more or fewer treatment coils and/or more or fewer ferromagnetic components. For example, the TMS device 500 may include a single ferromagnetic component that is associated with (e.g., attached to) each of the first, second, third, and fourth treatment coils 510a, 510b, 510c, 510d. In another example, the TMS device may include three, five, six, seven, or more treatment coils and one or more corresponding ferromagnetic components. The treatment coils of such examples of the TMS device 500 may be oriented in any suitable configuration.

The TMS device 500, for example as configured and oriented relative to a subject as depicted in FIG. 5A, may be operated to cause the generation of a magnetic field in the subject's brain that may exhibit greater intensity in one or more regions located between respective centers of adjacent ones of the first, second, third, and fourth treatment coils 510a, 510b, 510c, 510d, in an upper region of the subject's brain, than in other regions of the subject's brain. For example, a first region of greater magnetic field intensity may be exhibited between respective portions of the first and second treatment coils 510a, 510b that are closest to each other. A second region of greater magnetic field intensity may be exhibited between respective portions of the second and fourth treatment coils 510b, 510d that are closest to each other. A third region of greater magnetic field intensity may be exhibited between respective portions of the fourth and third treatment coils 510d, 510c that are closest to each other. A fourth region of greater magnetic field intensity may be exhibited between respective portions of the third and first treatment coils 510c, 510a that are closest to each other.

The first, second, third, and fourth treatment coils 510a, 510b, 510c, and 510d may induce an electric field that exhibits a strong gradient. This gradient may be strong in opposite directions on opposed treatment coils (e.g., the first and second treatment coils 510a, 510b, or the first and third treatment coils 510a, 510c). This characteristic of the induced electric field may result in a magnetic field that is better able to stimulate straight nerve cells (e.g., peripheral neurons) in the subject's brain that may be more sensitive to stimulation in a rapidly changing current density. When the TMS device 500 is oriented relative to the subject 50 as shown, the magnetic field may be distributed so as to be simultaneously resident in both the first and second hemispheres of the subject's brain.

The first and second ferromagnetic components 530a, 530b may improve the energy efficiency of the treatment coils 510a-510d of the TMS device 500 (e.g., in contrast to using the bare treatment coils 510a-510d to generate a magnetic field, without the first and second ferromagnetic components 530a, 530b).

It should be appreciated that the TMS device 500 is not limited to the illustrated orientation relative to a subject (e.g., to the head 52 of the subject 50), and that the TMS device 500 may be differently oriented relative to the subject, such that the portions of the magnetic field that exhibit greater intensity are localized in different locations of the subject's anatomy (e.g., different locations in the subject's brain).

One or more characteristics of the magnetic field generated by the TMS device 500 may be altered by adjusting sizes of one or more of the first, second, third, or fourth treatment coils 510a, 510b, 510c, 510d. For example, by altering the respective size (e.g., diameter, coil density, etc.) of one or more of the treatment coils 510a-510d, the magnetic field generated by the TMS device 500 may be changed to target specific portions (e.g., zones) of the subject's brain. Adjusting the respective size of one or more of the treatment coils 510a-510d may cause the TMS device 500 to create a magnetic field that exhibits different intensities in different respective locations in the subject's brain. This may be useful, for example, for the treatment of peripheral nerves that may be straight (e.g., not curved).

Figure 6A:
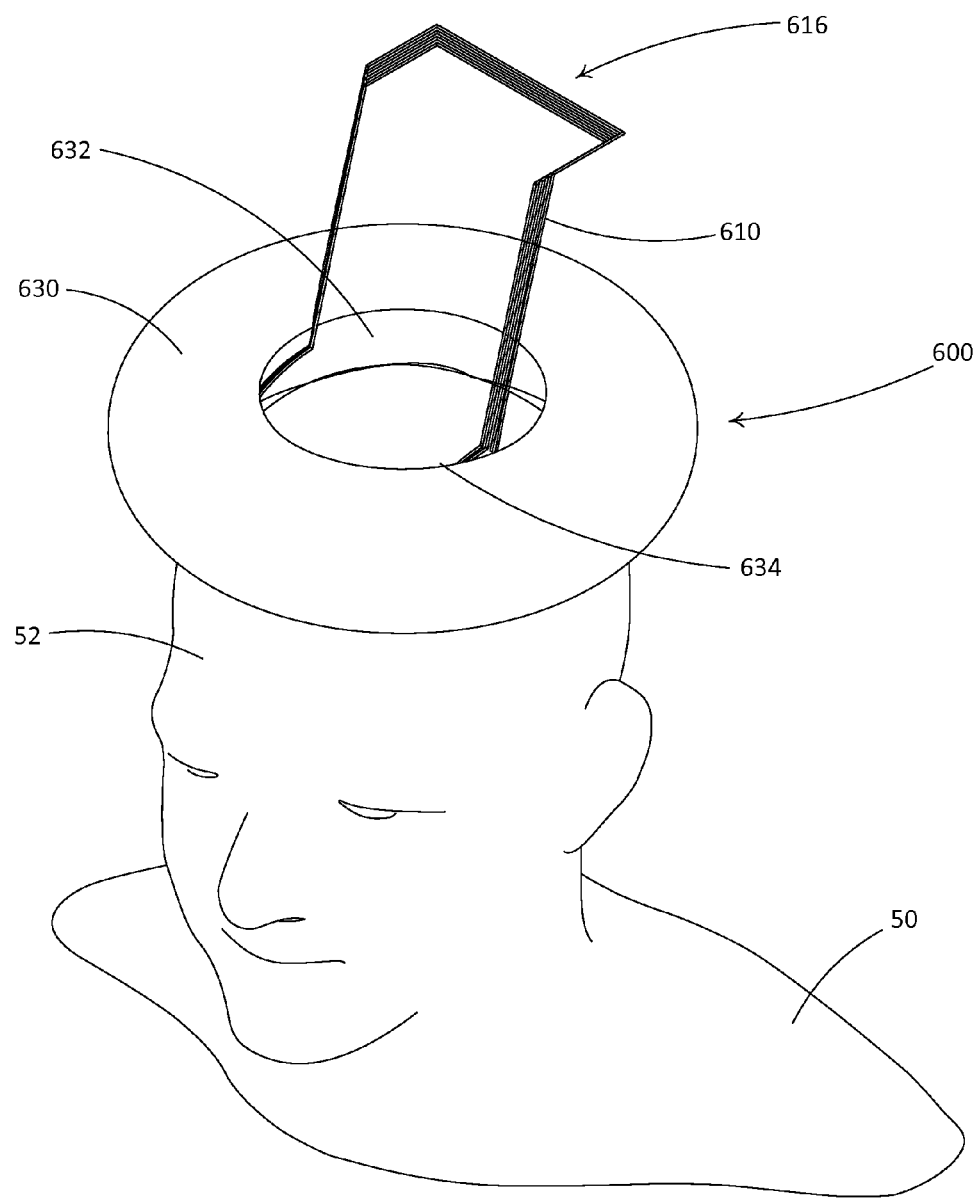
FIG. 6A depicts another example TMS device.
Figure 6B:
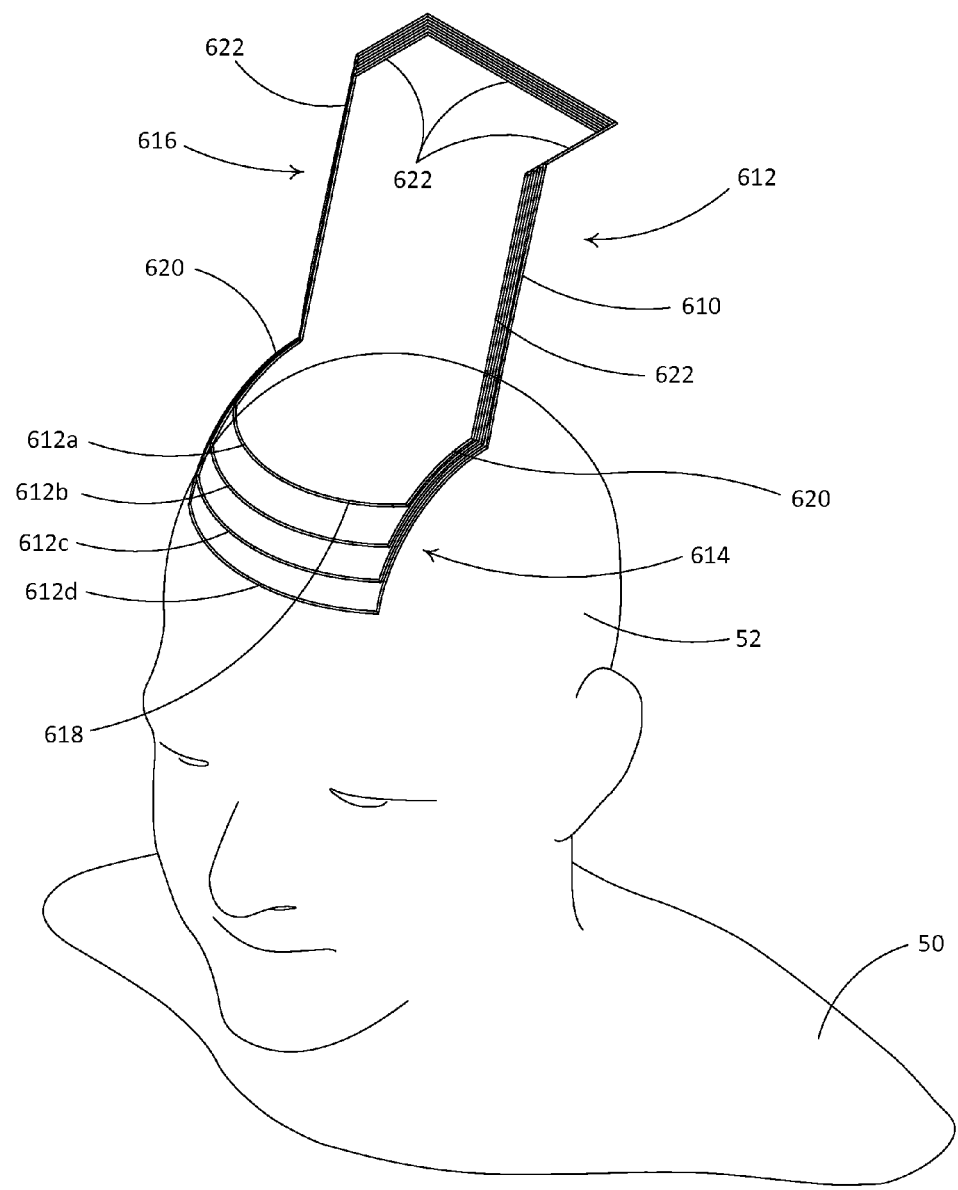
FIG. 6B depicts components of the TMS device of FIG. 6A.

FIGS. 6A and 6B depict a human subject 50 and an example TMS device that is 600 that is configured to generate a changing magnetic field in a target anatomy of the subject 50. The subject 50 may be, for example, a TMS patient. The target anatomy of the subject 50 may be, for example, brain tissue of the subject 50.

As shown, the TMS device 600 includes a treatment coil 610 and a ferromagnetic component 630. The TMS device 600 may be disposed proximate to the head 52 of the subject 50 in preparation for or during TMS treatment, for example as shown in FIG. 6A.

The treatment coil 610 may include one or more windings 612, such as a plurality of windings 612. As shown, the treatment coil 610 has a plurality of windings 612 that includes four windings 612a-612d. It should be appreciated that the treatment coil 610 may include more or fewer windings 612.

The treatment coil 610 may be fabricated from a monolithic piece of material. For example, a length of material (e.g., wire) may be continuously wound so as to define the plurality of windings 612. The windings 612, for example one or more of the windings 612a-612d, may be separately fabricated and supported relative to each other, for example attached to each other using one or more attachment members (not shown). A plurality of windings 612 that are separately fabricated may be placed in electrical communication with one another, for example using one or more electrically conductive attachment members that interconnect respective ones of the windings 612.

The windings 612 may be configured so as to define respective portions of the treatment coil 610. For example, the windings 612a-612d of the illustrated treatment coil 610 are configured to define a base portion 614 of the treatment coil 610 and a protruding portion 616 of the treatment coil 610. The base portion 614 may be configured to substantially conform to an anatomy of the subject's head 52. As shown, the base portion 614 defines a concave shape that is configured to substantially conform to a frontal region of the subject's head 52. The base portion 614 may be configured to make contact with the subject's head 52 during treatment, or to be spaced (e.g., a slight distance) from the subject's head 52 during treatment. The protruding portion 616 may be configured as a return portion of the treatment coil 610. As shown, the protruding portion 616 of the treatment coil 610 is angularly offset relative to the base portion 614, and extends outwardly from the base portion 614, in a direction away from the base portion 614 and away from the subject's head 52. It should be appreciated that the treatment coil 610 is not limited to the illustrated configuration of the base portion and/or protruding portions 614, 616. For example, the protruding portion 616 may be curved (e.g., to at least partially conform to the back of the subject's head 52). Such a configuration of the treatment coil 610 may reduce efficiency of the TMS device 600.

As shown, each winding 612 defines an arc-shaped front segment 618 that may be disposed proximate the front of the subject's head 52, opposed arc-shaped side segments 620 that may be disposed along corresponding sides of the subject's head 52, and a plurality of straight rear segments 622 that are connected to one another and that interconnect the side segments 620. The front and/or side segments 618, 620 may be configured to conform to corresponding portions of the subject's head 52. The base portion 614 of the illustrated treatment coil 610 is defined by the respective front and side segments 618, 620 of the windings 612, and the protruding portion 616 of the treatment coil 610 is defined by the plurality of rear segments 622.

Each winding 612 may define a respective length, for example as defined by a perimeter of the winding 612 and measured along a central axis through the winding 612. Respective ones of the plurality of windings 612 may have the same or different lengths. Each winding 612 may define any suitable cross-section along its length (e.g., perpendicular to its central axis), such as circular. The treatment coil 610, including one or more of the windings 612a-612d, may be made of any material that exhibits suitable electrical conductivity, such as copper.

Respective ones of the windings 612 may have the same or different shapes. The illustrated windings 612a-612d have similar shapes relative to one another, and may be at least partially nested relative to each other. The winding 612a may be referred to as an innermost winding of the plurality of windings 612, and the winding 612d may be referred to as an outermost winding of the plurality of windings 612.

The windings 612a-612d may be configured such that a spacing from winding to winding (e.g., between adjacent windings 612) remains uniform or varies. For example, the spacing between the windings 612a-612d may be defined by the respective lengths, shapes, positioning, etc., of the windings 612a-612d. As shown, the spacing of the windings 612 from each other varies by segment, such that the front segments 618 are spaced further apart from each other than the side segments 620 and rear segments 622 are spaced apart from each other.

The treatment coil 610 may be configured to define a coil geometry that conforms to a region of the subject's head 52. For example, two or more of the windings 612a-612d may be spaced from each other vertically such that the coil geometry of the treatment coil 610 may be concave with respect to the subject's head 52. As shown, the base portion 614 of the treatment coil 610 defines a concave, band-shaped coil geometry that encloses a portion of the subject's head 52.

The TMS device 600 may include a ferromagnetic component 630. The ferromagnetic component 630 may be configured to change one or more characteristics of a magnetic field that is generated by the treatment coil 610. As shown, the ferromagnetic component 630 may be disposed proximate to (e.g., located near) the treatment coil 610. The ferromagnetic component 630 may be made of any material that exhibits suitable ferromagnetic properties, such as powdered ferromagnetic iron particles.

The ferromagnetic component 630 may define any suitable shape, for example the illustrated annular, semi-toroidal shape. The ferromagnetic component 630 may define an inner surface 632 that faces the subject's head 52 and that is configured to at least partially conform to corresponding portions of the treatment coil 610 and/or to corresponding portions of the subject's head 52. The inner surface 632 may define a shape with proportions that are substantially similar to (e.g., slightly larger than) those of a corresponding portion of the subject's head 52.

The ferromagnetic component 630 may be configured to at least partially receive the treatment coil 610, such that the ferromagnetic component 630 is positioned proximate to a portion of the treatment coil 610. The ferromagnetic component may partially enclose a portion of the treatment coil 610, such as the base portion 614. The ferromagnetic component 630 may define a recess (not shown) that extends into the inner surface 632 of the ferromagnetic component 630 and that is configured to receive at least a portion of the treatment coil 610. The recess may be configured to receive one or more of the plurality of windings 612. When the treatment coil 610 is disposed in the recess, the ferromagnetic component 630 may at least partially surround respective portions of the plurality of windings 612. Portions of the ferromagnetic component 630 that define the recess may have a shape that is similar to (e.g., effectively the same as) one or more corresponding windings 612.

The ferromagnetic component 630 may define one or more openings that may expose corresponding portions of the subject's head 52, for example to promote cooling during TMS treatment. As shown, the ferromagnetic component 630 defines an opening 634 that extends therethrough. The illustrated opening 634 is located at an upper end of the ferromagnetic component 630. As shown, the opening 634 is configured such that the protruding portion 616 of the treatment coil 610 may be disposed in the opening 634. It should be appreciated that the ferromagnetic component 630 may be configured to define more or fewer openings. For example, the ferromagnetic component 630 may be configured to define a plurality of openings therethrough, or may be configured with no opening therethrough (e.g., configured with a dome-like shape).

The TMS device 600 may be configured such that the treatment coil 610 and the ferromagnetic component 630 are supported relative to each other. For example, the TMS device 600 may be configured such that the ferromagnetic component 630 supports the treatment coil 610 (e.g., in the recess). One or both of the treatment coil 610 and the ferromagnetic component 630 may include complementary attachment members (not shown) that are configured to enable attachment (e.g., releasable attachment) of the treatment coil 610 to the ferromagnetic component 630.

When the treatment coil 610 is supported by (e.g., attached to) the ferromagnetic component 630, the treatment coil 610 may be electrically isolated from the ferromagnetic component 630, for example using a dielectric. As shown, the dielectric may be air, and the plurality of windings 612 may be spaced from the inner surface 632 of the ferromagnetic component 630 when the treatment coil 610 is attached to the ferromagnetic component 630 (e.g., disposed in the recess). The treatment coil 610 may be attached to the ferromagnetic component 630 using one or more attachment members that are made of any suitable electrically isolating (e.g., dielectric) material.

When the treatment coil 610 and the ferromagnetic component 630 are supported relative to each other in an assembled configuration, for example as depicted in FIG. 6A, the protruding portion 616 of the treatment coil 610 may protrude through the opening 634 in the ferromagnetic component 630, and extend away from the subject's head 52 and from the ferromagnetic component 630. When the treatment coil 610 and the ferromagnetic component 630 are supported relative to each other in the assembled configuration, the treatment coil 610, for example the base portion 614 and at least a portion of the protruding portion 616, may be at least partially enclosed by the ferromagnetic component 630.

When the TMS device 600 is oriented relative to the subject 50, for example as depicted in FIG. 6A, the ferromagnetic component 630 (e.g., the inner surface 632) may be positioned near an outer surface of the subject's head 52. For example, the ferromagnetic component 630 may encircle a portion of the subject's head 52, such that the ferromagnetic component 630 encloses at least a portion of the treatment coil 610 (e.g., the base portion 614). The ferromagnetic component 630 may be configured such that the inner surface 632 substantially conforms to a corresponding portion of the subject's head 52. A portion of the ferromagnetic component 630 may extend beyond one or more portions of the treatment coil 610. For example, the ferromagnetic component 630 may define a radius (e.g., in a plane transverse to the subject 50), such that the ferromagnetic component extends beyond one or both of the base portion 614 and the protruding portion 616 of the treatment coil 610.

The TMS device 600, for example as configured and oriented relative to a subject as depicted in FIG. 6A, may be operated to cause the generation of a magnetic field in the subject's brain that may exhibit greater intensity in the frontal region in opposed sides of the subject's brain, than in other regions of the subject's brain. When the TMS device 600 is oriented relative to the subject 50 as shown, the magnetic field may be distributed so as to be simultaneously resident in both the first and second hemispheres of the subject's brain. The illustrated configuration of the ferromagnetic component 630 may exhibit a slower reduction of electric field stimulation as a function of distance normal to the surface of a subject's head.

When the TMS device 600 is oriented as depicted in FIG. 6A, the ferromagnetic component 630 may contribute to the spread of induced return currents generated by the TMS device 600, for example by spreading the return currents in the subject's head 52. Spreading the induced return currents may reduce side effects of TMS treatment, such as the stimulation of untargeted regions of the subject's brain. This may improve the efficiency of the treatment coil 610 and/or the TMS device 600.

Figure 6C:
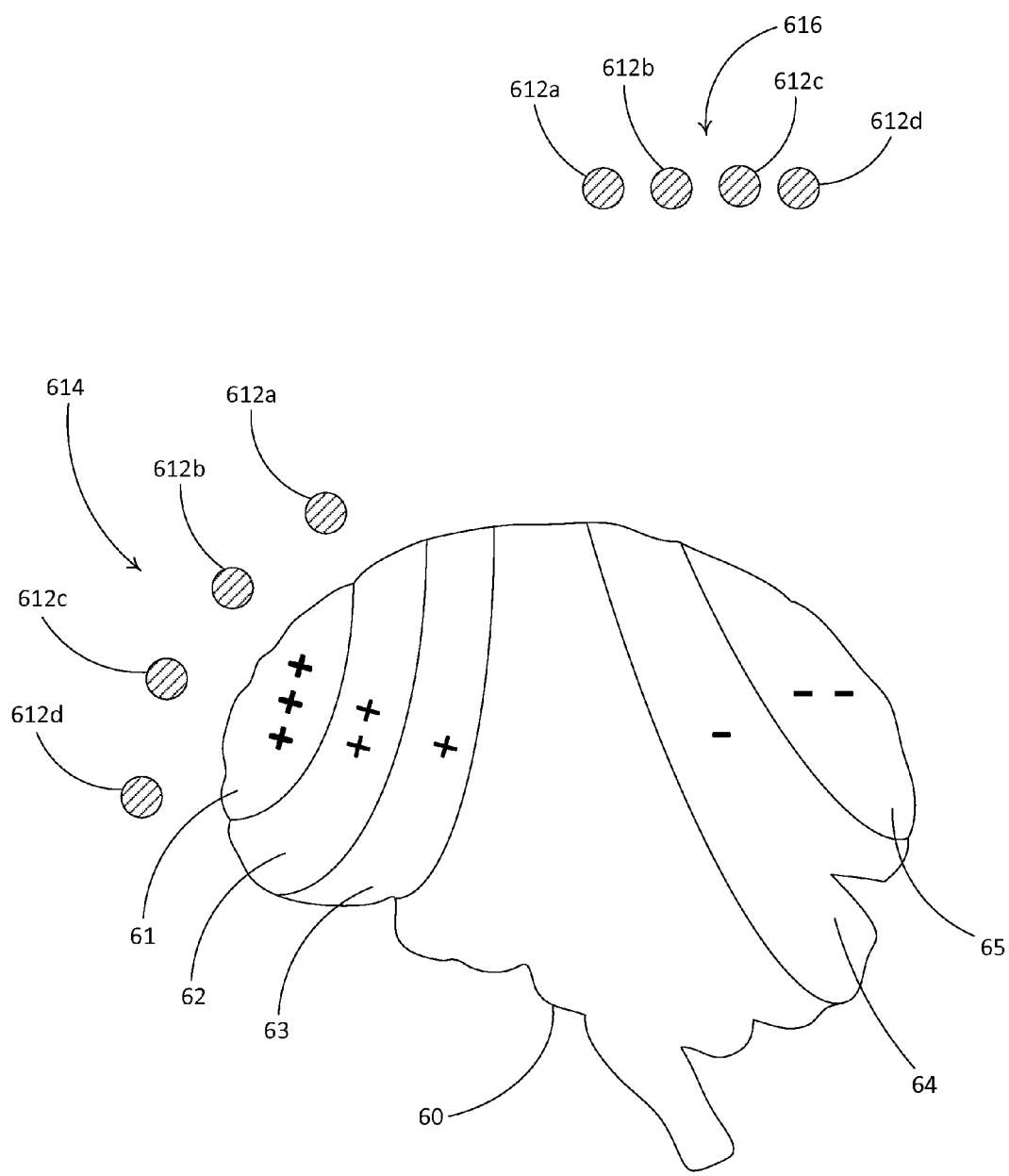
FIG. 6C depicts an example distribution of electrical field currents that may be induced by the example TMS device depicted in FIGS. 6A and 6B.

FIG. 6C depicts an example current distribution in the tissues of the brain 60 of a subject (e.g., the subject 50) when the TMS device 600 is operated without the ferromagnetic component 630. For example, with the ferromagnetic component 630 removed, the TMS device 600 may be operated such that the treatment coil 610 generates a magnetic field in the subject's brain 60. The magnetic field may induce currents in a targeted volume of tissues of the subject's brain 60. This targeted volume of stimulated brain tissue may be referred to as a stimulation volume. When the TMS device 600 is operated, for example during TMS treatment, the stimulation volume may include one or more regions that exhibit different levels of induced current (e.g., including regions 61, 62, and 63). The induced current in region 61 may be greater than the induced current in regions 62 and 63. The induced current in region 62 may be greater than the induced current in region 63. The magnetic field may induce return current in one or more regions of the subject's brain 60 (e.g., including regions 64 and 65). The induced return current in region 65 may be greater than the induced return current in region 64.

Figure 6D:
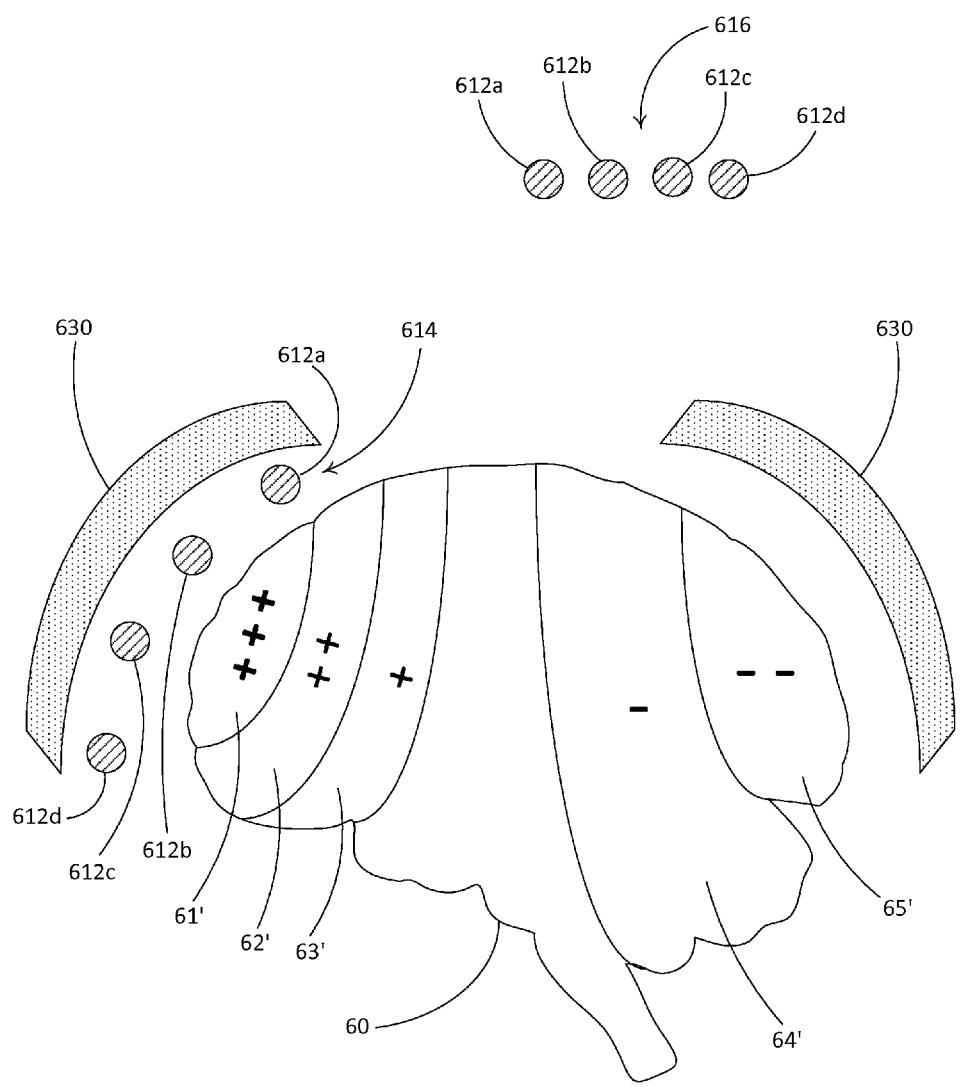
FIG. 6D depicts another example distribution of electrical field currents that may be induced by the example TMS device depicted in FIGS. 6A and 6B.

FIG. 6D depicts an example current distribution in the tissues of the brain 60 of a subject (e.g., the subject 50) when the TMS device 600 is operated with the ferromagnetic component 630. For example, the TMS device 600 may be operated such that the treatment coil 610 and the ferromagnetic component 630 cooperatively generate a magnetic field in the subject's brain 60. The magnetic field may induce currents in a targeted stimulation volume of the subject's brain 60. When the TMS device 600 is operated, for example during TMS treatment, the stimulation volume may include one or more regions that exhibit different levels of induced current (e.g., including regions 61', 62', and 63'). The induced current in region 61' may be greater than the induced current in regions 62' and 63'. The induced current in region 62' may be greater than the induced current in region 63'. The magnetic field may induce return current in one or more regions of the subject's brain 60 (e.g., including regions 64' and 65'). The induced return current in region 65' may be greater than the induced return current in region 64'.

The TMS device 600, when operated with the ferromagnetic component 630, may spread the induced return currents. For example, as shown, the regions 64' and 65' may be larger than the corresponding regions 64 and 65 induced when the TMS device 600 is operated without the ferromagnetic component 630. Spreading the induced return currents may reduce a current density in one or more regions of the brain 60 outside of the targeted stimulation volume, which may reduce TMS treatment dosage outside of the targeted stimulation volume. The ferromagnetic component 630 may improve the efficiency of the TMS device 600, for example without reducing the penetration depth of the magnetic field in the targeted stimulation volume.

It should be appreciated that the TMS device 600 is not limited to the illustrated orientation relative to a subject (e.g., to the head 52 of the subject 50), and that the TMS device 600 may be differently oriented relative to the subject, such that the portion of the magnetic field that exhibits greater intensity is localized in a different location of the subject's anatomy (e.g., a different location in the subject's brain).

Figure 7A:
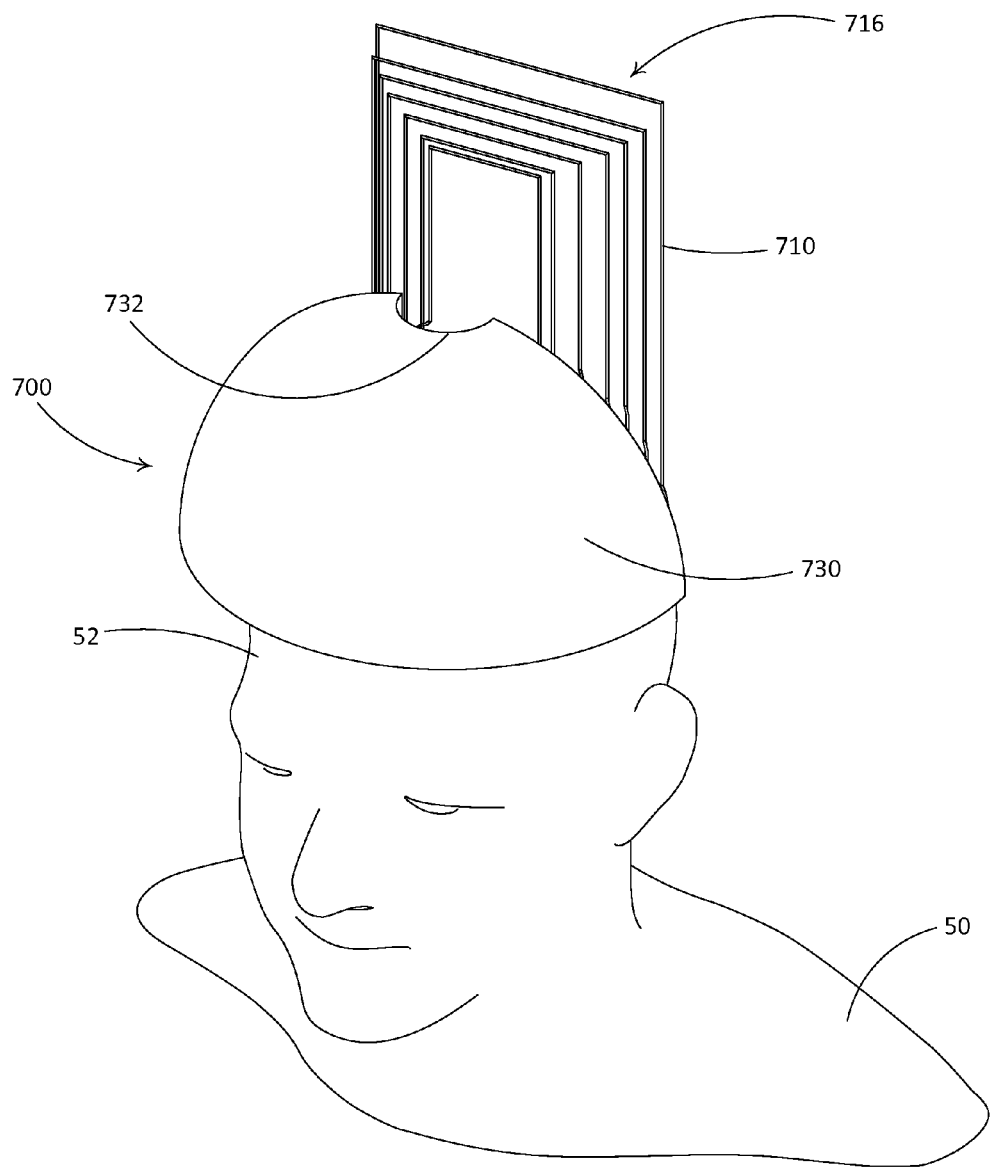
FIG. 7A depicts another example TMS device.
Figure 7B:
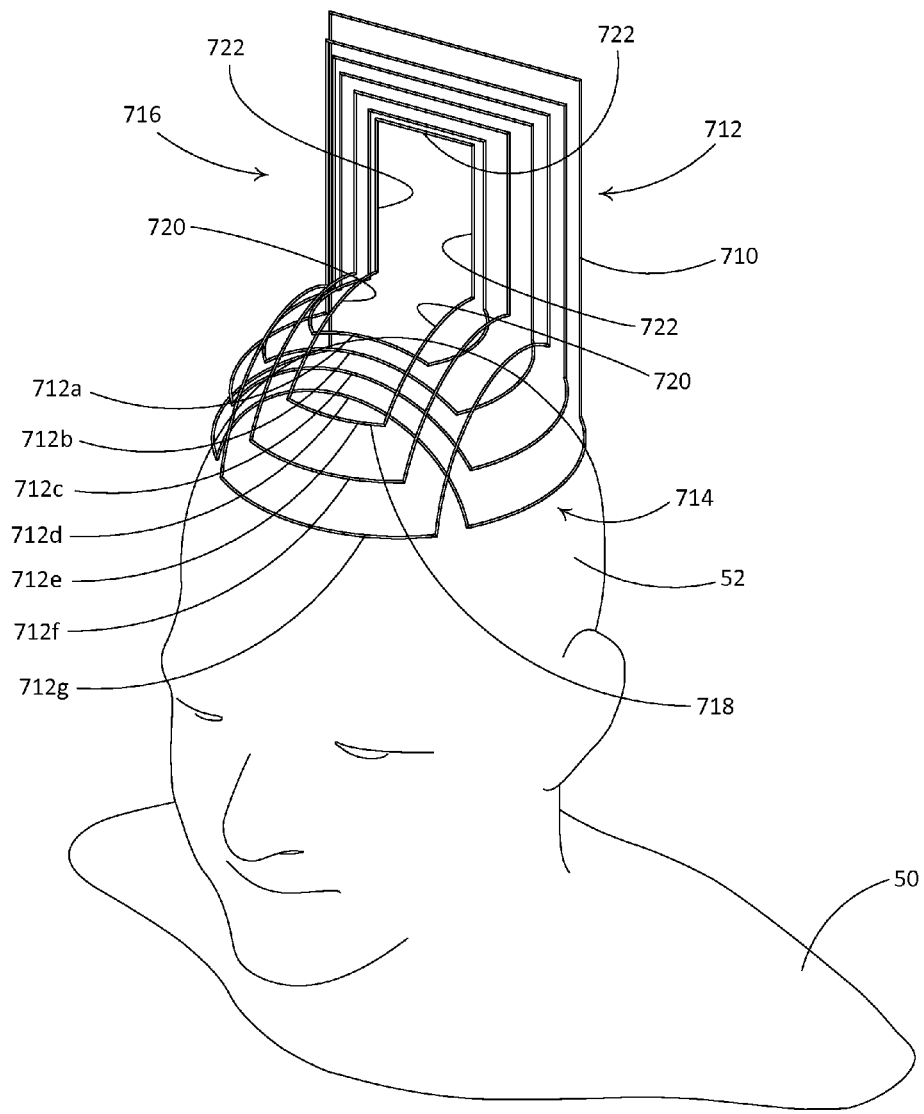
FIG. 7B depicts components of the TMS device of FIG. 7A.

FIGS. 7A and 7B depict a human subject 50 and an example TMS device 700 that is configured to generate a changing magnetic field in a target anatomy of the subject 50. The subject 50 may be, for example, a TMS patient. The target anatomy of the subject 50 may be, for example, brain tissue of the subject 50.

As shown, the TMS device 700 includes a treatment coil 710 and a ferromagnetic component 730. The TMS device 700 may be disposed proximate to the head 52 of the subject 50 in preparation for or during TMS treatment, for example as shown in FIG. 7A.

The treatment coil 710 may include one or more windings 712, such as a plurality of windings 712. As shown, the treatment coil 710 has a plurality of windings 712 that includes seven windings 712a-712g. It should be appreciated that the treatment coil 710 may include more or fewer windings 712.

The treatment coil 710 may be fabricated from a monolithic piece of material. For example, a length of material (e.g., wire) may be continuously wound so as to define the plurality of windings 712. The windings 712, for example one or more of the windings 712a-712g, may be separately fabricated and supported relative to each other, for example attached to each other using one or more attachment members (not shown). A plurality of windings 712 that are separately fabricated may be placed in electrical communication with one another, for example using one or more electrically conductive attachment members that interconnect respective ones of the windings 712.

The windings 712 may be configured so as to define respective portions of the treatment coil 710. For example, the windings 712a-712g of the illustrated treatment coil 710 are configured to define a base portion 714 of the treatment coil 710 and a protruding portion 716 of the treatment coil 710. The base portion 714 may be configured to substantially conform to an anatomy of the subject's head 52. As shown, the base portion 714 defines a concave shape that is configured to substantially conform to the subject's head 52. The base portion 714 may be configured to make contact with the subject's head 52 during treatment, or to be spaced (e.g., a slight distance) from the subject's head 52 during treatment. The protruding portion 716 may be configured as a return portion of the treatment coil 710. As shown, the protruding portion 716 of the treatment coil 710 is angularly offset relative to the base portion 714, and extends outwardly from the base portion 714, in a direction away from the base portion 714 and away from the subject's head 52. It should be appreciated that the treatment coil 710 is not limited to the illustrated configuration of the base portion and/or protruding portions 714, 716. For example, the protruding portion 716 may be curved (e.g., to at least partially conform to the back of the subject's head 52). Such a configuration of the treatment coil 710 may reduce efficiency of the TMS device 700.

As shown, each winding 712 defines an arc-shaped front segment 718 that may be disposed proximate the front of the subject's head 52, opposed arc-shaped side segments 720 that may be disposed along corresponding sides of the subject's head 52, and a plurality of straight rear segments 722 that are connected to one another and that interconnect the side segments 720. The front and/or side segments 718, 720 may be configured to conform to corresponding portions of the subject's head 52. The base portion 714 of the illustrated treatment coil 710 is defined by the respective front and side segments 718, 720 of the windings 712, and the protruding portion 716 of the treatment coil 710 is defined by the plurality of rear segments 722.

Each winding 712 may define a respective length, for example as defined by a perimeter of the winding 712 and measured along a central axis through the winding 712. Respective ones of the plurality of windings 712 may have the same or different lengths. Each winding 712 may define any suitable cross-section along its length (e.g., perpendicular to its central axis), such as circular. The treatment coil 710, including one or more of the windings 712a-712g, may be made of any material that exhibits suitable electrical conductivity, such as copper.

Respective ones of the windings 712 may have the same or different shapes. The illustrated windings 712a-712d have similar shapes relative to one another, and may be at least partially nested relative to each other. The illustrated windings 712e-712g have similar shapes relative to one another, and may be at least partially nested relative to each other.

The windings 712a-712g may be configured such that a spacing from winding to winding (e.g., between adjacent windings 712) remains uniform or varies. For example, the spacing between the windings 712a-712g may be defined by the respective lengths, shapes, positioning, etc., of the windings 712a-712g. As shown, the spacing of the windings 712 from each other varies by segment. For windings 712a-712d, the front segments 718 are spaced closer to each other than the side segments 720 are spaced apart from each other. For windings 712e-712g, the front segments 718 are spaced farther apart from each other than the side segments 720 are spaced apart from each other. The spacing of the rear segments 722 may be different from winding to winding.

The treatment coil 710 may be configured to define a coil geometry that conforms to a region of the subject's head 52. For example, two or more of the windings 712a-712g may be spaced from each other vertically such that the coil geometry of the treatment coil 710 may be concave with respect to the subject's head 52. As shown, the base portion 714 of the treatment coil 710 defines a concave, half-dome-shaped coil geometry that encloses a portion of the subject's head 52.

The TMS device 700 may include a ferromagnetic component 730. The ferromagnetic component 730 may be configured to change one or more characteristics of a magnetic field that is generated by the treatment coil 710. As shown, the ferromagnetic component 730 may be located proximate to the treatment coil 710. The ferromagnetic component 730 may be made of any material that exhibits suitable ferromagnetic properties, such as powdered ferromagnetic iron particles.

The ferromagnetic component 730 may define any suitable shape, for example the illustrated annular, half-dome shape. The ferromagnetic component 730 may define an inner surface (not shown) that faces the subject's head 52 and that is configured to at least partially conform to corresponding portions of the treatment coil 710 and/or to corresponding portions of the subject's head 52. The inner surface may define a shape with proportions that are substantially similar to (e.g., slightly larger than) those of a corresponding portion of the subject's head 52.

The ferromagnetic component 730 may be configured to at least partially receive the treatment coil 710, such that the ferromagnetic component 730 is positioned proximate to a portion of the treatment coil 710. The ferromagnetic component may partially enclose a portion of the treatment coil 610, such as the base portion 614. The ferromagnetic component 730 may define a recess (not shown) that extends into the inner surface of the ferromagnetic component 730 and that is configured to receive at least a portion of the treatment coil 710. The recess may be configured to receive one or more of the plurality of windings 712. When the treatment coil 710 is disposed in the recess, the ferromagnetic component 730 may at least partially surround respective portions of the plurality of windings 712 (e.g., the base portion 714 of the treatment coil 710). Portions of the ferromagnetic component 730 that define the recess may have a shape that is similar to (e.g., effectively the same as) one or more corresponding windings 712.

The ferromagnetic component 730 may be configured to expose one or more portions of the subject's head 52, for example to promote cooling during TMS treatment. As shown, the ferromagnetic component 730 defines a groove 732 that extends into an edge of the ferromagnetic component 730 near an upper end thereof. It should be appreciated that the groove 732 is no limited to the illustrated location. Furthermore, the ferromagnetic component 730 may be configured to define more or fewer grooves, such as a plurality of grooves (e.g., having the same or different sizes) or no groove at all. It should further be appreciated that the ferromagnetic component 730 may be configured to define one or more openings that extend therethrough (e.g., in addition to or in substitution for one or more grooves). For example, the ferromagnetic component 730 may be configured to define a plurality of openings that extend therethrough.

The TMS device 700 may be configured such that the treatment coil 710 and the ferromagnetic component 730 are supported relative to each other. For example, the TMS device 700 may be configured such that the ferromagnetic component 730 supports the treatment coil 710 (e.g., in the recess). One or both of the treatment coil 710 and the ferromagnetic component 730 may include complementary attachment members (not shown) that are configured to enable attachment (e.g., releasable attachment) of the treatment coil 710 to the ferromagnetic component 730.

When the treatment coil 710 is supported by (e.g., attached to) the ferromagnetic component 730, the treatment coil 710 may be electrically isolated from the ferromagnetic component 730, for example using a dielectric. As shown, the dielectric may be air, and the plurality of windings 712 may be spaced from the inner surface of the ferromagnetic component 730 when the treatment coil 710 is attached to the ferromagnetic component 730 (e.g., disposed in the recess). The treatment coil 710 may be attached to the ferromagnetic component 730 using one or more attachment members that are made of any suitable electrically isolating (e.g., dielectric) material.

When the treatment coil 710 and the ferromagnetic component 730 are supported relative to each other in an assembled configuration, for example as depicted in FIG. 7A, the protruding portion 716 of the treatment coil 710 may protrude beyond the ferromagnetic component 730, and extend away from the subject's head 52 and from the ferromagnetic component 730. When the treatment coil 710 and the ferromagnetic component 730 are supported relative to each other in the assembled configuration, the treatment coil 710, for example the base portion 714 and at least a portion of the protruding portion 716, may be at least partially enclosed by the ferromagnetic component 730.

When the TMS device 700 is oriented relative to the subject 50, for example as depicted in FIG. 7A, the ferromagnetic component 730 may be positioned near an outer surface of the subject's head 52. The ferromagnetic component may be disposed above one or more portions of the treatment coil 710 that are disposed near the subject's head 52 (e.g., above the base portion 714). The ferromagnetic component 730 may extend away from the base portion 714 of the treatment coil 710, for example towards the protruding portion 716. It should be appreciated that the ferromagnetic component 730 may be configured such that at least a portion of the ferromagnetic component 730 extends beyond one or more portions of the treatment coil 710. For example, the ferromagnetic component 730 may be configured such that a portion of the ferromagnetic component 730 extends upward beyond the protruding portion 716 of the treatment coil 710.

The TMS device 700, for example as configured and oriented relative to a subject as depicted in FIG. 7A, may be operated to cause the generation of a magnetic field in the subject's brain that may exhibit greater intensity in a frontal region of the subject's brain than in a dorsal region of the subject's brain. When the TMS device 700 is oriented relative to the subject 50 as shown, the magnetic field may be distributed so as to be simultaneously resident in both the first and second hemispheres of the subject's brain. The illustrated configuration of the ferromagnetic component 730 may enable the TMS device 700 to exhibit an increased energy efficiency, while maintaining or improving penetration depth (e.g., in comparison to characteristics exhibited by the TMS device 600, using the ferromagnetic component 630).

When the TMS device 700 is oriented as depicted in FIG. 7A, the ferromagnetic component 730 may contribute to the redistribution of a current concentration of reverse induced current, for example redistributing induced currents in the subject's head 52. The illustrated configuration of the ferromagnetic component 730 may exhibit a slower reduction of electric field stimulation as a function of distance normal to the surface of a subject's head. The TMS device 700 may better maintain electric field stimulation as a function of distance normal to the surface of a subject's head.

Figure 7C:
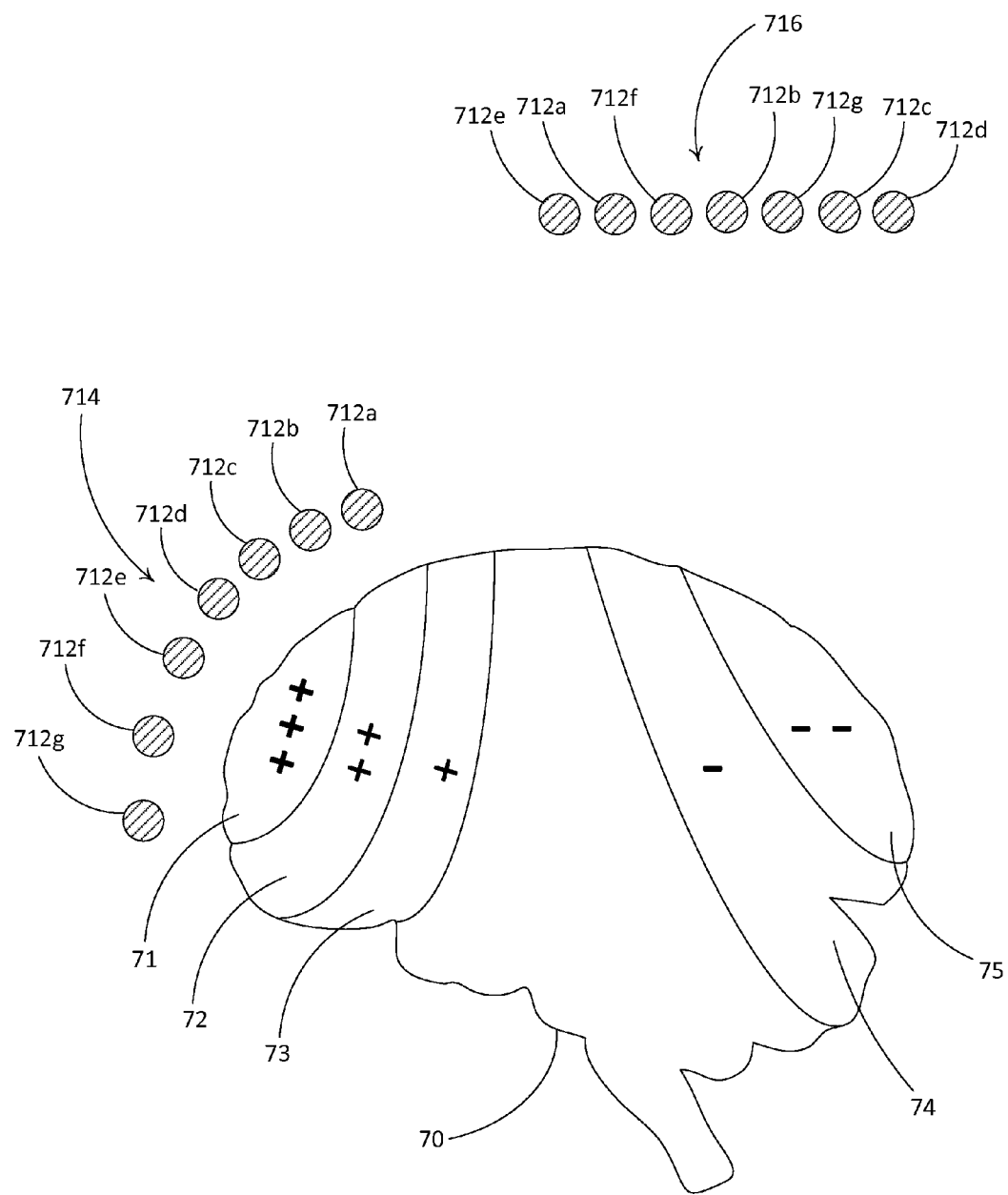
FIG. 7C depicts an example distribution of electrical field currents that may be induced by the example TMS device depicted in FIGS. 7A and 7B.

FIG. 7C depicts an example current distribution in the tissues of the brain 70 of a subject (e.g., the subject 50) when the TMS device 700 is operated without the ferromagnetic component 730. For example, with the ferromagnetic component 730 removed, the TMS device 700 may be operated such that the treatment coil 710 generates a magnetic field in the subject's brain 70. The magnetic field may induce currents in a targeted volume of tissues of the subject's brain 70. This targeted volume of stimulated brain tissue may be referred to as a stimulation volume. When the TMS device 700 is operated, for example during TMS treatment, the stimulation volume may include one or more regions that exhibit different levels of induced current (e.g., including regions 71, 72, and 73). The induced current in region 71 may be greater than the induced current in regions 72 and 73. The induced current in region 72 may be greater than the induced current in region 73. The magnetic field may induce return current in one or more regions of the subject's brain 70 (e.g., including regions 74 and 75). The induced return current in region 75 may be greater than the induced return current in region 74.

Figure 7D:
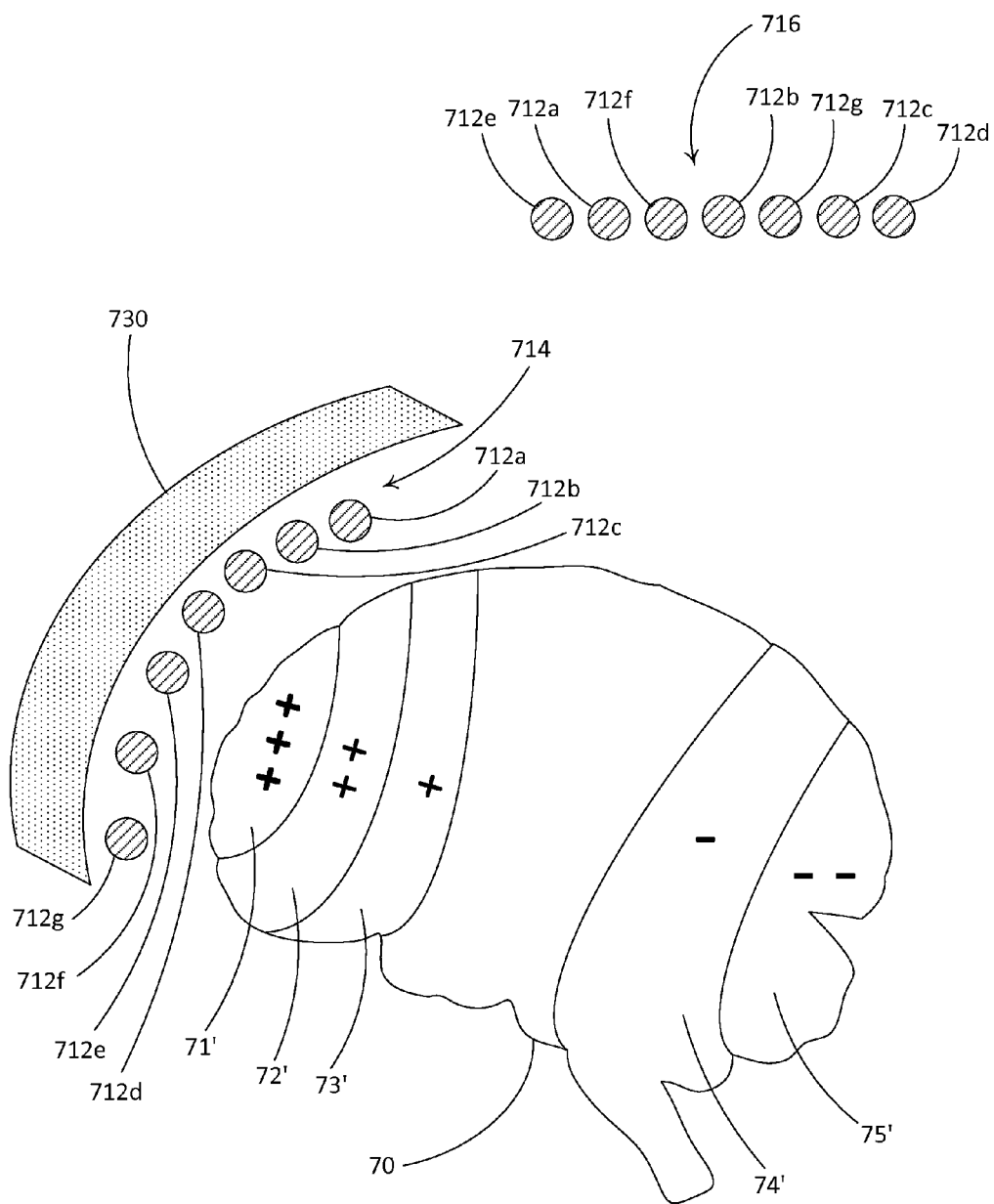
FIG. 7D depicts another example distribution of electrical field currents that may be induced by the example TMS device depicted in FIGS. 7A and 7B.

FIG. 7D depicts an example current distribution in the tissues of the brain 70 of a subject (e.g., the subject 50) when the TMS device 700 is operated with the ferromagnetic component 730. For example, the TMS device 700 may be operated such that the treatment coil 710 and the ferromagnetic component 730 cooperatively generate a magnetic field in the subject's brain 70. The magnetic field may induce currents in a targeted stimulation volume of the subject's brain 70. When the TMS device 700 is operated, for example during TMS treatment, the stimulation volume may include one or more regions that exhibit different levels of induced current (e.g., including regions 71', 72', and 73'). The induced current in region 71' may be greater than the induced current in regions 72' and 73'. The induced current in region 72' may be greater than the induced current in region 73'. The magnetic field may induce return current in one or more regions of the subject's brain 70 (e.g., including regions 74' and 75'). The induced return current in region 75' may be greater than the induced return current in region 74'.

The TMS device 700, when operated with the ferromagnetic component 730, may redistribute (e.g., displace, reorient, change the volume of, etc.) the induced return currents. For example, as shown, the regions 74' and 75' may be displaced further from the targeted stimulation volume, for example relative to the protruding portion 716 of the treatment coil 710 induced when the TMS device 700 is operated without the ferromagnetic component 730. Redistributing the induced return currents may reduce a current density in one or more regions of the brain 70 outside of the targeted stimulation volume, which may reduce TMS treatment dosage outside of the targeted stimulation volume.

When the TMS device 700 is oriented as depicted in FIG. 7A, the ferromagnetic component 730 may improve the efficiency of the treatment coil 710 and/or the TMS device 700, for example without reducing the penetration depth of the magnetic field in the targeted stimulation volume. As shown, the ferromagnetic component 730 may extend beyond the base portion 714 of the treatment coil 710. This configuration may move the return induced currents in the subject's head 52. Moving the induced return currents may reduce side effects of TMS treatment, such as the stimulation of untargeted regions of the subject's brain.

It should be appreciated that the TMS device 700 is not limited to the illustrated orientation relative to a subject (e.g., to the head 52 of the subject 50), and that the TMS device 700 may be differently oriented relative to the subject, such that the portion of the magnetic field that exhibits greater intensity is localized in a different location of the subject's anatomy (e.g., a different location in the subject's brain).

Figure 8A:
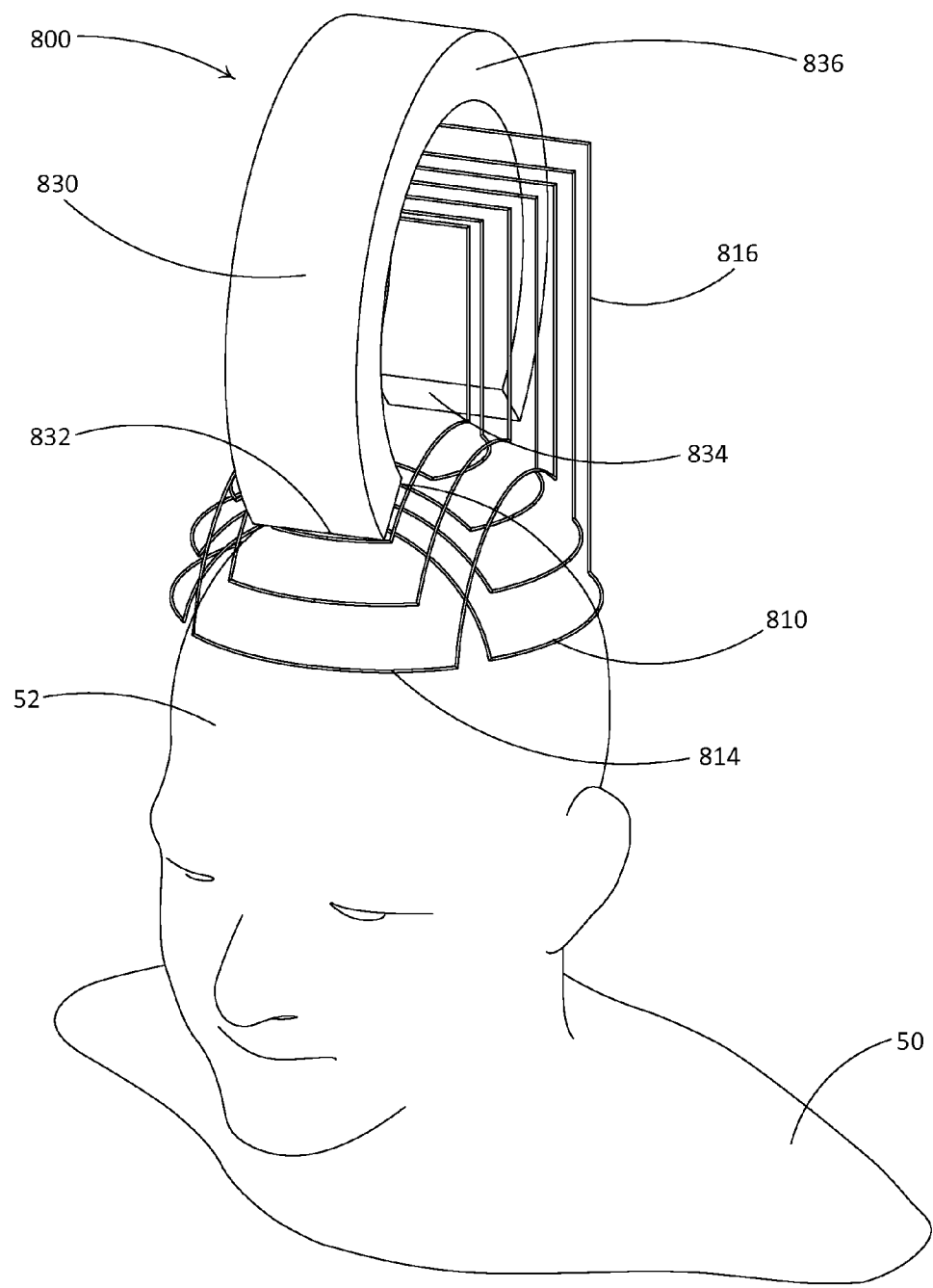
FIG. 8A depicts another example TMS device.
Figure 8B:
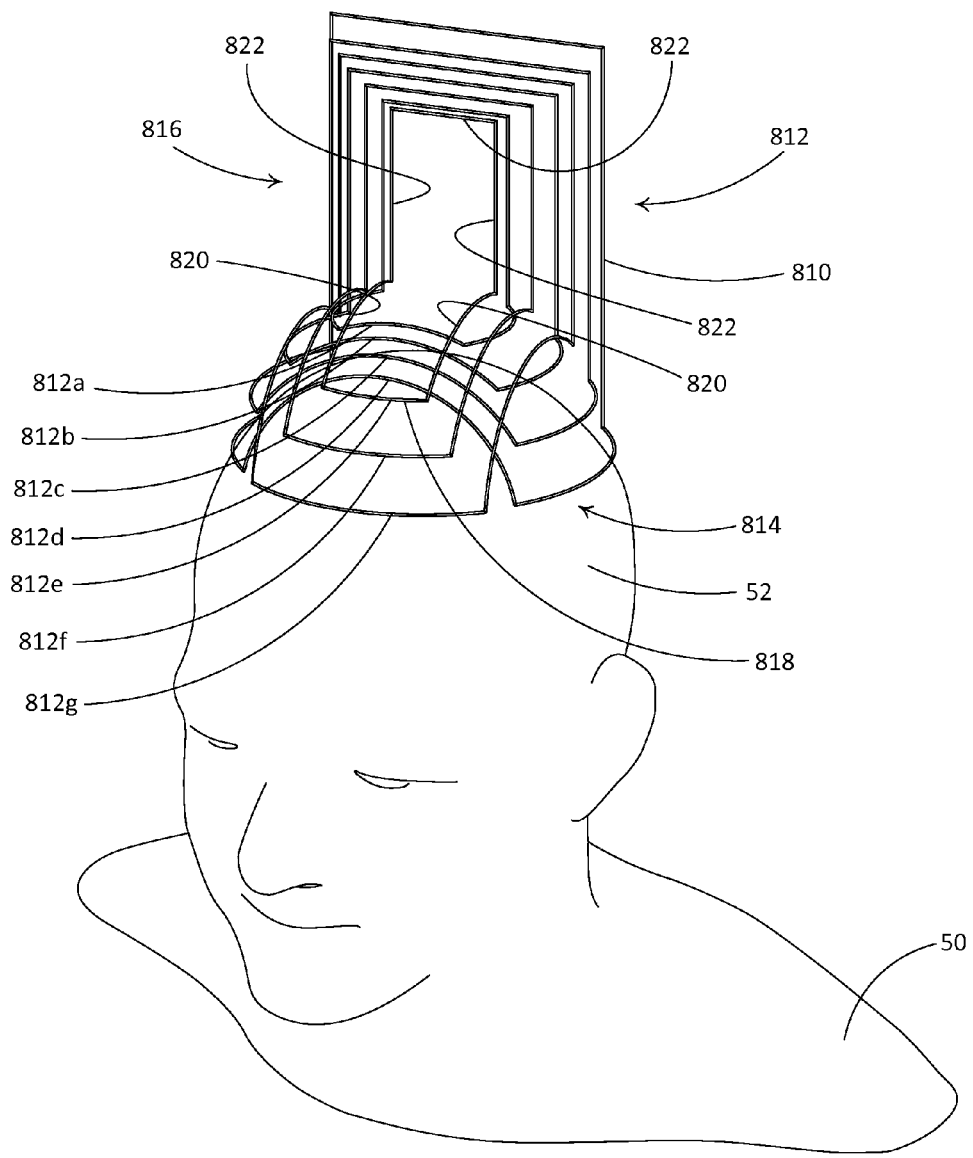
FIG. 8B depicts components of the TMS device of FIG. 8A.

FIGS. 8A and 8B depict a human subject 50 and an example TMS device 800 that is configured to generate a changing magnetic field in a target anatomy of the subject 50. The subject 50 may be, for example, a TMS patient. The target anatomy of the subject 50 may be, for example, brain tissue of the subject 50.

As shown, the TMS device 800 includes a treatment coil 810 and a ferromagnetic component 830. The TMS device 800 may be disposed proximate to the head 52 of the subject 50 in preparation for or during TMS treatment, for example as shown in FIG. 8A.

The treatment coil 810 may include one or more windings 812, such as a plurality of windings 812. As shown, the treatment coil 810 has a plurality of windings 812 that includes seven windings 812a-812g. It should be appreciated that the treatment coil 810 may include more or fewer windings 812.

The treatment coil 810 may be fabricated from a monolithic piece of material. For example, a length of material (e.g., wire) may be continuously wound so as to define the plurality of windings 812. The windings 812, for example one or more of the windings 812a-812g, may be separately fabricated and supported relative to each other, for example attached to each other using one or more attachment members (not shown). A plurality of windings 812 that are separately fabricated may be placed in electrical communication with one another, for example using one or more electrically conductive attachment members that interconnect respective ones of the windings 812.

The windings 812 may be configured so as to define respective portions of the treatment coil 810. For example, the windings 812a-812g of the illustrated treatment coil 810 are configured to define a base portion 814 of the treatment coil 810 and a protruding portion 816 of the treatment coil 810. The base portion 814 may be configured to substantially conform to an anatomy of the subject's head 52. As shown, the base portion 814 defines a concave shape that is configured to substantially conform to the subject's head 52. The base portion 814 may be configured to make contact with the subject's head 52 during treatment, or to be spaced (e.g., a slight distance) from the subject's head 52 during treatment. The protruding portion 816 may be configured as a return portion of the treatment coil 810. As shown, the protruding portion 816 of the illustrated treatment coil 810 is angularly offset relative to the base portion 814, and extends outwardly from the base portion 814, in a direction away from the base portion 814 and away from the subject's head 52. It should be appreciated that the treatment coil 810 is not limited to the illustrated configuration of the base portion and/or protruding portions 814, 816. For example, the protruding portion 816 may be curved (e.g., to at least partially conform to the back of the subject's head 52). Such a configuration of the treatment coil 810 may reduce efficiency of the TMS device 800.

As shown, each winding 812 defines an arc-shaped front segment 818 that may be disposed proximate the front of the subject's head 52, opposed arc-shaped side segments 820 that may be disposed along corresponding sides of the subject's head 52, and a plurality of straight rear segments 822 that are connected to one another and that interconnect the side segments 820. The front and/or side segments 818, 820 may be configured to conform to corresponding portions of the subject's head 52. The base portion 814 of the illustrated treatment coil 810 is defined by the respective front and side segments 818, 820 of the windings 812, and the protruding portion 816 of the treatment coil 810 is defined by the plurality of rear segments 822.

Each winding 812 may define a respective length, for example as defined by a perimeter of the winding 812 and measured along a central axis through the winding 812. Respective ones of the plurality of windings 812 may have the same or different lengths. Each winding 812 may define any suitable cross-section along its length (e.g., perpendicular to its central axis), such as circular. The treatment coil 810, including one or more of the windings 812a-812g, may be made of any material that exhibits suitable electrical conductivity, such as copper.

Respective ones of the windings 812 may have the same or different shapes. The illustrated windings 812a-812d have similar shapes relative to one another, and may be at least partially nested relative to each other. The illustrated windings 812e-812g have similar shapes relative to one another, and may be at least partially nested relative to each other.

The windings 812a-812g may be configured such that a spacing from winding to winding (e.g., between adjacent windings 812) remains uniform or varies. For example, the spacing between the windings 812a-812g may be defined by the respective lengths, shapes, positioning, etc., of the windings 812a-812g. As shown, the spacing of the windings 812 from each other varies by segment. For windings 812a-812d, the front segments 818 are spaced closer to each other than the side segments 820 are spaced apart from each other. For windings 812e-812g, the front segments 818 are spaced farther apart from each other than the side segments 820 are spaced apart from each other. The spacing between the rear segments 822 may be different from one winding to winding.

The treatment coil 810 may be configured to define a coil geometry that conforms to a region of the subject's head 52. For example, two or more of the windings 812a-812g may be spaced from each other vertically such that the coil geometry of the treatment coil 810 may be concave with respect to the subject's head 52. As shown, the base portion 814 of the treatment coil 810 defines a concave, half-dome-shaped coil geometry that encloses a portion of the subject's head 52.

The TMS device 800 may include a ferromagnetic component 830. The ferromagnetic component 830 may be configured to change one or more characteristics of a magnetic field that is generated by the treatment coil 810. The ferromagnetic component 830 may be disposed proximate to (e.g., located near) at least a portion of the treatment coil 810. As shown, the ferromagnetic component 830 may be disposed proximate to the base portion 814 of the treatment coil 810, so as to partially enclose a part of the base portion 814 (e.g., an area of the base portion 814). The ferromagnetic component 830 may be made of any material that exhibits suitable ferromagnetic properties, such as powdered ferromagnetic iron particles.

The ferromagnetic component 830 may be configured to at least partially enclose a portion of the treatment coil 810. As shown, the ferromagnetic component 830 is configured to at least partially enclose the protruding portion 816 of the treatment coil 810. The ferromagnetic component may define any suitable shape, for example the illustrated arc shape. As shown, the ferromagnetic component 830 defines a first end 832, an opposed second end 834 that is spaced from the first end 832, and an arc-shaped intermediate section 836 that extends from the first end 832 to the second end 834.

The ferromagnetic component 830 may be configured such that the first and second ends 832, 834, are disposed on opposed sides of the protruding portion 816 of the treatment coil 810. For example, the first end 832 of the ferromagnetic component 830 may be configured to be disposed at a location on a first, forward-facing side of the protruding portion 816 of the treatment coil 810, the second end 834 of the ferromagnetic component 830 may be configured to be disposed at a location on a second, rearward-facing side of the protruding portion 816 of the treatment coil 810.

The ferromagnetic component 830 may be configured to at least partially enclose the protruding portion 816 of the treatment coil 810. For example, the intermediate section 836 of the ferromagnetic component 830 may define an arc that at least partially encloses the protruding portion 816. As shown, the arc defined by the intermediate portion 836 defines a loop that at least partially encloses the protruding portion 816 of the treatment coil 810.

It should be appreciated that the ferromagnetic component 830 is not limited to the illustrated configuration, for example the illustrated intermediate section 836 that extends up and over an upper end of the protruding portion, and that the geometry of the ferromagnetic component 830 may be differently configured relative to the treatment coil 810. For example, the ferromagnetic component 830 may be configured such that the second end 834 of may be located near the back of the subject's head during treatment, and the intermediate section 836 may be configured to at least partially conform to the geometry of the subject's head. In such a configuration, the intermediate section 836 may extend over the base portion 814 of the treatment coil 810 and through an opening defined by the protruding portion 816. Such a configuration of the ferromagnetic component 830 may enable the TMS device 800 to exhibit increases in corresponding electric fields induced by one or more current levels delivered to the treatment coil 810 (e.g., in comparison to the illustrated configuration of the treatment coil 830). In another example, the ferromagnetic component may be configured to extend from one side of the protruding portion 816 to the other, for example by extending around the upper end of the protruding portion 816, around either opposed side of the protruding portion 816, or any combination thereof.

It should further be appreciated that the ferromagnetic component 830 may be configured to differently enclose at least a portion of the treatment coil 810 (e.g., the protruding portion 816 of the treatment coil 810). For example, the ferromagnetic component may define a plurality of substantially straight (e.g., straight or slightly curved) intermediate sections between the first and second ends 832, 834 that extend from one side of the protruding portion 816 to the other.

As shown, the first end 832 of the ferromagnetic component 830 is disposed near, so as to partially enclose, a portion of the base portion 814 of the treatment coil 810. The first end 832 may define a substantially flat surface (as shown), or may be configured to conform to the corresponding portion of the base portion 814 of the treatment coil 810. The second end 834 of the ferromagnetic component 830 is disposed near, so as to partially enclose, a portion of the protruding portion 816 of the treatment coil 810. The second end 834 may define a substantially flat surface (as shown), or may be configured to conform to the corresponding portion of the protruding portion 816 of the treatment coil 810. It should be appreciated that the ferromagnetic component 830 is not limited to the illustrated configurations of the first and second ends 832, 834, and that the ferromagnetic component 830 may be configured with one or both of the first and second ends 832, 834 in any other suitable location relative to the treatment coil 810.

The TMS device 800 may be configured such that the treatment coil 810 and the ferromagnetic component 830 are supported relative to each other. For example, the TMS device 800 may be configured such that the ferromagnetic component 830 supports the treatment coil 810. One or both of the treatment coil 810 and the ferromagnetic component 830 may include complementary attachment members (not shown) that are configured to enable attachment (e.g., releasable attachment) of the treatment coil 810 to the ferromagnetic component 830. For example, the first and second ends 832, 834 of the ferromagnetic component 830 may include attachment members that are configured to be secured to complementary attachment members supported by the base and protruding portions 814, 816, respectively, of the treatment coil 810.

When the treatment coil 810 is supported by (e.g., attached to) the ferromagnetic component 830, the treatment coil 810 may be electrically isolated from the ferromagnetic component 830, for example using a dielectric. As shown, the dielectric may be air, and the plurality of windings 812 may be spaced from the ferromagnetic component 730 when the treatment coil 810 is attached to the ferromagnetic component 830. The treatment coil 810 may be attached to the ferromagnetic component 830 using one or more attachment members that are made of any suitable electrically isolating (e.g., dielectric) material.

When the treatment coil 810 and the ferromagnetic component 830 are supported relative to each other in an assembled configuration, for example as depicted in FIG. 8A, the protruding portion 816 of the treatment coil 810 may be disposed in the loop defined by the ferromagnetic component 830. When the treatment coil 810 and the ferromagnetic component 830 are supported relative to each other in the assembled configuration, the treatment coil 810, for example respective portion of the base and protruding portions 814, 816, may be at least partially enclosed by the ferromagnetic component 830.

The TMS device 800, for example as configured and oriented relative to a subject as depicted in FIG. 8A, may be operated to cause the generation of a magnetic field in the subject's brain that may exhibit more intensity in a frontal region of the subject's brain than in a dorsal region of the subject's brain. When the TMS device 800 is oriented relative to the subject 50 as shown, the magnetic field may be distributed so as to be simultaneously resident in both the first and second hemispheres of the subject's brain.

It should be appreciated that the TMS device 800 is not limited to the illustrated orientation relative to a subject (e.g., to the head 52 of the subject 50), and that the TMS device 800 may be differently oriented relative to the subject, such that the portion of the magnetic field that exhibits greater intensity is localized in a different location of the subject's anatomy (e.g., a different location in the subject's brain).

A transcranial magnetic stimulation (TMS) device may be configured to be adjustable and/or reconfigurable, for instance with respect to the anatomy of a subject. For example, a TMS device may be configured to be adjusted and/or reconfigured to conform to a location (e.g., on, in, or near the subject) where TMS treatment will be applied. Adjusting and/or reconfiguring a TMS device may alter one or more characteristics exhibited by a magnetic field generated by the TMS device during treatment (e.g., a stimulation volume of the magnetic field, a distribution of the magnetic field in the subject's anatomy, a penetration depth of the magnetic field, a focality of the magnetic field, a location of the magnetic field relative to the subject's anatomy, or the like). For example, adjusting and/or reconfiguring a TMS device may allow the magnetic field generated by the TMS device to be distributed and/or shaped (e.g., by volume) so as to target specific neuroanatomy in a subject's brain (e.g., one or more of the orbitofrontal cortex, the dorsolateral prefrontal cortex (DLPFC), the supplementary motor area (SMA), the auditory cortex, etc.).

Figure 9:
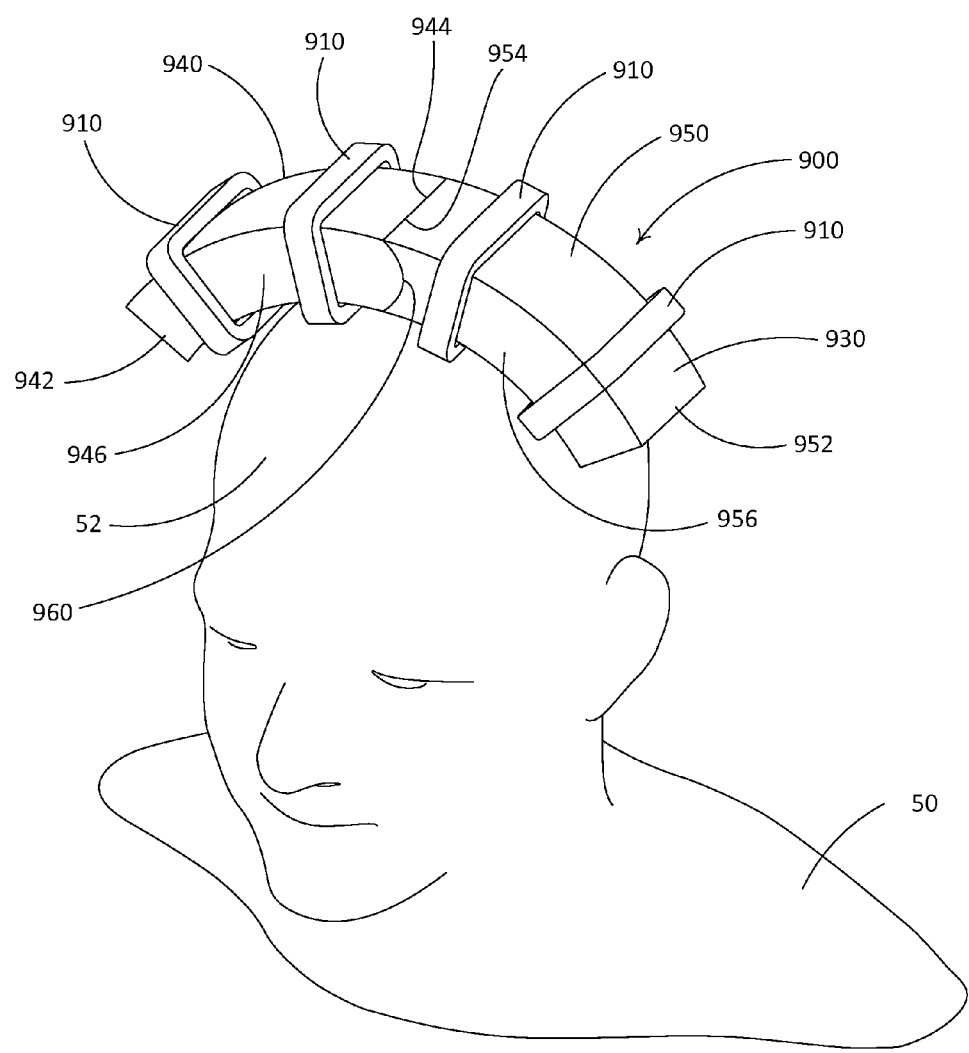
FIG. 9 depicts an example adjustable TMS device.

FIG. 9 depicts a human subject 50 and an example TMS device 900 that is configured to generate a changing magnetic field in a target anatomy of the subject 50. The subject 50 may be, for example, a TMS patient. The target anatomy of the subject 50 may be, for example, brain tissue of the subject 50. The TMS device 900 may be configured to be adjustable and/or reconfigurable relative to an anatomy of the subject 50. As shown, the TMS device 900 includes a plurality of treatment coils 910 and a ferromagnetic component 930. The TMS device 900 may be disposed proximate to the subject's head 52 in preparation for or during TMS treatment, for example as shown in FIG. 9.

The TMS device 900 may be configured to be adjustable, for example relative to the anatomy of the subject's head 52. For example, the ferromagnetic component 930 of the TMS device 900 may be configured to be adjustable. The ferromagnetic component 930 may include multiple pieces. One or more pieces of the ferromagnetic component 930 may be configured so as to be adjustable relative to one or more other pieces of the ferromagnetic component 930. For example, the illustrated ferromagnetic component 930 includes a first piece 940 and a second piece 950. The first and second pieces 940, 950 are configured to be adjustable (e.g., pivotally adjustable) relative to each other. The ferromagnetic component 930 (e.g., the first and second pieces 940, 950) may be made of any material that exhibits suitable ferromagnetic properties, such as powdered ferromagnetic iron particles.

The first piece 940 of the ferromagnetic component 930 defines a free end 942, a constrained end 944 that is spaced from the free end 942 and attached to the second piece 950, and an intermediate section 946 that extends from the free end 942 to the constrained end 944. The second piece 950 of the ferromagnetic component 930 defines a free end 952, a constrained end 954 that is spaced from the free end 952 and attached to the first piece 940, and an intermediate section 956 that extends from the free end 952 to the constrained end 954. As shown, the intermediate sections 946, 956 of the first and second pieces 940, 950 define respective arced shapes. The intermediate sections 946, 956 may define an arc shape of the ferromagnetic component 930.

The first and second pieces 940, 950 of the ferromagnetic component 930 may be configured to be adjustable relative to each other. As shown, the respective constrained ends 944, 954 of the first and second pieces 940, 950 are joined together at a joint 960. The joint 960 may be configured to enable one or more degrees of freedom in adjustment of the first and second pieces 940, 950 relative to each other. As shown, the joint 960 is configured to enable adjustment in one degree of freedom, such that the first and second pieces 940, 950 may be pivoted relative to each other about the joint 960. To illustrate, the first and second pieces 940, 950 may be pivoted about the joint 960 such that the respective free ends 942, 952 are brought closer together or are moved further apart from each other (e.g., in a coronal plane). It should be appreciated that the ferromagnetic component 930 is not limited to adjustment via the illustrated degree of freedom. For example, the ferromagnetic component 930 may be configured to be adjustable in a different single degree of freedom (e.g., in a transverse plane), or may be configured to be adjustable in multiple degrees of freedom (e.g., in both coronal and transverse planes).

As shown, the first and second pieces 940, 950 have approximately the same length (e.g., as defined by the free ends 942, 952 and the constrained ends 944, 954, respectively), such that the joint 960 is located substantially at a midpoint of the ferromagnetic component 930 (e.g., equidistant from the free end 942 of the first piece 940 and free end 952 of the second piece 950). It should be appreciated that the ferromagnetic component 930 is not limited to the illustrated location of the joint 960. For example, the joint 960 may be located along the ferromagnetic component 930 (e.g., such that the first and second pieces 940, 950 define different respective lengths).

The shape of the ferromagnetic component 930 may be changed by adjusting the first and second pieces 940, 950. This may allow the ferromagnetic component 930 to better conform to the anatomy of the subject's head 52 (e.g., to the shape of the subject's head 52). Adjusting the ferromagnetic component 930 to better fit subject anatomy may improve the efficiency of the TMS device 900. Adjusting the first and second pieces 940, 950 may change the orientation (e.g., the position and/or spacing) of respective ones of the treatment coils 910 relative to each other. Changing the shape (e.g., the arc shape) of the ferromagnetic component 930, and thereby the orientation of one or more of the treatment coils 910, may alter one or more characteristics of a magnetic field generated by the TMS device 900 (e.g., in the subject's head 52). For example, adjusting one or both of the first and second pieces 940, 950 of the ferromagnetic component 930 may enable the TMS device 900 to maintain efficiency across a variety of head types (e.g., head shapes, sizes, etc.). The TMS device 900 may be configured to be adjustable and/or reconfigurable in preparation for and/or during TMS treatment.

It should be appreciated that the adjustable and/or reconfigurable TMS device 900 is not limited to the illustrated configuration of the adjustable ferromagnetic component 930. The ferromagnetic component 930 may be configured so as to be differently adjustable. For example, the ferromagnetic component 930 may be configured to include more than two pieces that may be joined together at more than two adjustable joints, such that the ferromagnetic component 930 is adjustable at multiple locations. Each of the one or more adjustable joints may be configured to enable adjustment in one or more degrees of freedom. The ferromagnetic component 930 may be monolithic and adjustable. For example, the ferromagnetic component 930 may be configured (e.g., during fabrication) to define a flexible ferromagnetic component that enables adjustability (e.g., relative to the subject's head 52).

The illustrated adjustable TMS device 900 has a plurality of treatment coils 910 that includes four treatment coils 910. Each treatment coil 910 may be defined by one or more windings (e.g., a plurality of windings) that may be fabricated, for example, by wrapping an electrically conductive material (e.g., copper wire) one or more times around an outer surface of the ferromagnetic component 930 (e.g., directly onto the ferromagnetic component 930 or onto an intermediate medium secured to the ferromagnetic component 930) at a respective location. The treatment coils 910 may define respective winding densities that are the same or different relative to each other.

As shown, each of the first and second pieces 940, 950 supports two treatment coils 910. The treatment coils 910 may be spaced apart from each other (e.g., substantially equally spaced from each other) along a length of the ferromagnetic component 930 (e.g., as defined by the free end 942 of the first piece 940 and the free end 952 of the second piece 950). Additionally, the illustrated TMS device 900 is configured such that the respective attachment locations of the treatment coils 910 of the first piece 940 mirror the respective attachment locations of the treatment coils 910 of the second piece 950, about the midpoint of the ferromagnetic component 930. The illustrated treatment coils 910 are fixed in respective positions along the ferromagnetic component 930 and have the same winding densities. It should be appreciated that the adjustable TMS device 900 is not limited to the illustrated configuration of treatment coils 910. For example, the TMS device 900 may be configured with more or fewer treatment coils 910 in any suitable locations along the ferromagnetic component 930.

The adjustable TMS device 900 may be configured such that one or more treatment coils 910 are adjustable with respect to the ferromagnetic component 930. For example, the TMS device 900 may be configured such that one or more of the treatment coils 910 may be repositionable along the first and/or second pieces 940, 950 of the ferromagnetic component 930 (e.g., repositionable between the between the free ends 942, 952 of the first and second pieces 940, 950). An adjustable treatment coil 910 may be freely adjustable (e.g., between two opposed positions) or may be incrementally adjustable (e.g., between predefined positions that are spaced apart from each other).

The adjustable TMS device 900 may be configured with removable treatment coils 910. For example, the TMS device 900 may be configured such that one or more of the treatment coils 910 are removable from the ferromagnetic component 930. This configuration may enable the TMS device 900 to be reconfigured with respect to the treatment coils 910. For example, the configuration of the TMS device 900 may be changed by swapping out one or more treatment coils 910. To illustrate, a first treatment coil having a first winding density may be removed from the ferromagnetic component 930, and replaced with a second treatment coil 910 having a different (e.g., higher or lower) winding density. The ferromagnetic component 930 may include one or more markings, such as a plurality of markings, which may correspond to predetermined placement positions for one or more treatment coils 910.

The adjustable TMS device 900, for example as configured and oriented relative to a subject as depicted in FIG. 9, may be operated to cause the generation of a magnetic field in the subject's brain that may exhibit a greater intensity in an upper region of the subject's brain than in other regions of the subject's brain. The region of greater intensity may be located in the subject's brain, near a midpoint along the ferromagnetic component 930 (e.g., as defined by the free ends 942, 952), for example below the joint 960. When the TMS device 900 is oriented relative to the subject 50 as shown, the magnetic field may be distributed so as to be simultaneously resident in both the first and second hemispheres of the subject's brain.

It should be appreciated that the TMS device 900 is not limited to the illustrated orientation relative to a subject (e.g., to the head 52 of the subject 50), and that the TMS device 900 may be differently oriented relative to the subject, such that the portion of the magnetic field that exhibits greater intensity is localized in a different location of the subject's anatomy (e.g., a different location in the subject's brain).

One or more characteristics of the magnetic field generated by the TMS device 900 may be altered by adjusting the ferromagnetic component 930. Adjusting the ferromagnetic component 930 may broaden or narrow one or more gaps between respective ones of the treatment coils 910. For example, if the ferromagnetic component 930 is adjusted such that the free ends 942, 952 are moved toward each other, (e.g., closer to the subject's head, such that respective spaces between the subject's head and one or both of the first and second pieces 940, 950 are reduced), the resulting magnetic field generated by the TMS device 900 may exhibit more focality, and may exhibit decreased penetration depth. If the ferromagnetic component 930 is adjusted such that the free ends 942, 952 are moved away from each other, (e.g., further from the subject's head, such that respective spaces between the subject's head and one or both of the first and second pieces 940, 950 are increased), the resulting magnetic field generated by the TMS device 900 may exhibit less focality, and may exhibit increased penetration depth.

Adjusting the ferromagnetic component 930 may cause an electric field that is induced by the magnetic field (e.g., generated by the TMS device 900) to develop a saddle point. The saddle point may result from adjusting the ferromagnetic component 930 such that a gap between respective ones of the treatment coils 910 is broadened or narrowed. For example, such a gap may be defined between two treatment coils 910 nearest the joint 960, the treatment coils 910 supported by the first and second piece 940, 950, respectively. Such a saddle point may develop under the ferromagnetic component 930, in a location near the joint 960. The presence of a saddle point in an electric field induced by the TMS device 900 may enable orienting the TMS device 900 relative to subject anatomy (e.g., relative to a subject's head during TMS treatment) so as to avoid stimulating a surface location located over a location to be stimulated, and/or may enable the stimulation of tissue below a sensitive region of subject anatomy (e.g., a sensitive surface location on the subject). Peak induced electric fields may remain at the surface but not above (e.g., directly above) a location of interest. Neighboring tissues with similar conductivities may receive higher current density.

Adjusting the ferromagnetic component 930 may reduce an air gap between the TMS device 900 and the subject's head 52, which may increase (e.g., maximize) the efficiency of the TMS device 900. Adjusting the ferromagnetic component 930 may allow for the creation of a local zone of lower electric field on a portion of the subject's anatomy (e.g., the surface of the subject's head). This may allow for stimulation below a sensitive surface location of the subject. Peak induced electric fields may remain at the surface but not above (e.g., directly above) a location of interest. Neighboring tissues with similar conductivities may receive higher current density.

Figure 10:
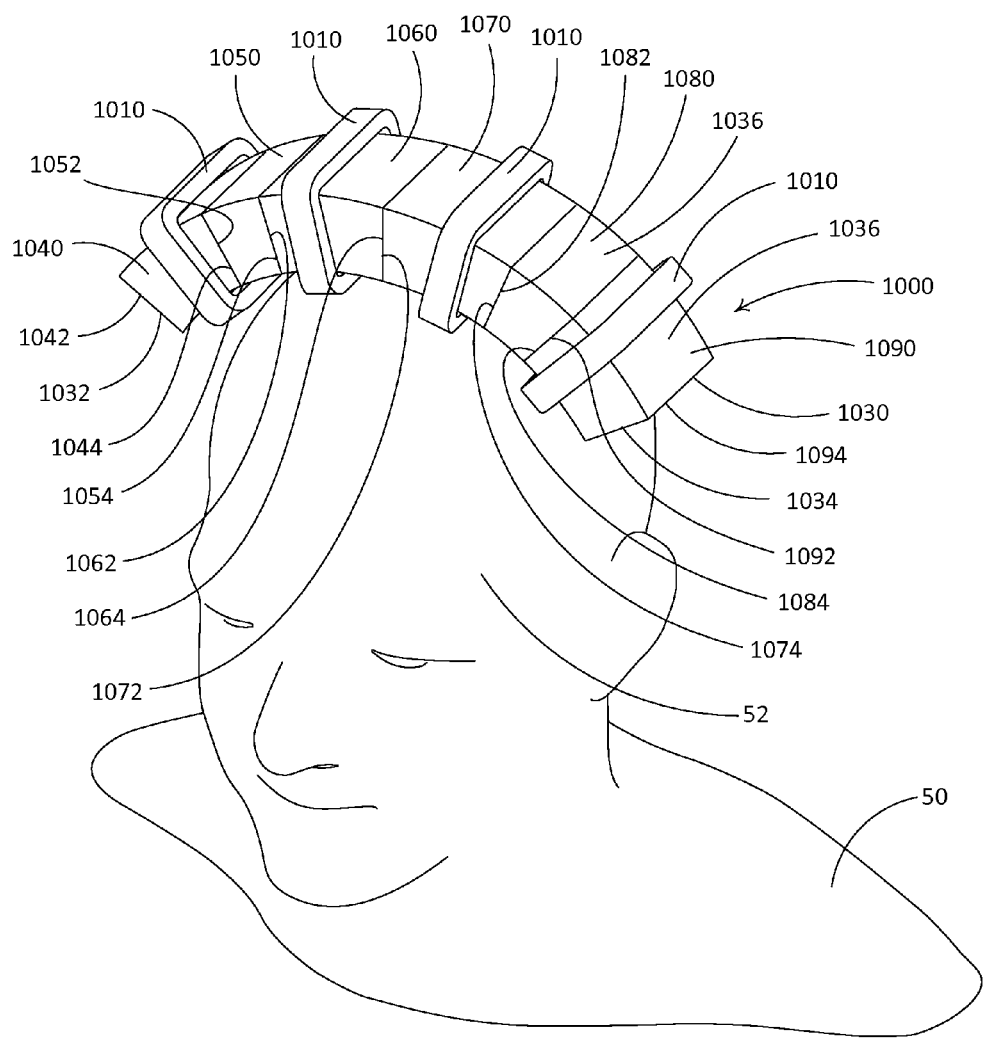
FIG. 10 depicts another example adjustable TMS device.

FIG. 10 depicts a human subject 50 and an example TMS device 1000 that is configured to generate a changing magnetic field in a target anatomy of the subject 50. The subject 50 may be, for example, a TMS patient. The target anatomy of the subject 50 may be, for example, brain tissue of the subject 50. The TMS device 1000 may be configured to be adjustable and/or reconfigurable relative to an anatomy of the subject 50. As shown, the TMS device 1000 includes a plurality of treatment coils 1010 and a ferromagnetic component 1030. The TMS device 1000 may be disposed proximate to the subject's head 52 in preparation for or during TMS treatment, for example as shown in FIG. 10.

The TMS device 1000 may be configured to be adjustable, for example relative to the anatomy of the subject's head 52. For example, the ferromagnetic component 1030 of the TMS device 1000 may be configured to be adjustable. As shown, the ferromagnetic component 1030 defines an arc shape that extends from a first end 1032 to an opposed second end 1034. The illustrated ferromagnetic component 1030 includes a plurality of pieces 1036 that are configured to be releasably attached to each other. The ferromagnetic component 1030 may be adjusted, for example, by adding or removing pieces 1036. As shown, the plurality of pieces 1036 define respective first through sixth segments 1040, 1050, 1060, 1070, 1080, and 1090 (i.e., 1040-1090) of the ferromagnetic component 1030. The pieces 1036 of the ferromagnetic component 1030 (e.g., the first through sixth segments 1040-1090) may be made of any material that exhibits suitable ferromagnetic properties, such as powdered ferromagnetic iron particles.

The first segment 1040 defines a first end 1042 that also defines the first end 1032 of the illustrated configuration of the ferromagnetic component 1030, and an opposed second end 1044. The second through fifth segments 1050-1080 define first and second ends 1052 and 1054, 1062 and 1064, 1072 and 1074, and 1082 and 1084, respectively. The sixth segment 1090 defines a first end 1092 and an opposed second end 1044 that also defines the second end 1034 of the illustrated configuration of the ferromagnetic component 1030. The first through sixth segments 1040-1090 may define respective lengths (e.g., as defined by the corresponding first and second ends) that are the same or different with respect to each other. As shown, the second and fifth segments 1050, 1080 have approximately the same length; the third and fourth segments 1060, 1070 have approximately the same length; and the first and sixth segments 1040, 1090 have approximately the same length. The second and fifth segments 1050, 1080 are shorter than the first and sixth segments 1040, 1090; the first and sixth segments 1040, 1090 are shorter than the third and fourth segments 1060, 1070.

The respective first and second ends of one or more of the first through sixth segments 1040-1090 (e.g., the respective first and second ends of each piece 1036) may define corresponding first and second end surfaces (not shown) that may be angularly offset relative to each other. For example, the first and second end surfaces of the illustrated segments are angularly offset such that each segment defines a tapered, truncated wedge shape that narrows with increasing proximity to the subject's head 52. One or more of the segments may define first and second end surfaces that are differently angled with respect to each other (e.g., parallel to each other).

The first through sixth segments 1040-1090 may be configured to be releasably attached to each other. For example, one or both of the first and second ends of each segment may define an attachment structure (not shown). The attachment structures of the segments may be configured to releasably engage with each other, for example to secure the ferromagnetic component 1030 in an assembled configuration. In the example assembled configuration of the ferromagnetic component 1030 depicted in FIG. 10, the second end 1044 of the first segment 1040 is releasably attached to the first end 1052 of the second segment 1050, the second end 1054 of the second segment 1050 is releasably attached to the first end 1062 of the third segment 1060, the second end 1064 of the third segment 1060 is releasably attached to the first end 1072 of the fourth segment 1070, the second end 1074 of the fourth segment 1070 is releasably attached to the first end 1082 of the fifth segment 1080, and the second end 1084 of the fifth segment 1080 is releasably attached to the first end 1092 of the sixth segment 1090. As shown, when the first through sixth segments 1040-1090 (i.e., the plurality of pieces 1036) are releasably attached to each other, the ferromagnetic component 1030 defines an arc shape.

The shape of the ferromagnetic component 1030 may be changed by adding or removing pieces 1036. This may allow the ferromagnetic component 1030 to better conform to the anatomy of the subject's head 52 (e.g., to the shape of the subject's head 52). Adjusting the ferromagnetic component 1030 to better fit subject anatomy may improve the efficiency of the TMS device 1000. For example, one or more segments may be removed and/or replaced to change the configuration of the ferromagnetic component 1030, that is, to reconfigure the ferromagnetic component 1030. In an example illustration, the second and fifth segments 1050, 1080 may be removed (e.g., detached) from the ferromagnetic component 1030. With the second and fifth segments 1050, 1080 removed, the second end 1044 of the first segment 1040 may be releasably attached to the first end 1062 of the third segment 1060, and the second end 1074 of the fourth segment 1070 may be releasably attached to the first end 1092 of the sixth segment 1090, such that the ferromagnetic component 1030 is assembled in a different configuration. In another example illustration of reconfiguring the ferromagnetic component 1030, one or more segments may be removed and replaced with respective segments having different characteristics than the one or more removed segments. Such differing characteristics may include, for example, one or more of the length of the segment, the angular offset of the first and second end surfaces, differences in a treatment coil 1010 attached to the segment, or the lack of a treatment coil 1010.

Removing, adding, and/or replacing one or more pieces 1036 (e.g., segments) of the ferromagnetic component 1030 may change the orientation (e.g., the position and/or spacing) of respective ones of the treatment coils 1010 relative to each other. Changing the shape (e.g., the arc shape) of the ferromagnetic component 1030, and thereby the orientation of one or more of the treatment coils 1010, may alter one or more characteristics of a magnetic field generated by the TMS device 1000 (e.g., in the subject's head 52). For example, removing, adding, and/or replacing one or more pieces 1036 of the ferromagnetic component 1030 may enable the TMS device 1000 to maintain efficiency across a variety of head types (e.g., head shapes, sizes, etc.). The TMS device 1000 may be configured to be adjustable and/or reconfigurable in preparation for and/or during TMS treatment.

The illustrated adjustable TMS device 1000 has a plurality of treatment coils 1010 that includes four treatment coils 1010. The treatment coils 1010 may be attached to respective pieces 1036 (e.g., segments) of the ferromagnetic component 1030. Each treatment coil 1010 may be defined by one or more windings (e.g., a plurality of windings) that may be fabricated, for example, by wrapping an electrically conductive material (e.g., copper wire) one or more times around an outer surface of a respective one of the segments of the ferromagnetic component 1030 (e.g., directly onto the segment or onto an intermediate medium secured to the segment). The treatment coils 1010 may define respective winding densities that are the same or different relative to each other.

The ferromagnetic component 1030 may be configured such that each piece 1036 (e.g., each segment) includes none, one, or more treatment coils 1010. As shown, each of the first, third, fourth, and sixth segments 1040, 1060, 1070, and 1090 support a respective one of the treatment coils 1010. The treatment coils 1010 may be attached to respective locations along the first, third, fourth, and sixth segments 1040, 1060, 1070, and 1090 such that the treatment coils 1010 are equally spaced from each other along the ferromagnetic component 1030. The illustrated treatment coils 1010 are fixed in respective positions along the first, third, fourth, and sixth segments 1040, 1060, 1070, and 1090 and have the same winding densities. It should be appreciated that the adjustable TMS device 1000 is not limited to the illustrated configuration of treatment coils 1010. For example, the TMS device 1000 may be configured with more or fewer treatment coils 1010 in any suitable locations along the ferromagnetic component 1030 (e.g., such that one or more segments include more than one treatment coil 1010).

The adjustable TMS device 1000 may be configured such that one or more treatment coils 1010 are adjustable with respect to the ferromagnetic component 1030. For example, the TMS device 1000 may be configured such that one or more of the treatment coils 1010 may be repositionable along corresponding segments of the ferromagnetic component 1030. An adjustable treatment coil 1010 may be freely adjustable (e.g., between two opposed positions along a segment) or may be incrementally adjustable (e.g., between predefined positions along a segment that are spaced apart from each other).

The adjustable TMS device 1000 may be reconfigured with respect to the treatment coils 1010. For example, the configuration of the TMS device 1000 may be changed by removing one or more segments that include treatment coils 1010 and replacing them with one or more segments having different treatment coils 1010. To illustrate, a segment having a first treatment coil with a first winding density may be removed from the ferromagnetic component 1030, and replaced with a segment having a treatment coil 1010 with a different (e.g., higher or lower) winding density. One or more segments of the ferromagnetic component 1030 may include one or more respective markings, such as a plurality of markings, which may correspond to predetermined placement positions for one or more treatment coils 1010.

The adjustable TMS device 1000, for example as configured and oriented relative to a subject as depicted in FIG. 10, may be operated to cause the generation of a magnetic field in the subject's brain that may exhibit a greater intensity in an upper region of the subject's brain than in other regions of the subject's brain. The region of greater intensity may be located in the subject's brain, near a midpoint along the ferromagnetic component 1030 (e.g., as defined by the first and second ends 1032, 1034). When the TMS device 1000 is oriented relative to the subject 50 as shown, the magnetic field may be distributed so as to be simultaneously resident in both the first and second hemispheres of the subject's brain.

It should be appreciated that the TMS device 1000 is not limited to the illustrated orientation relative to a subject (e.g., to the head 52 of the subject 50), and that the TMS device 1000 may be differently oriented relative to the subject, such that the portion of the magnetic field that exhibits greater intensity is localized in a different location of the subject's anatomy (e.g., a different location in the subject's brain).

One or more characteristics of the magnetic field generated by the TMS device 1000 may be altered by adjusting the ferromagnetic component 1030. For example, adding or removing one or more pieces 1036 of the ferromagnetic component 1030 may change respective spaces between one or more portions of the ferromagnetic component 1030 and a subject's head. In an example illustration, if one or more pieces 1036 are added to or removed from the ferromagnetic component 1030, such that the first and second ends 1032, 1034 are moved toward each other (e.g., closer to subject's head), the resulting magnetic field generated by the TMS device 1000 may exhibit more focality, and may exhibit decreased penetration depth. In another example illustration, if one or more pieces 1036 are added to or removed from the ferromagnetic component 1030, such that the first and second ends 1032, 1034 are moved away from each other (e.g., further from the subject's head), the resulting magnetic field generated by the TMS device 1000 may exhibit less focality, and may exhibit increased penetration depth.

Adding one or more pieces 1036 to, or removing one or more pieces 1036 from, the ferromagnetic component 1030 may cause the magnetic field generated by the TMS device 1000 to become more focal or more diffuse, such that a volume and/or area of stimulated tissue may be adjusted (e.g., to target one or more specific regions of the brain). Adjusting the ferromagnetic component 1030 (e.g., by adding or removing one or more pieces 1036) may reduce an air gap between the TMS device 1000 and the subject's head 52, which may increase (e.g., maximize) the efficiency of the TMS device 1000.

Adjusting the ferromagnetic component 1030 may allow for the creation of a local zone of lower electric field on a portion of the subject's anatomy (e.g., the surface of the subject's head). For example, adjusting the ferromagnetic component 1030 (e.g., by adding or removing one or more pieces 1036) may cause an electric field that is induced by the magnetic field (e.g., generated by the TMS device 1000) to develop a saddle point. The saddle point may result from adjusting the ferromagnetic component 1030 such that a gap between respective ones of the treatment coils 1010 is broadened or narrowed. For example, such a gap may be defined between a treatment coil 1010 supported by the third segment 1060 and a treatment coil 1010 supported by the fourth segment 1070. Such a saddle point may develop under the ferromagnetic component 1030, in a location near an interface between the second end 1064 of the third segment 1060 and the first end 1072 of the fourth segment 1070. The presence of a saddle point in an electric field induced by the TMS device 1000 may enable orienting the TMS device 1000 relative to subject anatomy (e.g., relative to a subject's head during TMS treatment) so as to avoid stimulating a surface location located over a location to be stimulated, and/or may enable the stimulation of tissue below a sensitive region of subject anatomy (e.g., a sensitive surface location on the subject). Peak induced electric fields may remain at the surface but not above (e.g., directly above) a location of interest. Neighboring tissues with similar conductivities may receive higher current density.

It should be appreciated that the adjustability features of the adjustable and/or reconfigurable TMS devices 900 and 1000 are not mutually exclusive, and that an adjustable and/or reconfigurable TMS device may be configured to include features from both TMS devices 900 and 1000. For example a TMS device may include one or more pieces that are joined to each other so as to be adjustable relative to each other (e.g., as depicted in FIG. 9), and may additionally include one or more pieces (e.g., segments) that are configured to be releasably attached to one another (e.g., as depicted in FIG. 10). A TMS device with such a configuration may be adjusted and/or reconfigured, for example, using a combination of the techniques described herein (e.g., relative to an anatomy of a subject, such as a subject's head).

Figure 11:
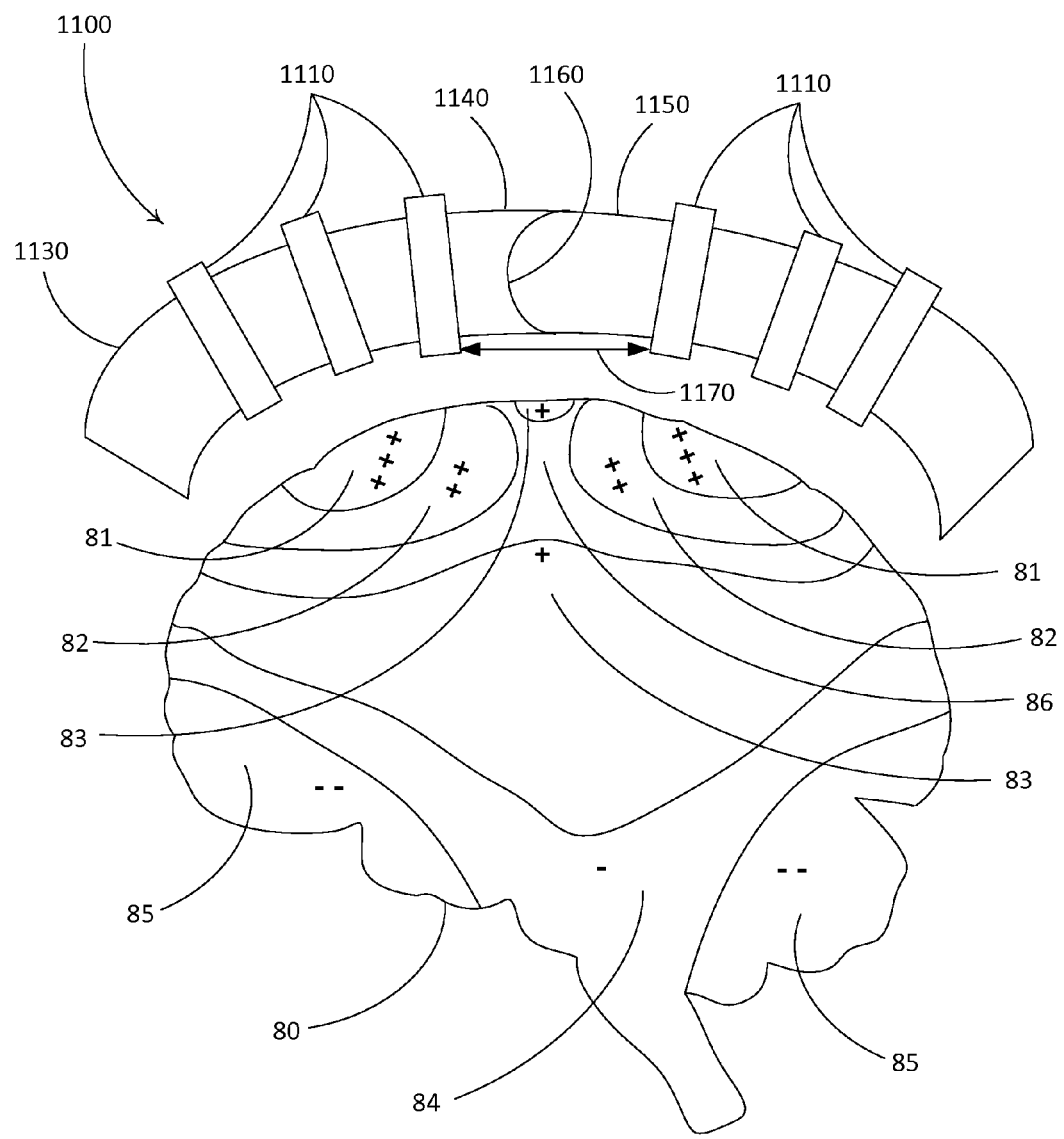
FIG. 11 depicts an example distribution of electrical field currents that may be induced by an example adjustable TMS device, wherein the induced electrical field exhibits a saddle point.

FIG. 11 depicts an example distribution of electrical field currents that may be induced by an example TMS device 1100. The TMS device 1100 may be an adjustable TMS device, such as the TMS device 900, the TMS device 1000, or another adjustable TMS device. The adjustable TMS device 1100 may include one or more treatment coils 1110 (e.g., a plurality of treatment coils 1110) and a ferromagnetic component 1130. The ferromagnetic component 1130 may be configured to be adjustable. For example, the ferromagnetic component 1130 may include first and second pieces 1140 and 1150 that are adjustable with respect to each other around a joint 1160.

The TMS device 1100 may be operated such that the treatment coils 1110 and the ferromagnetic component 1130 cooperatively generate a magnetic field in a target anatomy (e.g., the brain 80) of a human subject (e.g., a TMS patient). The magnetic field may induce currents in a targeted stimulation volume of the subject's brain 80. When the TMS device 1100 is operated, for example during TMS treatment, the stimulation volume may include one or more regions that exhibit different levels of induced current (e.g., regions 81, 82, and 83) and/or induced return currents (e.g., regions 84 and 85).

Adjusting the ferromagnetic component 1130 may cause an electric field that is induced by the magnetic field (e.g., generated by the TMS device 1100) to develop a saddle point (e.g., saddle point 86). The ferromagnetic component 1130 may be adjusted such that a gap between respective ones of the treatment coils 1110 is broadened or narrowed. For example, a gap 1170 may be defined between two treatment coils 1110 that are nearest to the joint 1160, the treatment coils 1110 supported by the first and second piece 1140, 1150, respectively. As shown, the saddle point 86 may develop under the ferromagnetic component 1130, proximate to the joint 1160. The saddle point 86 may enable orienting the TMS device 100 during TMS treatment (e.g., relative to a subject's head) so as to avoid stimulating a surface location located over a location to be stimulated, and/or may enable the stimulation of tissue below a sensitive region of subject anatomy (e.g., a sensitive surface location on the subject).

Figure 12:
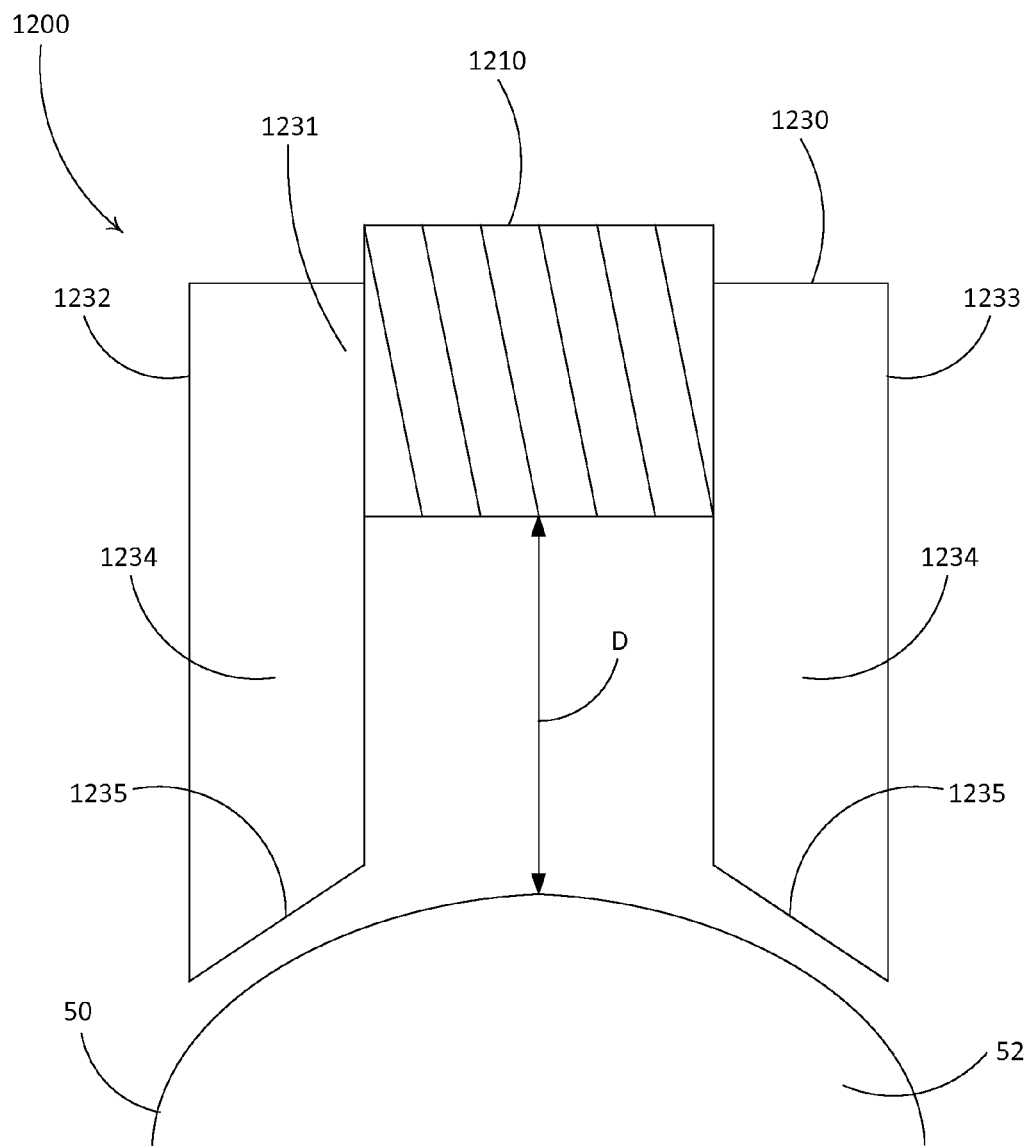
FIG. 12 depicts another example TMS device.

FIG. 12 depicts a human subject 50 and an example TMS device 1200 that is configured to generate a changing magnetic field in a target anatomy of the subject 50. The subject 50 may be, for example, a TMS patient. The target anatomy of the subject 50 may be, for example, brain tissue of the subject 50.

As shown, the TMS device 1200 includes a treatment coil 1210 and a ferromagnetic component 1230. The TMS device 1200 may be disposed proximate to the subject's head 52 in preparation for or during TMS treatment, for example as shown in FIG. 12.

The ferromagnetic component 1230 may be configured such that the treatment coil 1210 is spaced apart a distance D from one or more locations of subject anatomy (e.g., from an upper surface of the subject's head 52), such that heat transfer from the treatment coil 1210 to the subject 50 is controlled. For example, the distance D may be determined such that heat transfer from the treatment coil 1210 to the subject's head does not cause the skin temperature of the subject's head 52 to exceed a predetermined threshold.

The ferromagnetic component 1230 may define any suitable shape. As shown, the ferromagnetic component 1230 may include a rectangular upper portion 1231 that defines a first end 1232, an opposed second end 1233 that is spaced from the first end 1232, and an intermediate portion that extends between the first and second ends 1232, 1233. The ferromagnetic component may include one or more leg portions 1234 that may extend downward from the upper portion 1231. As shown, the ferromagnetic component 1230 includes two leg portions 1234. Each leg portion defines an upper end that is supported by the upper portion 1231 and an opposed free end 1235. A first one of the leg portions 1234 extends downward from the first end 1232 of the upper portion 1231, and a second one of the leg portions 1234 extends downward from the second end 1233 of the upper portion 1231. The leg portions 1234 may be configured to at least partially conform to subject anatomy. For example, the free ends 1235 of the illustrated leg portions are angled to at least partially conform to the shape of the subject's head 52.

The ferromagnetic component 1230 may be configured to support one or more treatment coils 1210. As shown, the intermediate portion of the ferromagnetic component 1230 is configured to support a treatment coil 1210. The ferromagnetic component 1230 may be assembled from separate pieces (e.g., the upper portion 1231 and leg portions 1234), or may be monolithic. The ferromagnetic component 1230, or one or more portions thereof, may be made of any material that exhibits suitable ferromagnetic properties, such as powdered ferromagnetic iron particles.

The TMS device 1200 may include one or more treatment coils 1210. The illustrated TMS device 1200 includes a single treatment coil 1210. The treatment coil 1210 may be defined by one or more windings (e.g., a plurality of windings). As shown, the windings may be fabricated by wrapping an electrically conductive material (e.g., copper wire) one or more times around an outer surface of the ferromagnetic component 1230 (e.g., directly onto the ferromagnetic component 1230 or onto an intermediate medium secured to the ferromagnetic component 1230) at a respective location. In another example, one or more windings may be embedded in the ferromagnetic component 1230. The windings may include one or more turns, and may have the same or different geometries. It should be appreciated that the TMS device 1200 is not limited to the illustrated treatment coil configuration. For example, the TMS device 1200 may be configured with more treatment coils 1210 in any suitable locations along the ferromagnetic component 1230.

The TMS device 1200 may be configured to be adjustable, such that the distance D may be configurable. For example, the one or more leg portions 1234 may be configured to be adjustable, such that the respective free ends 1235 of the leg portions 1234 may be moved closer to or further away from the upper portion 1231. Such reconfigurable leg portions 1234 may be configured to be freely adjustable (e.g., between two opposed positions) or may be incrementally adjustable (e.g., between predefined positions that are spaced apart from each other). The leg portions 1234 may be configured for manual length adjustment, automated length adjustment, or a combination thereof. The TMS device 1200 may be configured to be adjustable and/or reconfigurable in preparation for and/or during TMS treatment.

The adjustable TMS device 1200, for example as configured and oriented relative to a subject as depicted in FIG. 12, may be operated to cause the generation of a magnetic field in the subject's brain that may exhibit a greater intensity in an upper region of the subject's brain than in other regions of the subject's brain. When the TMS device 1200 is oriented relative to the subject 50 as shown, the magnetic field may be distributed so as to be simultaneously resident in both the first and second hemispheres of the subject's brain.

It should be appreciated that the TMS device 1200 is not limited to the illustrated orientation relative to a subject (e.g., to the head 52 of the subject 50), and that the TMS device 1200 may be differently oriented relative to the subject, such that the portion of the magnetic field that exhibits greater intensity is localized in a different location of the subject's anatomy (e.g., a different location in the subject's brain).

Adjusting the ferromagnetic component 1230 by altering the distance D between the treatment coil 1210 and the subject's head 52 (e.g., by adjusting the length of the leg portions 1234) may enable the control of the amount of heat transferred from the treatment coil 1210 to the subject's head 52. For example, one or both of the leg portions 1234 may be lengthened or shortened such that heat transfer from the treatment coil 1210 to the subject's head does not cause the skin temperature of the subject's head 52 to exceed a predetermined threshold.

The ferromagnetic component of a TMS device may be fabricated using any suitable techniques and/or materials. For example, one or more of the ferromagnetic components illustrated and described herein (e.g., ferromagnetic components 130, 230, 330a and 330b, 430a and 430b, 530a and 530b, 630, 730, 830, 930, 1030, 1130, and 1230) may be fabricated to include a distributed air gap structure. Such a distributed air gap structure may be created, for example, by dispersing powdered ferromagnetic particles (e.g., iron particles) in a matrix of insulating material. In an example process for manufacturing the ferromagnetic component of a TMS device, individual ferromagnetic particles in a powder may be mixed with a binding material, for example phenolic or epoxy. The ferromagnetic powder and binding mixture may be formed into a desired shape of the ferromagnetic component (e.g., by a pressing process). The formed ferromagnetic component may be subjected to a heating process (e.g., a baking process) in order to cure the material of the ferromagnetic component. The resulting ferromagnetic component may exhibit a distributed gap structure. This example fabrication process is explained in further detail in co-owned U.S. Pat. No. 7,824,324, the disclosure of which is incorporated herein by reference in its entirety.

One or more components of a TMS device T (e.g., any of the TMS devices 100, 200, 300, 400, 500, 600, 700, 800, 900, 1000, 1100, or 1200) may be configured to control temperatures associated with operation of the TMS device (e.g., prior to and/or during TMS treatment). For example, the ferromagnetic component of a TMS device may be configured for active cooling, passive cooling, or a combination thereof. For example, a ferromagnetic component may be configured with one or more active or passive heat transfer structures, such as heat sinks, openings (e.g., holes), cooling fins, etc. Such structures may enable, for instance, convective cooling, conductive cooling (e.g., fluid cooling), charge carrier transport, and so on. Such structures may be equipped with sensors (e.g., temperature sensors). A ferromagnetic component may be configured to be electrically and/or thermally insulating. In another example, one or more treatment coils of a TMS device may be configured for active cooling, passive cooling, or a combination thereof. For example, one or more treatment coils of a TMS device may be configured with one or more active or passive heat transfer structures, such as heat sinks, cooling fins, etc. Such structures may be equipped with sensors (e.g., temperature sensors).

Figure 13:
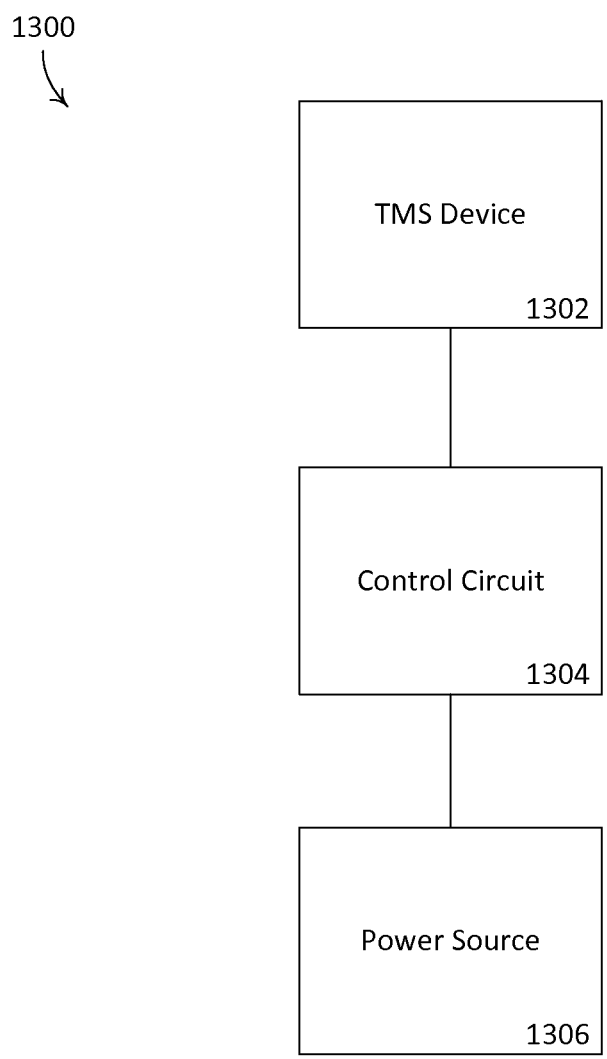
FIG. 13 is a simplified block diagram depicting an example TMS system.

FIG. 13 is a simplified block diagram depicting an example TMS system 1300 that may be used to apply TMS treatment to a human subject (e.g., a TMS patient). The TMS system 1300 includes a TMS device 1302. In an example implementation of the TMS system 1300, one of the example TMS devices described herein (e.g., any of the TMS devices 100, 200, 300, 400, 500, 600, 700, 800, 900, 1000, 1100, or 1200) may be implemented as the TMS device 1102. The TMS system 1300 further includes a control circuit 1304 that is in electrical communication with (e.g., electrically connected to) the TMS device 1302. The TMS system 1300 further includes a power source 1306 that is in electrical communication with (e.g., electrically connected to) the control circuit 1304. The power source 1306 may be, for example, an alternating current (AC) power source or a direct current (DC) power source. The power source 1306 may be a wired power source (e.g., a residential or commercial power source) or a portable power source (e.g., a battery, capacitor, or other energy storage device).

The TMS system 1300 may include a positioning apparatus (not shown) that is configured to support one or more of the TMS device 1302, the control circuit 1304, and the power source 1306. The positioning apparatus may be configured to enable secure (e.g., stabilized), adjustable positioning of the TMS device 1302, for example proximate to a treatment location on a subject (e.g., proximate to a subject's brain). The positioning apparatus may be, for example, a manipulable, repositionable arm to which the TMS device 1302 may be attached (e.g., removably mounted). Such a repositionable arm may be configured for manual adjustment (e.g., by a TMS treatment technician) and/or electronic adjustment (e.g., as a motorized, robotic arm). An electronically adjustable (e.g., robotic) arm may be configured for automated repositioning, for example based on feedback observed during a course of TMS treatment.

The control circuit 1304 may be configured to deliver pulses of electrical current from the power source 1306 to the TMS device 1302 (e.g., to one or more treatment coils of the TMS device 1302). For example, the control circuit 1304 may operate as a switch that delivers pulses of electrical current to the TMS device 1302 in accordance with the opening and/or closing of the switch. If the TMS device 1302 includes more than one treatment coil (e.g., in accordance with TMS devices 300, 400, 500, 900, 1000, or 1100), the control circuit 1304 may be configured to pulse the different treatment coils simultaneously, or in accordance with a predetermined sequence (e.g., sequentially, randomly, in a specified order, and so on). In such a configuration, the amount of current delivered in the pulses to the respective treatment coils may be the same or different.

The pulses of electrical current may cause the TMS device 1302 to generate a changing magnetic field, for example in a subject that is undergoing treatment from the TMS system 1300. For example, the control circuit 1304 may be in electrical communication with (e.g., electrically connected to) one or more treatment coils of the TMS device 1302 (e.g., the treatment coil 110 if the TMS device 100 is implemented as the TMS device 1302). Pulses of electrical current delivered to the TMS device 1302 from the control circuit 1304 may energize the one or more treatment coils, which may cause the one or more treatment coils to generate the changing magnetic field in the subject.

If the TMS device 1302 is operated without the one or more ferromagnetic components (e.g., if the one or more ferromagnetic components are removed from or otherwise omitted from the TMS device 1302), the one or more treatment coils of the TMS device 1302 may generate a first magnetic field in a target anatomy of the subject (e.g., in the subject's brain). The first magnetic field may exhibit a first set of characteristics, for example a volume of tissue in the target anatomy that is stimulated (e.g., a first stimulation volume), a penetration depth in the subject at which effective TMS treatment is achieved (e.g., effective penetration depth), varying levels of magnetic field intensity that may induce varying levels of electrical field intensity in the subject (e.g., such that electrical stimulation intensity levels near an outer surface of the subject's head vary from electrical stimulation intensity levels at the penetration depth), an electric field focality in the subject that is associated with the first magnetic field, and so on. In an example where the target anatomy is brain tissue of the subject, the stimulation volume may include, for example, a region (e.g., a three-dimensional volume) of cortical tissue within the magnetic field that is above a threshold of cortical stimulation.

A configuration in which the TMS device 1302 is operated without the one or more ferromagnetic components may be referred to as an air core treatment coil configuration. When the TMS device 1302 is operated in such a configuration, the first magnetic field generated by the TMS device 1302 may exhibit characteristics (e.g., first characteristics) that may include, for example, variable induced electrical stimulation intensities at various locations in a corresponding first volume of stimulated tissue, a first penetration depth (e.g., into the subject's brain), and a first electric field focality. Variable induced electrical stimulation intensities may include, for example, a first electrical stimulation intensity at a first location in or on the subject that is near an outer surface of the subject (e.g., at the surface of the subject's scalp, proximate to cranial nerves) and a second electrical stimulation intensity at a second location in the subject (e.g., in the subject's brain) that is spaced inwardly from the first location (e.g., at a greater depth in subject anatomy relative to the first location). The second location may be, for example near the effective penetration depth of the magnetic field. In an example where the target anatomy is brain tissue of the subject, the first magnetic field may be distributed in the subject's brain such that the volume of brain tissue stimulated by the first magnetic field simultaneously resides in both the first and second hemispheres of the subject's brain.

The strength of the first magnetic field may exhibit a gradient (e.g., a first gradient) between two locations in subject anatomy (e.g., target anatomy). The strength of the first magnetic field may be representative of, for example, the magnetic flux density B of the first magnetic field. The first gradient of magnetic field strength may be representative of a ratio of respective electrical field intensities induced by the first magnetic field at two selected locations in subject anatomy. In an example where the target anatomy is brain tissue of the subject, the first gradient of magnetic field strength may be representative of a peak dB/dt (time rate of change of magnetic field strength) near an outer surface of the subject's head (e.g., at the first location) versus peak dB/dt at an appropriate reference point in the subject's brain (e.g., at the second location).

When the TMS device 1302 is operated with the one or more ferromagnetic components attached to the corresponding one or more treatment coils, the treatment coils and the ferromagnetic components may operate cooperatively to generate a second magnetic field that may exhibit characteristics (e.g., second characteristics) that may differ from the characteristics exhibited by the first magnetic field. Such characteristics may include, for example, variable induced electrical stimulation intensities at various locations in a corresponding volume of tissue stimulated tissue by the second magnetic field (e.g., a second stimulation volume that may be the same or different from the first stimulation volume), a second penetration depth (e.g., into the subject's brain), and a second electric field focality. Variable induced electrical stimulation intensities may include, for example, a third electrical stimulation intensity at the first location that may be different from the first electrical stimulation intensity and a fourth electrical stimulation intensity at the second location that may be different from the second electrical stimulation intensity.

The strength of the second magnetic field may exhibit a gradient (e.g., a second gradient) between two locations in subject anatomy (e.g., target anatomy). The strength of the second magnetic field may be representative of, for example, the magnetic flux density B of the second magnetic field. The second gradient of magnetic field strength may be representative of a ratio of respective electrical field intensities induced by the second magnetic field at two selected locations in subject anatomy. In an example where the target anatomy is brain tissue of the subject, the second gradient of magnetic field strength may be representative of a peak dB/dt (time rate of change of magnetic field strength) near an outer surface of the subject's head (e.g., at the first location) versus peak dB/dt at an appropriate reference point in the subject's brain (e.g., at the second location).

The one or more ferromagnetic components may be configured such that when the TMS device 1302 is operated with the one or more ferromagnetic components attached to the corresponding one or more treatment coils, cooperative operation of the one or more ferromagnetic components and the one or more treatment coils causes the gradient of magnetic field strength gradient of the second magnetic field (e.g., the second gradient) to differ from the gradient of magnetic field strength of the first magnetic field (e.g., the first gradient). For example, the one or more ferromagnetic components may be configured such that the second gradient of magnetic field strength is less than the first gradient of magnetic field strength (e.g., such that the first gradient is steeper than the second gradient between, when measured at the same two locations, respectively).

To illustrate, the one or more ferromagnetic components may be configured such that, in comparison to operation of the TMS device 1302 in an air core treatment coil configuration, cooperative operation of the one or more ferromagnetic components and the one or more treatment coils causes the penetration depth of the second magnetic field generated by the TMS device 1302 to be effectively maintained relative to the penetration depth of the first magnetic field (e.g., such that the second penetration depth is not shallower than the first penetration depth), while surface electrical stimulation intensity (e.g., near the cranial nerves) caused by the second magnetic field may be reduced relative to the surface electrical stimulation intensity caused by the first magnetic field. For example, the electrical stimulation intensity exhibited by the second magnetic field at the first location (e.g., the third electrical stimulation intensity) may be lower than the electrical stimulation intensity exhibited by the first magnetic field at the same location (e.g., the first electrical stimulation intensity). The electrical stimulation intensity exhibited by the second magnetic field at the second location (e.g., the fourth electrical stimulation intensity) may be effectively the same as the electrical stimulation intensity exhibited by the first magnetic field at the same location (e.g., the second electrical stimulation intensity). Reducing the surface stimulation of the magnetic field generated by a TMS device (e.g., by creating a local surface reduction of the induced electric field) may allow TMS treatment to be applied proximate to one or surface locations (e.g., on a subject's head) that may be sensitive to electrical stimulation.

In another example, the one or more ferromagnetic components may be configured such that, in comparison to operation of the TMS device 1302 in an air core treatment coil configuration, cooperative operation of the one or more ferromagnetic components and the one or more treatment coils causes the surface electrical stimulation intensity (e.g., near the cranial nerves) caused by the second magnetic field to be effectively maintained relative to the surface electrical stimulation intensity caused by the first magnetic field, while the penetration depth of the second magnetic field generated by the TMS device 1302 is increased relative to the penetration depth of the first magnetic field (e.g., such that the second penetration depth is deeper than the first penetration depth). For example, the electrical stimulation intensity exhibited by the second magnetic field at the first location (e.g., the third electrical stimulation intensity) may effectively the same as the electrical stimulation intensity exhibited by the first magnetic field at the same location (e.g., the first electrical stimulation intensity). The electrical stimulation intensity exhibited by the second magnetic field at the second location (e.g., the fourth electrical stimulation intensity) may be greater than the electrical stimulation intensity exhibited by the first magnetic field at the same location (e.g., the second electrical stimulation intensity). Maintaining the surface stimulation of the magnetic field generated by a TMS device, while increasing the effective penetration depth, may enhance efficiency of TMS treatment.

In an example where the target anatomy is brain tissue of the subject, the second magnetic field may be distributed in the subject's brain such that the volume of brain tissue stimulated by the second magnetic field simultaneously resides in both the first and second hemispheres of the subject's brain. For example, the second magnetic field may stimulate a second volume of brain tissue in the subject's brain that substantially coincides with the first volume stimulated by the first magnetic field (e.g., such that the first and second stimulation volumes at least partially overlap each other). The first and second magnetic fields may stimulate volumes of brain tissue, for example, in a range of approximately two hundred fifty cubic millimeters (250 mm$^3$) to three hundred seventy five cubic millimeters (375 mm$^3$), for example a range of approximately two hundred seventy five cubic millimeters (275 mm³) to three hundred fifty five cubic millimeters (350 mm³), such as a volume of approximately three hundred cubic millimeters (300 mm³).

The respective focalities of the first and second electric fields induced by the first and second magnetic fields, respectively, may be effectively the same. For example, the second magnetic field may exhibit a second electrical field focality that is slightly reduced in comparison to the first electrical field focality exhibited by the first magnetic field.

When the TMS device 1302 is operated with the one or more ferromagnetic components attached to the corresponding one or more treatment coils, the ferromagnetic component may enable the TMS device 1302 to be spaced further from the subject's head during treatment, for example in comparison to a spacing between the TMS device 1302 and the subject's head when the TMS device 1302 is operated without the one or more ferromagnetic components (e.g. in accordance with an air core treatment coil configuration). This may protect the subject undergoing TMS treatment from temperature rise exhibited by the treatment coils. The amount of energy used by a TMS device (e.g., during TMS treatment) may be reduced if the TMS device includes one or more ferromagnetic components. This may mitigate temperature rise in one or more treatment coils of the TMS device.

The control circuit 1304 may be configured to pulse the TMS device 1302 so as to generate a changing magnetic field. For example, the control circuit 1304 may be configured to deliver pulses of electrical current to the TMS device 1302 in accordance with a predetermined pulse duration. The pulse duration may be determined, for example, in accordance with a desired penetration depth into target anatomy (e.g., into the subject's brain) that the magnetic field generated by the TMS device 1302 will exhibit.

In an example implementation of the TMS system 1300, the control circuit 1304 may be configured to deliver pulses of electrical current to the TMS device 1302 in accordance with a pulse duration that is in a range of approximately one hundred fifty microseconds (150 μs) to two hundred fifty microseconds (250 μs), for example a range of approximately one hundred ninety microseconds (190 μs) to two hundred ten microseconds (210 μs), for example a pulse duration of approximately two hundred microseconds (200 μs). Pulse durations within this range may cause the magnetic field generated by the TMS device 1302 to exhibit a penetration depth of approximately two-point-eight centimeters (2.8 cm) to five-point-five centimeters (3.5 cm), for example a penetration depth of approximately five centimeters (5 cm) (e.g., at least 5 cm). This penetration depth may be achieved, for example, when one of the TMS devices described herein (e.g., any of the TMS devices 100, 200, 300, 400, 500, 600, 700, 800, 900, 1000, 1100, or 1200) is implemented as the TMS device 1302 and pulsed by the control circuit 1304 in accordance with the described pulse durations.

Figure 14:
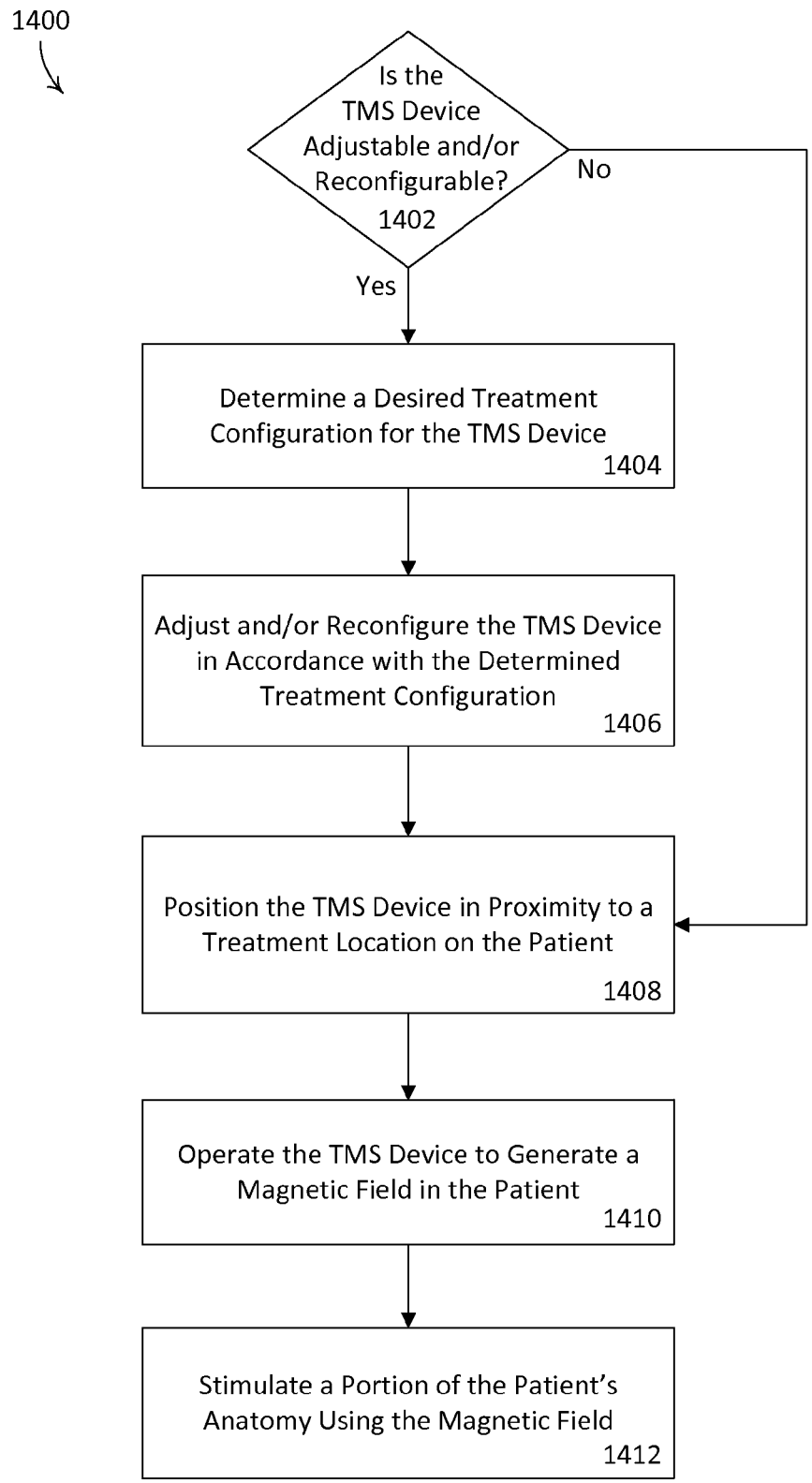
FIG. 14 is a flow diagram of an example TMS treatment process.

FIG. 14 is a flow diagram of an example TMS treatment process 1400. The TMS treatment process 1400 may be performed using a TMS device, such as one of the example TMS devices described herein (e.g., any of the TMS devices 100, 200, 300, 400, 500, 600, 700, 800, 900, 1000, 1100, or 1200).

At 1402, a TMS device may be selected for use in the TMS treatment process 1400. The TMS device may have a static configuration (e.g., in accordance with TMS devices 100, 200, 300, 400, 500, 600, 700, 800, and 1200) or may have an adjustable and/or reconfigurable configuration (e.g., in accordance with TMS devices 900, 1000, and adjustable configurations of TMS devices 300, 400, and 1100). If the selected TMS device has a static configuration, the treatment process 1400 may advance to 1408. If the selected TMS device has an adjustable and/or reconfigurable configuration, the treatment process 1400 may advance to 1404.

At 1404, a desired treatment configuration for the TMS device may be determined. This determination may be made based upon the anatomy of the subject at a desired treatment location. For example, the determination may be made in accordance with one or more of a size of the subject's head, a portion of the subject's brain that is to be treated, and the like.

At 1406, the TMS device may be adjusted and/or reconfigured in accordance with the determined treatment configuration. For example, if the TMS device 900 is selected as the TMS device for the treatment process 1400, the ferromagnetic component 930 may be adjusted, for example by adjusting the first and second pieces 940, 950. In another example, if the TMS device 1000 is selected as the TMS device for the treatment process 1400, the ferromagnetic component 1030 may be reconfigured by removing and/or replacing one or more pieces 1036 (e.g., one or more of the first through sixth segments 1040-1090). The treatment process 1400 may advance to 1408 when the TMS device has been adjusted and/or reconfigured in accordance with the determined treatment configuration.

At 1408, the TMS device may be positioned in proximity to a desired treatment location on the subject (e.g., proximate to the subject's head). For example, if the TMS device is mounted to a positioning apparatus, the positioning apparatus may be operated such that the one or more treatment coils of the TMS device are disposed near a cutaneous location on the subject's head.

At 1410, the TMS device may be operated to generate a magnetic field in the subject (e.g., in the subject's head). For example, a control circuit that is in electrical communication with the TMS device may be operated to deliver pulses of electrical current to the TMS device. At 1412, the magnetic field generated by the TMS device may be used to stimulate one or more portions of the subject's anatomy (e.g., one or more portions of the subject's brain). In an example, the one or more portions of the subject's brain may be stimulated in accordance with one or more stimulation cycles, with each stimulation cycle including five seconds of stimulation followed by a five second rest period. The stimulation may be performed at a frequency rate of approximately fifteen Hertz (15 Hz), for example.

The treatment process 1400 may include using the TMS device to determine a motor threshold location of the subject. The TMS device may be configured such that localization is not required during the motor threshold location procedure. For example, the TMS device (e.g., any of the TMS devices 100, 200, 300, 400, 500, 600, 700, 800, 900, 1000, 1100, or 1200) may be configured to generate a magnetic field in the subject's brain that stimulates a strip shaped region of the subject's brain (e.g., in an anterior-posterior direction) that encompasses the motor threshold location. A motor threshold location may be determined using localization of the TMS device. For example, the TMS device may be moved over an area of the subject's head until an indication of positioning is observed (e.g., until the subject's thumb moves or twitches indicating a motor threshold location). The motor threshold location may be determined, for example, using a stimulation frequency rate of approximately one (1) Hz. From the motor threshold location, the TMS device may be moved to the desired treatment location on the subject. In an example, the desired treatment location may be approximately five centimeters (5 cm) anteriorly from the determined motor threshold location.

TMS devices, such as the example TMS devices described herein (e.g., any of the TMS devices 100, 200, 300, 400, 500, 600, 700, 800, 900, 1000, 1100, or 1200), may be used to treat a number of conditions or disorders, for example depression, incontinence, and weight control issues. Such treatments may be applied to a subject, for example, using the example TMS devices in accordance with the example TMS treatment process 1400. The example TMS devices may be used to treat other conditions or disorders. For example, the TMS devices may be used in the rehabilitation of muscles. The TMS devices may be used in the treatment of peripheral nervous system disorders.

The example TMS devices may be used in one or more of the following treatment contexts, including major depressive disorder, epilepsy, schizophrenia, Parkinson's disease, Tourette's syndrome, amyotrophic lateral sclerosis (ALS), multiple sclerosis (MS), Alzheimer's disease, attention deficit/hyperactivity disorder (ADHD), obesity, bipolar disorder and/or mania, anxiety disorders (e.g., panic disorder with and without agoraphobia, social anxiety disorder, acute stress disorder, generalized anxiety disorder), post-traumatic stress disorder (PTSD), obsessive compulsive disorder (OCD), pain (e.g., migraine, trigeminal neuralgia), chronic pain disorders (e.g., pain due to diabetic neuropathy, post-herpetic neuralgia), idiopathic pain disorders (e.g., fibromyalgia, regional myofascial pain syndrome), rehabilitation following stroke (neuro plasticity induction), tinnitus, stimulation of implanted neurons to facilitate integration, substance-related disorders (e.g., dependence, abuse, and/or withdrawal diagnoses for alcohol, cocaine, amphetamine, caffeine, nicotine, cannabis, etc.), spinal cord injury and regeneration and/or rehabilitation, head injury, sleep deprivation reversal, primary sleep disorders (e.g., primary insomnia, primary hypersomnia, or circadian rhythm sleep disorder), cognitive enhancements, dementias, premenstrual dysphoric disorder (PMS), drug delivery systems (e.g., changing cell membrane permeability to a drug), induction of protein synthesis (e.g., induction of transcription and translation), stuttering, aphasia, dysphagia, essential tremor, and eating disorders (e.g., bulimia, anorexia, binge eating).

It should be appreciated that the example TMS devices may be employed for uses other than treatment applications. For example, the example TMS devices may be used (e.g., in accordance with the example TMS treatment process 1400) to perform diagnoses of one or more conditions in a subject. To illustrate, the example TMS devices may be used to diagnose a subject's response to drugs or other therapies, and/or may be used to quantify an effectiveness of such therapies. For example, a pharmaceutical may be known to have effects (e.g., direct or secondary effects) on the performance of the central nervous system. Such effects may be observed using the example TMS devices, for example by providing TMS and observing one or more of evoked potentials, motor response, conduction velocities, or other responses. Observed changes in one or more such response may be used, for example, to quantify a performance of the pharmaceutical or to determine an optimal dosing of the pharmaceutical.

The example TMS devices may be used (e.g., in accordance with the example TMS treatment process 1400) to perform diagnoses of one or more pathologies in a subject, for example by observing neurological response. Such pathologies may include, but are not limited to, degenerative diseases, extent of a traumatic injury, progression of a disease, systemic deficiencies, and congenital anomalies. To illustrate, the example TMS devices may be used in the diagnosis of, for example, compromised motor function, Alzheimer's disease, Parkinson's disease, ALS, MS, diabetic neuropathy, chronic demyelinating neuropathy, acute demyelinating neuropathy, epilepsy, vitamin B12 deficiency (e.g., pernicious anemia), vitamin E deficiency, neurosarcoidosis, tinnitus, and stroke. The example TMS devices may be used to evaluate the efficacy of treatments for such pathologies. For example, the TMS devices may be used to assess and/or measure the effect of pharmaceuticals, for example anti-convulsives, Alzheimer's medications, antipsychotics, pain medications, antianxiety medications, hypnotics (sedatives), analgesics (central), ADHD medications, or anesthetics.

It should be appreciated that the example TMS devices described herein (e.g., any of the TMS devices 100, 200, 300, 400, 500, 600, 700, 800, 900, 1000, 1100, or 1200) are not limited to their illustrated configurations. For example, one or more components from a first one of the example TMS devices may be implemented in a second one of the example TMS devices. In an example illustration, a ferromagnetic component that is configured similarly to the ferromagnetic component 230 of the TMS device 200 may be substituted for the ferromagnetic component 130 of the TMS device 100. In another example illustration, one or both of the first and second treatment coils 410*a*, 410*b* of the TMS device 400 may be substituted for the corresponding first and/or second treatment coils 310*a*, 310*b* of the TMS device 300. One of ordinary skill in the art will appreciate that these and other different configurations of the example TMS devices may be implemented without departing from the scope and spirit of the instant disclosure.

What is claimed:
1. A transcranial magnetic stimulation (TMS) device comprising:
    a treatment coil comprising:
        a base portion that is configured to reside near a cranial surface of a human subject and is configured to substantially conform to the cranial surface of the human subject; and
        a protruding portion that is angularly offset from the base portion and extends outwardly from the base portion in a direction away from the surface of the human subject when the base portion is placed in conforming relation with the cranial surface of the human subject; and
    a ferromagnetic component covering at least a portion of the base portion;
    wherein the treatment coil and the ferromagnetic component, in cooperative operation, are configured to generate a magnetic field in a target anatomy of the human subject, wherein the magnetic field is configured to induce a first electrical stimulation intensity at a first location in the human subject near an outer surface of the human subject, and induce a second electrical stimulation intensity at a second location in the human subject that is spaced inwardly from the first location; and
    wherein the magnetic field is further configured to induce return currents in the subject, and the ferromagnetic component is configured to spread the return currents generated by the magnetic field, such that the return currents cover a larger region in the subject as compared to the size of the region covered by the return currents induced by a magnetic field generated by the treatment coil without the inclusion of the ferromagnetic component.

2. The TMS device of claim 1, wherein the inclusion of the ferromagnetic component is configured to reduce an amount of energy needed to cause the treatment coil to generate the magnetic field as compared to an amount of energy needed to cause the treatment coil to generate the magnetic field without the inclusion of the ferromagnetic component.

3. The TMS device of claim 1, wherein the inclusion of the ferromagnetic component is configured to reduce an amount of heat omitted by the treatment coil when the treatment coil generates the magnetic field as compared to an amount of heat emitted by the treatment coil when the treatment coil generates the magnetic field without the inclusion of the ferromagnetic component.

4. The TMS device of claim 1, wherein the target anatomy is brain tissue of the subject, and the magnetic field is configured to induce the return currents in a third location near the outer surface of the subject's head.

5. The TMS device of claim 1, wherein the magnetic field is configured to stimulate a volume of tissue in the subject's brain that corresponds to the target anatomy, and wherein the return currents induced by the magnetic field are spread so as to reduce a current density outside of the stimulated volume of tissue.

6. The TMS device of claim 1, wherein the target anatomy is brain tissue of the subject, and the magnetic field is configured to induce the return currents in a predetermined location of the subject's head that is associated with a reduced sensitivity to TMS treatment.

7. The TMS device of claim 1, wherein the inclusion of the ferromagnetic component is configured to cause the magnetic field to achieve a penetration depth into the target anatomy that is at least as deep a penetration depth that is achieved by the magnetic field when the treatment coil generates the magnetic field without the inclusion of the ferromagnetic component; and
wherein the inclusion of the ferromagnetic component is further configured to reduce the first electrical stimulation intensity at the first location in the human subject caused by the magnetic field as compared to an electrical stimulation intensity at the first location caused by the magnetic field when the treatment coil generates the magnetic field without the inclusion of the ferromagnetic component.

8. The TMS device of claim 1, wherein the inclusion of the ferromagnetic component is further configured to maintain or reduce the first electrical stimulation intensity at the first location in the human subject caused by the magnetic field as compared to an electrical stimulation intensity at the first location caused by the magnetic field when the treatment coil generates the magnetic field without the inclusion of the ferromagnetic component; and
wherein the inclusion of the ferromagnetic component is configured to cause the magnetic field to achieve a penetration depth into the target anatomy that is deeper than a penetration depth that is achieved by the magnetic field when the treatment coil generates the magnetic field without the inclusion of the ferromagnetic component.

9. The TMS device of claim 1, wherein the ferromagnetic component comprises powdered ferromagnetic iron particles.

10. The TMS device of claim 1, wherein the treatment coil comprises a plurality of windings that define respective perimeters.

11. The TMS device of claim 10, wherein the plurality of windings follow a pattern of sequentially increasing perimeter size from an inner most winding to an outer most winding.

12. The TMS device of claim 10, wherein the ferromagnetic component defines an inner surface that covers a portion of the treatment coil.

13. The TMS device of claim 10, wherein the ferromagnetic component defines an opening that extends therethrough, the opening located in a portion of the ferromagnetic component that does not cover the plurality of windings.

14. The TMS device of claim 1, further comprising a control circuit that is in electrical communication with the treatment coil and that is configured to deliver pulses of electrical current to the treatment coil, wherein the pulses of electrical current cause the treatment coil and the ferromagnetic component to cooperatively generate the magnetic field.

15. A device that is configured to apply transcranial magnetic stimulation treatment to a human subject, the device comprising:
a treatment coil that is configured to partially enclose a region of the head of the subject, wherein the treatment coil comprises:
a base portion that is configured to reside near and substantially conforms to a cranial surface of a human subject; and
a protruding portion that is angularly offset relative to the base portion and that extends outwardly from the base portion in a direction away from the cranial surface of the human subject when the base portion is placed in conforming relation with the cranial surface of the human subject; and
a ferromagnetic component that at least partially encloses and extends beyond the base portion of the treatment coil, the ferromagnetic component shaped to conform to the subject's head,
wherein the treatment coil and the ferromagnetic component, in cooperative operation, are configured to generate a magnetic field in a target anatomy of the human subject, wherein the magnetic field is configured to induce a first electrical stimulation intensity at a first location in the human subject near an outer surface of the human subject, and induce a second electrical stimulation intensity at a second location in the human subject that is spaced inwardly from the first location;
wherein the inclusion of the ferromagnetic component is configured to cause the magnetic field to achieve a penetration depth into the target anatomy that is at least as deep a penetration depth that is achieved by the magnetic field when the treatment coil generates the magnetic field without the inclusion of the ferromagnetic component; and
wherein the inclusion of the ferromagnetic component is further configured to reduce the first electrical stimulation intensity at the first location in the human subject caused by the magnetic field as compared to an electrical stimulation intensity at the first location caused by the magnetic field when the treatment coil generates the magnetic field without the inclusion of the ferromagnetic component.

16. The device of claim 15, wherein a portion of the ferromagnetic component extends toward the protruding portion of the treatment coil.

17. The device of claim 15, wherein the ferromagnetic component extends beyond the protruding portion of the treatment coil.

18. The device of claim 15, wherein the treatment coil comprises a plurality of windings.

19. The device of claim 15, wherein the ferromagnetic component at least partially encloses the protruding portion of the treatment coil.

20. The device of claim 15, wherein the base portion defines a concave surface that is configured to substantially conform to the cranial surface of the human subject.

21. The device of claim 15, wherein the magnetic field is further configured to induce return currents in the subject, and the ferromagnetic component is configured to spread the return currents generated by the magnetic field, such that the return currents cover a larger region in the subject as compared to the size of the region covered by the return currents induced by a magnetic field generated by the treatment coil without the inclusion of the ferromagnetic component.

* * * * *